US007358052B2

(12) United States Patent
Singh

(10) Patent No.: US 7,358,052 B2
(45) Date of Patent: *Apr. 15, 2008

(54) CATALYTIC AMPLIFICATION OF MULTIPLEXED ASSAY SIGNALS

(75) Inventor: Sharat Singh, San Jose, CA (US)

(73) Assignee: Monogram Biosciences, Inc., South San Francisco, CA (US)

(*) Notice: Subject to any disclaimer, the term of this patent is extended or adjusted under 35 U.S.C. 154(b) by 813 days.

This patent is subject to a terminal disclaimer.

(21) Appl. No.: 10/154,641

(22) Filed: May 24, 2002

(65) Prior Publication Data

US 2002/0197649 A1 Dec. 26, 2002

Related U.S. Application Data

(60) Provisional application No. 60/340,652, filed on Dec. 12, 2001, provisional application No. 60/293,821, filed on May 26, 2001.

(51) Int. Cl.
*G01N 33/53* (2006.01)
*G01N 33/533* (2006.01)
*C12Q 1/42* (2006.01)

(52) U.S. Cl. .............. 435/7.1; 435/7.72; 435/7.95; 435/21; 436/546; 436/161

(58) Field of Classification Search .............. 435/6, 435/7.1, 7.5, 961, 968, 7.72, 7.95, 21; 436/544, 436/161, 805, 173, 824, 546; 530/413
See application file for complete search history.

(56) References Cited

U.S. PATENT DOCUMENTS

| | | | |
|---|---|---|---|
| 4,274,240 A | 6/1981 | Soum | 52/583 |
| 4,331,590 A | 5/1982 | Bocuslaski | 260/112 B |
| 4,650,750 A | 3/1987 | Giese | 435/7 |
| 4,675,300 A | 6/1987 | Zare | 436/172 |
| 4,709,016 A | 11/1987 | Giese | 530/389 |
| 4,780,421 A | 10/1988 | Kameda | 436/518 |
| 5,057,412 A | 10/1991 | Rabin | 435/6 |
| 5,254,469 A | 10/1993 | Warren, III | 435/188 |
| 5,324,401 A | 6/1994 | Yeung | 204/180.1 |
| 5,340,716 A | 8/1994 | Ullman | 435/6 |
| 5,360,819 A | 11/1994 | Giese | 514/538 |
| 5,470,705 A | 11/1995 | Grossman | 435/6 |
| 5,494,793 A | 2/1996 | Schindele | 435/6 |
| 5,514,543 A | 5/1996 | Grossman | 435/6 |
| 5,516,636 A | 5/1996 | McCapra | 435/6 |
| 5,516,931 A | 5/1996 | Giese | 560/59 |
| 5,536,834 A | 7/1996 | Singh | 544/98 |
| 5,560,811 A | 10/1996 | Briggs | 204/451 |
| 5,565,324 A | 10/1996 | Still | 435/6 |
| 5,567,292 A | 10/1996 | Madabhushi | 204/451 |
| 5,573,906 A | 11/1996 | Bannwarth | 435/6 |
| 5,578,498 A | 11/1996 | Singh | 436/518 |
| 5,580,732 A | 12/1996 | Grossman | 435/6 |
| 5,602,273 A | 2/1997 | Giese | 560/60 |
| 5,604,104 A | 2/1997 | Giese | 435/7.1 |
| 5,610,020 A | 3/1997 | Giese | 435/7.1 |
| 5,616,719 A | 4/1997 | Davalian | 546/334 |
| 5,624,800 A | 4/1997 | Grossman | 435/6 |
| 5,650,270 A | 7/1997 | Giese | 435/6 |
| 5,691,151 A | 11/1997 | Braun | 435/7.2 |
| 5,703,222 A | 12/1997 | Grossman | 536/24.3 |
| 5,705,622 A * | 1/1998 | McCapra | 536/23.1 |
| 5,709,994 A | 1/1998 | Pease | 435/4 |
| 5,719,028 A | 2/1998 | Dahlberg | 435/6 |
| 5,721,099 A | 2/1998 | Still | 435/6 |
| 5,723,591 A | 3/1998 | Livak | 536/22.1 |
| 5,756,726 A | 5/1998 | Hemmi | 540/474 |
| 5,763,602 A | 6/1998 | Li | 540/128 |
| 5,766,481 A | 6/1998 | Zambias | 210/656 |

(Continued)

FOREIGN PATENT DOCUMENTS

EP 0 484 027 A1 5/1992

(Continued)

OTHER PUBLICATIONS

Adam et al., "Photooxygenation (Singlet Oxygen) of Tetrathioethylenes", Journal of the American Chemical Society, vol. 94:4, 1972, pp. 1206-1208.

(Continued)

*Primary Examiner*—Long V. Le
*Assistant Examiner*—Shafiqul Haq
(74) *Attorney, Agent, or Firm*—Fenwick & West LLP

(57) ABSTRACT

Methods, compositions, kits, and a system are disclosed for detecting one or more analytes in a sample. A mixture comprising the (i) sample, (ii) a first binding reagent comprising a cleavage-inducing moiety and a first binding agent specific for an analyte, and (ii) one or more electrophoretic probes each having a second binding agent is subjected to conditions under which binding of respective binding agents occurs. The interaction between the binding agents and the analyte brings the cleavage-inducing moiety within a proximity effective for cleaving a cleavable linkage tethering an electrophoretic tag to the second binding agent, thereby releasing the tag for electrophoretic separation. Separation of different tags occurs by virtue of their distinct electrophoretic mobilities. After separation, a signal amplification moiety on each tag is activated to generate a signal to indicate the presence of a particular analyte in the sample.

25 Claims, 9 Drawing Sheets

U.S. PATENT DOCUMENTS

| | | | | |
|---|---|---|---|---|
| 5,777,096 | A | 7/1998 | Grossman | 536/24.3 |
| 5,789,172 | A | 8/1998 | Still | 435/6 |
| 5,807,675 | A | 9/1998 | Davalian | 435/6 |
| 5,807,682 | A | 9/1998 | Grossman | 435/6 |
| 5,811,239 | A | 9/1998 | Frayne | 435/6 |
| 5,843,655 | A | 12/1998 | McGall | 435/6 |
| 5,843,666 | A | 12/1998 | Akhavan-Tafti | 435/6 |
| 5,846,839 | A | 12/1998 | Gallop | 436/518 |
| 5,849,878 | A | 12/1998 | Cantor | 530/391.9 |
| 5,851,770 | A | 12/1998 | Babon | 435/6 |
| 5,874,213 | A | 2/1999 | Cummins | 435/6 |
| 5,876,930 | A | 3/1999 | Livak | 435/6 |
| 5,916,426 | A | 6/1999 | Madabhushi | 204/451 |
| 5,952,654 | A | 9/1999 | Giese | 250/288 |
| 5,958,202 | A | 9/1999 | Regnier | 204/451 |
| 5,986,076 | A | 11/1999 | Rothschild | 536/22.1 |
| 5,989,871 | A | 11/1999 | Grossman | 435/9.1 |
| 5,998,140 | A | 12/1999 | Dervan | 435/6 |
| 6,001,567 | A | 12/1999 | Brow | 435/6 |
| 6,001,579 | A | 12/1999 | Still | 435/7.1 |
| 6,027,890 | A | 2/2000 | Ness | 435/6 |
| 6,045,676 | A | 4/2000 | Mathies | 204/603 |
| 6,090,947 | A | 7/2000 | Dervan | 548/312.4 |
| 6,251,581 | B1 | 6/2001 | Ullman | 435/4 |
| 6,312,893 | B1 | 11/2001 | Van Ness | 435/6 |
| 6,322,980 | B1 | 11/2001 | Singh | 435/6 |
| 6,331,530 | B1 | 12/2001 | Breslow | 514/58 |
| 6,335,201 | B1 | 1/2002 | Allbritton | 436/63 |
| 6,346,529 | B1 | 2/2002 | Floyd | 514/226.2 |
| 6,368,874 | B1 | 4/2002 | Gallop | 436/518 |
| 6,613,508 | B1* | 9/2003 | Ness et al. | 435/6 |
| 2002/0037542 | A1 | 3/2002 | Allbritton | 435/7.23 |
| 2002/0128465 | A1 | 9/2002 | Lyamichev | 536/24.3 |
| 2002/0150927 | A1* | 10/2002 | Matray et al. | 435/6 |
| 2003/0235832 | A1* | 12/2003 | Chenna et al. | 435/6 |

FOREIGN PATENT DOCUMENTS

| | | |
|---|---|---|
| WO | WO 93/06121 | 4/1993 |
| WO | WO 96/24061 | 8/1996 |
| WO | WO 97/27325 | 7/1997 |
| WO | WO 97/27327 | 7/1997 |
| WO | WO 97/28275 | 8/1997 |
| WO | WO 98/01533 | 1/1998 |
| WO | WO 98/15830 | 4/1998 |
| WO | WO 99/05319 | 2/1999 |
| WO | WO 99/13108 | 3/1999 |
| WO | WO 99/42838 | 8/1999 |
| WO | WO 99/64519 | 12/1999 |
| WO | WO 00/56925 | 9/2000 |
| WO | WO 00/66607 | 11/2000 |

OTHER PUBLICATIONS

Adam et al., "Photooxygenation of Vinyl Sulfides: Substituent Effects on the [2+2] Cycloaddition versus Schenck Ene Reaction Modes", Tetrahedron Letters, vol. 36, No. 43, Pergamon Press 1995, pp. 7853-7854.

Ando et al., "Photosensitized Oxygenation of Vinylic Sulphides", J.C.S. Chem. Comm., 1972, pp. 477-478.

Ando et al., "Singlet Oxygen Reaction—II Alkylthiosubstituted Ethylene[1]", Tetrahedron, vol. 29, Pergamon Press 1973, pp. 1507-1513.

Ando et al., "Singlet Oxygen Reaction. III. Solvent and Temperature Effects on the Photosensitized Oxygenation of Vinyl Sulfides and Vinyl Ethers", Journal of the American Chemical Society, vol. 96:21, 1974, pp. 6766-6768.

Ando et al., "Singlet Oxygen Reaction. IV. Photooxygenation of Enamines Involving a Two-Step Cleavage of a 1, 2-Dioxetane Intermediate[1]", Journal of American Chemical Society, vol. 97:17, 1975, pp. 5028-5029.

Ando et al., "Singlet Oxygen Reaction V. Ring Size Effects on the Decomposition of Sulfur Substituted 1, 2-Dioxetane[1]", Tetrahedron Letters, No. 47, Pergamon Press 1975, pp. 4127-4130.

Brenner et al., "Encoded Combinatorial Chemistry", Proc. Natl. Acad. Sci. USA, vol. 89, 1992, pp. 5381-5383.

Fitch et al., "Improved Methods for Encoding and Decoding Dialkylamine-Encoded Combinatorial Libraries", J. Comb. Chem., 1, 1999, pp. 188-194.

Giese, "Electrophoric Release Tags: Ultrasensitive Molecular Labels Providing Multiplicity", Trends in Analytical Chemistry, vol. 2, No. 7, 1983, pp. 166-168.

Gomer, "Preclinical Examination of First and Second Generation Photosensitizers Used in Photodynamic Therapy", Photochemistry and Photobiology, vol. 54, No. 6, 1991, pp. 1093-1107.

Hacia et al., "Detection of Heterozygous Mutations in BRCA1 Using High Density Oligonucleotide Arrays and Two-Colour Fluorescence Analysis", Nature Genetics, vol. 14, 1996, pp. 441-447.

Haff et al., "Multiplex Genotyping of PCR Products with MassTag-Labled Primers", Nucleic Acids Research, vol. 25, No. 18, 1997, pp. 3749-3750.

Holland et al., "Detection of Specific Polymerase Chain Reaction Product by Utilizing the 5! → 3! Exonuclease Activity of *Thermus Aquaticus* DNA Polymerase", Proc. Natl. Acad. Sci. USA, vol. 88, 1991, pp. 7276-7280.

Houghten et al., "Human β -Endorphin: Synthesis and Characterization of Analogs Iodinated and Tritiated at Tryosine Residues 1 and 27", Int. J. Peptide Protein Res., vol. 16, 1980, pp. 311-320.

Kochevar et al., "Photosensitized Production of Singlet Oxygen", Methods in Enzymology, vol. 319, 2000, pp. 20-29.

Lee et al., "Allelic Discrimination by Nick-Translation PCR with Fluorogenic Probes", Nucleic Acids Research, vol. 21, No. 16, 1993, pp. 3761-3766.

Liu et al., "Capillary Electrochromatography-laser-induced Fluorescence Method for Separation and Detection of Dansylated Dialkylamine Tags in Encoded Combinatorial Libraries", Journal of Chromatorgraphy, Art. 924, 2001, pp. 323-329.

Lu et al., "Polymerizable Fab' Antibody Fragments for Targeting of Anticancer Drugs", Nature Biotechnology, vol. 17, 1999, pp. 1101-1104.

Lum et al., "Ability of Specific Monoclonal Antibodies and Conventional Antisera Conjugated to Hematoporphyrin to Label and Kill Selected Cell Lines Subsequent to Light Activation", Cancer Research, vol. 45, 1985, pp. 4380-4386.

Marglin et al., "Chemical Synthesis of Peptides and Proteins", Art. 739, 1970, pp. 841-866.

Marino et al., "Characterization of Mitochondrial DNA Using Low-Stringency Single Specific Primer Amplification Analyzed by Laser Induced Fluoroscene—Capillary Electrophoresis", Electrophoresis, vol. 17, 1996, pp. 1499-1504.

Matthews et al., "Analytical Strategies for the Use of DNA Probes", Analytical Biochemistry, vol. 169, 1988, pp. 1-25.

Merrifield, "Solid Phase Peptide Synthesis. I. The Synthesis of a Tetrapeptide", Synthesis of a Tetrapeptide, vol. 85, 1963, pp. 2149-2154.

Ni et al., "Versatile Approach to Encoding Combinatorial Organic Synthesis Using Chemically Robust Secondary Amine Tags", J. Med. Chem., vol. 39, 1996, pp. 1601-1608.

Olejnik et al., "Photocleavable Affinity Tags for Isolation and Detection of Biomolecules", Methods in Enzymology, vol. 291, 1998, pp. 135-154.

Oseroff et al., "Antibody-Targeted Photolysis: Selective photodestruction of Human T-Cell Leukemia Cells Using Monoclonal Antibody-Chlorin $_{e6}$ Conjugates", Proc. Natl. Acad. Sci. USA, vol. 83, 1986, pp. 8744-8748.

Pastinen et al., "Multiplex, Fluorescent, Solid-Phase Minisequencing for Efficient Screening of DNA Sequence Variation", Clinical Chemistry, vol. 42:9, 1996, pp. 1391-1397.

Posewitz et al., "Immobilized Gallium(III) Affinity Chromatography of Phosphopeptides", Anal. Chem., vol. 71, 1999, pp. 2883-2892.

Rakestraw et al., "Antibody-Targeted photolysis: In vitro Studies with Sn(IV) Chlorin e6 Covalently Bound to Monoclonal Antibodies Using a Modified Dextran Carrier", Proc. Natl. Acad. Sci. USA, vol. 87, 1990, pp. 4217-4221.

Da Ros et al., "DNA-Photocleavage Agents", Current Pharmaceutical Design, vol. 7, 2001, pp. 1781-1821.

Ross et al., "Discrimination of Single-Nucleotide Polymorphisms in Human DNA Using Peptide Nucleic Acid Probes Detected by MALDI-TOF Mass Spectrometry", Anal. Chem., vol. 69, 1997, pp. 4197-4202.

Sharman et al., "Role of Activated Oxygen Species in Photodynamic Therapy", Methods in Enzymology, vol. 319, 2000, pp. 376-400.

Still, "Discovery of Sequence-Selective Peptide Binding by Synthetic Receptors Using Encoded Combinatorial Libraries", Acc. Chem. Res., vol. 29, 1996, pp. 155-163.

Strong, "Antibody-Targeted Photolysis", Annals New York Academy of Sciences, vol. 745, 1994, pp. 297-320.

Ullman et al., "Luminescent Oxygen Channeling Immunoassay: Measurement of Particle Binding Kinetics by Chemiluminescence", Proc. Natl. Acad. Sci. USA, vol. 91, 1994, pp. 5426-5430.

Wang et al., "Large-Scale Identification, Mapping, and Genotyping of Single-Nucleotide Polymorphisms in the Human Genome", Science, vol. 280, 1998, pp. 1077-1082.

Wasserman et al., "Enamine-Single Oxygen Reactions. α-Diketones from Intermediate Amino Dioxetanes", Tetrahedron Letters, No. 21, 1975, pp. 1735-1738.

Wetmur, "DNA Probes: Applications of the Principles of Nucleic Acid Hybridization", Critical Reviews in Biochemistry and Molecular Biology, vol. 26, 1991, pp. 227-259.

White, "The Future of PCR Technology: Diversification of Technologies and Applications", Tibtech, vol. 14, 1996, pp. 478-483.

Wöhrle, "Porphyrins, Phthalocyanines, and Naphthalocyannies for Various Processes fo Visible Light Driven Conversion Processes", Chimia, vol. 45, 1991, pp. 307-310.

Woolley et al., "Functional Integration of PCR Amplification and Capillary Electrophoresis in a Microfabricated DNA Analysis Device", Anal. Chem., vol. 68, 1996, pp. 4081-4086.

Yarmush et al., "Antibody Targeted Photolysis", Critical Reviews in Therapeutic Drug Carrier Systems, vol. 10, 1993, pp. 197-252.

Yemul et al., "Selective Killing of T Lymphocytes by Phototoxic Liposomes", Proc. Natl. Acad. Sci. USA, vol. 84, 1987, pp. 246-250.

Zaklika et al., "Mechanisms of 1,2-Dioxetane Decomposition: The Role of Electron Transfer", Photochemistry and Photobiology, vol. 30, 1979, pp. 35-44.

\* cited by examiner

Thiazole cleavable linkage

Oxazole cleavable linkage

CATALYTIC AMPLIFICATION OF MULTIPLEXED ASSAY SIGNALS

This patent application claims priority to U.S. provisional patent application Ser. Nos. 60/340,652 filed on Dec. 12, 2001, and 60/293,821 filed on May 26, 2001, both of which are incorporated herein in their entirety by reference.

FIELD OF THE INVENTION

The present invention relates to methods, reagents and kits for use in assays employing catalyst-linked probes for detecting the binding of or interaction between the two components of one or more binding pairs.

BACKGROUND OF THE INVENTION

Important characteristics of an effective commercial assay include specificity, sensitivity, a high multiplexing capacity, and the ability to perform the assay rapidly and in a cost-effective manner, preferably through automation. For nucleic acid assays, many strategies have been designed to improve sensitivity that involve amplification of either the target sequence, e.g. polymerase chain reaction (PRC), or amplification of the signal generated from a recognition event, e.g. Invader® assay, U.S. Pat. No. 5,846,717. In contrast, for non-nucleic acid analytes, the option of target amplification is generally not available; thus, increases in sensitivity are brought about by signal amplification, e.g. enzyme-linked immunoabsorbent assays (ELISAs), Malik et al, Editors, Antibody Techniques (Academic Press, New York, 1994); tryamide signal amplification (TSA), Bobrow et al, J. Immunol. Methods, 125: 279-285 (1989); and the like.

In spite of the tremendous progress that has been made in recent years toward the developing highly sensitive and robust assay systems, few if any of the current technologies combine high sensitivity, specificity, and facile multiplexing capability. As a result, in some applications, such as certain drug screening or toxicological studies where samples are scarce, one has only a very limited ability to measure multiple analytes in individual samples.

In view of the above, it would be advantageous to many fields, particularly the fields of life science and pharmaceutical research, to have available a broadly applicable, specific, and sensitive assay technique that can be readily adapted for measuring multiple analytes in a single sample.

SUMMARY OF THE INVENTION

In one aspect the present invention is directed to a system and method for determining the presence and/or amount of one or more target analytes in a sample suspected of containing the target analytes. The method of the invention comprises the steps of (i) providing a first binding reagent and one or more electrophoretic probes, the first binding reagent having a cleavage-inducing moiety with an effective proximity and a first binding agent specific for at least one analyte, and the one or more electrophoretic probes each having a second binding agent specific for at least one analyte and each having one or more electrophoretic tags each such tag attached thereto by a cleavable linkage and each such tag having a signal amplification moiety; (ii) mixing the sample, the first binding reagent, and the one or more electrophoretic probes such that the first binding reagent and the one or more electrophoretic probes bind to the one or more analytes and at least one cleavable linkage of the one or more electrophoretic probes is within the effective proximity of a cleavage-inducing moiety so that one or more electrophoretic tags are released; (iii) electrophoretically separating the released electrophoretic tags in an electrophoretic separation medium that contains one or more substrates capable of reacting with at least one signal amplification moiety to produce a signal; and (iv) determining the presence or absence of the one or more analytes based on the presence or absence of signals produced by reactions between a substrate and a signal amplification moiety of the released electrophoretic tags. Preferably, each electrophoretic tag has unique charge-mass characteristics so that each different tag may be resolved into distinct peaks, e.g. in an electropherogram, upon electrophoretic separation.

In another aspect, the invention is directed to compositions for carrying out the steps of the method, such compositions including sets electrophoretic probes, sets of electrophoretic tags, electrophoretic separation media comprising one or more substrates capable of reacting with one or more signal amplification moieties, and binding compositions comprising mixtures of electrophoretic probes and first binding reagents. In one aspect, electrophoretic probes of the invention are defined by the formula:

wherein: T is a second binding agent specific for a target polypeptide, L is an oxidation-labile linkage, E is an electrophoretic tag comprising a signal amplification moiety, and k is an integer greater than or equal to 1.

In still another aspect, the invention is directed to a system for detecting a plurality of analytes that includes binding reagents for interacting with analytes, electrophoretic tags that serve as reporters in an electrophoretic separation apparatus, and electrophoretic separation media that contains one or more substrates capable of reacting with signal amplification moieties of the electrophoretic tags.

DEFINITIONS

Figure 1A:
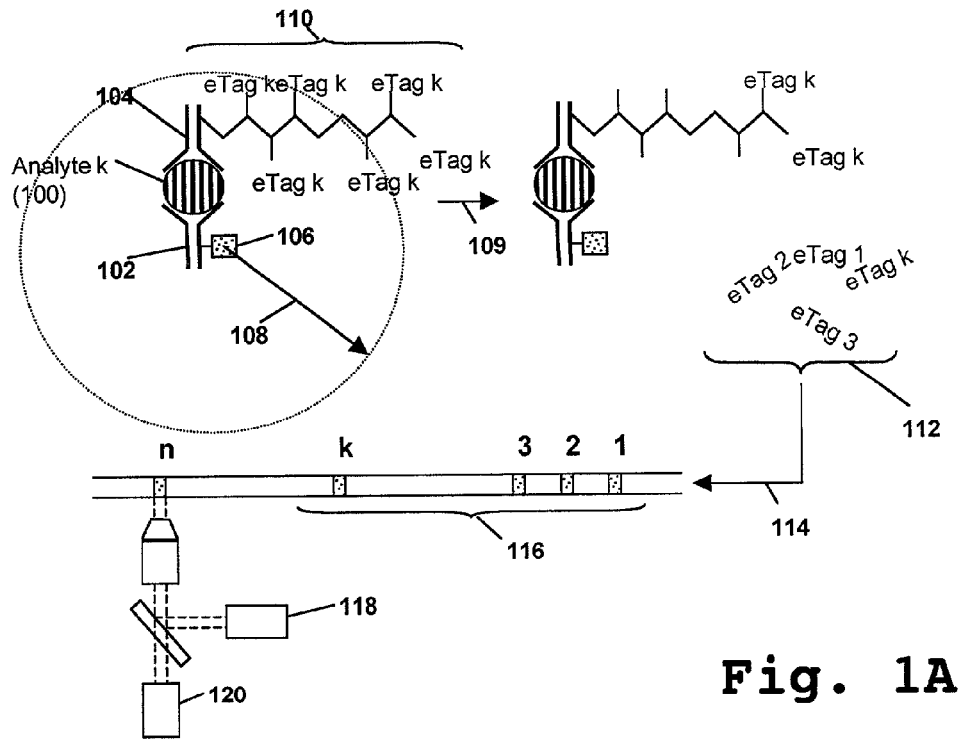
FIG. 1A illustrates how electrophoretic tags may be generated for electrophoretic separation and direct detection.

As used herein, the term "mobility" refers to an amount of movement of one species of molecule relative to another, as a function of defined conditions on a designated separation platform. For separations conducted by electrophoresis, mobility will be the rate of movement under defined electrophoretic conditions, and may be modulated by field strength, salts, sample concentration, etc. Factors that can contribute to electrophoretic mobility include mass, charge, shape, hydrophobicity, affinity for specific molecules, etc. For separations conducted by mass spectrometry, mobility will be the rate of movement, and will be governed by mass. Separations conducted by chromatography may be performed based on a variety of chemical properties, and the mobility of a molecule on such a platform will be determined by the basis of separation. For example, size exclusion chromatography will separate predominantly based on size and/or shape; reverse phase will separate based on solubility; etc.

As used herein, the term "homogeneous" with respect to detection assays refers to assays that do not require (but may include) a separation step.

As used herein, the term "heterogeneous" with respect to detection assays refers to those assays that involve the immobilization of one or more reaction components on a solid support so components remaining in the liquid phase can be easily separated after completion of the hybridization reaction. Hence such assays necessarily involve a separation step. This can be achieved in a variety of ways. Each way requires that a reagent be bound to a solid support that distinguishes between a labeled reagent/target complex versus unbound label. The solid support may be a vessel wall, e.g. microtitre plate well, capillary, plate, slide, beads, including magnetic beads, liposomes, or the like. The primary characteristics of the solid support is that it permits segregation of the bound labeled specific binding member from unbound probe, and that the support does not interfere with the formation of the binding complex, nor the other operations of the determination.

As used herein, the terms "complementary" or "complementarity" refer to an oligonucleotide which, may be aligned with another nucleic acid sequence such that the 5' end of one sequence is paired with the 3' end of the other in an antiparallel orientation. Complementarity need not be perfect and stable duplexes may be obtained using sequences that contain mismatches.

A nucleic acid sequence is considered to "selectively hybridize" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm −5° C. (5° below the Tm of the probe); "high stringency" at about 5-10° below the Tm; "intermediate stringency" at about 10-20° below the Tm of the probe; and "low stringency" at about 20-25° below the Tm. Functionally, maximum stringency conditions may be used to identify sequences having strict identity or near-strict identity with the hybridization probe; while high stringency conditions are used to identify sequences having about 80% or more sequence identity with the probe.

As used herein the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

As used herein, the term "capture ligand" refers to a group that may be included within the tag and is capable of binding specifically to a "capture agent" or receptor. The interaction between such a capture ligand and the corresponding capture agent may be used to separate uncleaved tags from released tags.

As used herein, the terms "signal" and "detectable signal" refer to a physical or chemical property which results when the signal amplification portion of a tag is contacted with an appropriate reagent, such as chemiluminescence, fluorescence or color, which can be detected and measured, either qualitatively or quantitatively.

As used herein, "alkyldiyl" refers to a saturated or unsaturated, branched, straight-chain or cyclic divalent hydrocarbon radical derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyls include, but are not limited to, methandiyl; ethyldiyls such as ethan-1,1-diyl, ethan-1,2-diyl, ethen-1,1-diyl, ethen-1,2-diyl; propyldiyls such as propan-I,I-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop en-1,2-diyl, prop-1-en-1,3-diyl, cycloprop-1-en-1,2-diyl, cycloprop en-1,2-diyl, cycloprop en-I,I-diyl, prop yn-1,3-diyl, etc.; butyldiyls such as, butan-I,I-diyl, butan1,2-diyl, butan-1,3-diyl, butan-1,4-diyl, butan-2,2-diyl, 2-methyl-propan-I,I-diyl, 2-methylpropan-1,2-diyl, cyclobutan-1,1-diyl; cyclobutan-1,2-diyl, cyclobutan-1,3-diyl, but-1-en1,1-diyl, but-1-en-1,2-diyl, but-1-en-1,3-diyl, but-1, -en-1,4-diyl, 2-methyl-prop-1-en-1,17 diyl, 2-methanylidene-propan-I,I-diyl, buta-1,3-dien-I,I-diyl, buta-1,3-dien-1,2-diyl, buta1,3-dien-1,3-diyl, buta-1,3-dien-1,4-diyl, cyclobut-1-en-1,2-diyl, cyclobut-1-en-1,3-diyl, cyclobut en-1,2-diyl, cyclobuta-1,3-dien-1,2-diyl, cyclobuta-1,3-dien-1,3-diyl, but yn1,3-diyl, but yn-1,4-diyl, buta-1,3-diyn-1,4-diyl; and the like.

"Analyte" means a compound or composition to be detected or whose quantity is to be determined. Analytes within the broad concept of the invention include, but are not limited to, nucleic acids, peptides, oligonucleotides, polynucleotides, polypeptides, proteins, epitopes, bacteria, components of biological cells, virtually any molecule detectable by antibodies or other available compounds capable of specific binding reactions with other molecules, and the like.

"Antibody" means an immunoglobulin that specifically binds to, and is thereby defined as complementary with, a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular polypeptide is maintained.

"Antibody binding composition" means a molecule or a complex of molecules that comprise one or more antibodies and derives its binding specificity from an antibody. Antibody binding compositions include, but are not limited to, antibody pairs in which a first antibody binds specifically to a target molecule and a second antibody binds specifically to a constant region of the first antibody; a biotinylated antibody that binds specifically to a target molecule and streptavidin derivatized with moieties such as electrophoretic tags or photosensitizers; antibodies specific for a target molecule and conjugated to a polymer, such as dextran, which, in turn, is derivatized with moieties such as electrophoretic tags or photosensitizers; antibodies specific for a target molecule and conjugated to a bead, or microbead, or other solid phase support, which, in turn, is derivatized with moieties such as electrophoretic tags or photosensitizers, or polymers containing the latter.

"Capillary electrophoresis" means electrophoresis in a capillary tube or in a capillary plate, where the diameter of the separation column or thickness of the separation plate is between about 25-500 microns, allowing efficient heat dissipation throughout the separation medium, with consequently low thermal convection within the medium.

A "sieving matrix" or "sieving medium" means an electrophoresis medium that contains crosslinked or non-crosslinked polymers which are effective to retard electrophoretic migration of charged species through the matrix.

"Specific" in reference to the binding of two molecules or a molecule and a complex of molecules refers to the specific recognition of one for the other and the formation of a stable complex as compared to substantially less recognition of other molecules and the lack of formation of stable complexes with such other molecules. Preferably, "specific" in reference to binding means that to the extent that a molecule forms complexes with other molecules or complexes, it forms at least fifty percent of the complexes with the molecule or complex for which it has specificity. Generally, the molecules or complexes have areas on their surfaces or in cavities giving rise to specific recognition between the two molecules. Exemplary of specific binding are antibody-antigen interactions, enzyme-substrate interactions, polynucleotide interactions, cellular receptor-ligand interactions, and so forth.

As used herein, the term "spectrally resolvable" in reference to a plurality of fluorescent labels means that the fluorescent emission bands of the labels are sufficiently distinct, i.e. sufficiently non-overlapping, that electrophoretic tags to which the respective labels are attached can be distinguished on the basis of the fluorescent signal generated by the respective labels by standard photodetection systems, e.g. employing a system of band pass filters and photomultiplier tubes, or the like, as exemplified by the systems described in U.S. Pat. Nos. 4,230,558, 4,811,218, or the like, or in Wheeless et al, pgs. 21-76, in Flow Cytometry: Instrumentation and Data Analysis (Academic Press, New York, 1985).

The terms "oligonucleotide" or "polynucleotide" as used herein mean linear polymers of natural or modified monomers and/or linkages, including deoxyribonucleosides, ribonucleosides, anomeric forms thereof, peptide nucleic acids (PNAs), and the like, capable of specifically binding to a target polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 3-4, to several tens of monomeric units, e.g. 40-60. Whenever an oligonucleotide or polynucleotide is represented by a sequence of letters, such as "ATGCCTG," it will be understood that the nucleotides are in 5' 3' order from left to right and that "A" denotes deoxyadenosine, "C" denotes deoxycytidine, "G" denotes deoxyguanosine, and "T" denotes thymidine, unless otherwise noted. Usually oligonucleotides or polynucleotides comprise the four natural nucleotides; however, they may also comprise non-natural nucleotide analogs. It is clear to those skilled in the art when oligonucleotides or polynucleotides having natural or non-natural nucleotides may be employed, e.g. where processing by enzymes is called for, usually oligonucleotides consisting of natural nucleotides are required.

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex. Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen bonding.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the only proviso that they are capable of specific hybridization. Such analogs include synthetic nucleosides designed to enhance binding properties, reduce complexity, increase specificity, and the like.

As used herein, "amplicon" means the product of an amplification reaction. That is, it is a population of polynucleotides, usually double stranded, that are replicated from one or more starting sequences. The one or more starting sequences may be one or more copies of the same sequence, or it may be a mixture of different sequences. Preferably, amplicons are produced either in a polymerase chain reaction (PCR) or by replication in a cloning vector.

DETAILED DESCRIPTION OF THE INVENTION

The present invention is directed to compositions and methods for detecting a plurality of analytes. An important aspect of the invention is the use of electrophoretic tags containing at least one signal amplification moiety. Such tags are occasionally referred to herein as "catalytic tags" or "cTags." As described more fully below, such tags may be used in a wide variety of formats.

Figure 1B:
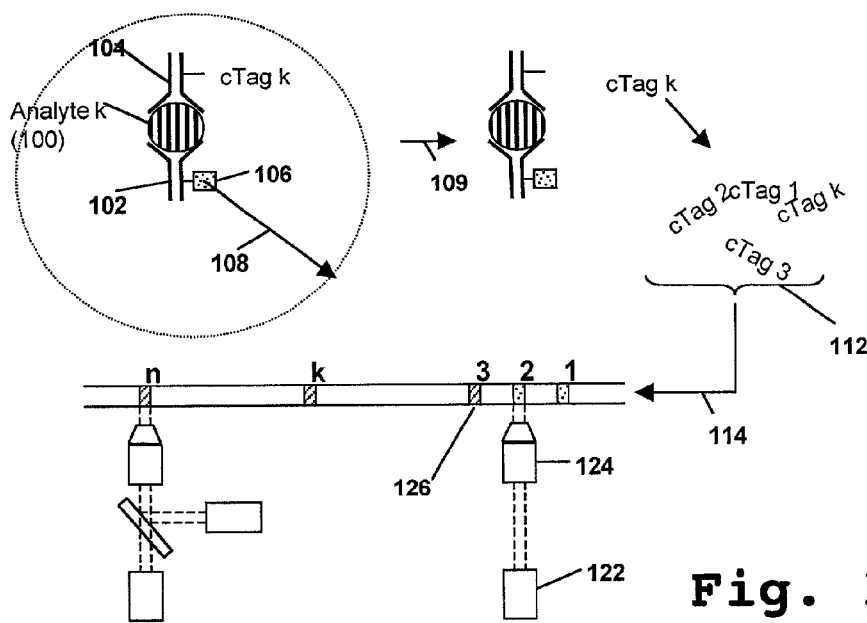
FIG. 1B illustrates how electrophoretic tag of the invention is generated and how after separation its signal amplification moiety is activated to generate a signal.

FIGS. 1A and 1B illustrate two multiplexed assay procedures, one employing electrophoretic tags without a signal amplification moiety (FIG. 1A) and one using electrophoretic tags with a signal amplification moiety (FIG. 1B). The advantage of the latter approach is that assay sensitivity relies only partially on the initial cleavage of the electrophoretic tags. Further sensitivity is achieved by signal amplification after the electrophoretic tags are separated. Referring to FIG. 1A, the Kth analyte (100) in a plurality of n analytes in a sample is bound by first binding agent (102), an antibody in this case, having cleavage-inducing moiety (106) attached, which in this case is a photosensitizer. Photosensitizer (106) has an effective proximity (108) within which singlet oxygen generated by it upon photoactivation can cleave the cleavable linkages holding "eTags" (110) onto second binding agent (104). After photoactivation (109), eTags within effective proximity (108) are released along with eTags from other binding complexes to form mixture (112) which is introduced (114) into a electrophoretic separation apparatus and separated into distinct bands (116). Separated tags are detected using conventional detection methodologies. For example, if the eTags carry fluorescent labels, then detection occurs after illumination by light source (120) and collection of fluorescense by detector (118). In FIG. 1B the process is identical, except that after introduction (114) into the electrophoretic apparatus, the cTags are activated to react with a substrate in the electrophoretic separation medium and to generate a detectable product (126). Detectable product (126) is then detected at a detection station as described for FIG. 1A. As used herein, "substate" means any compound that reacts or interacts with an electrophoretic tag to cause the generation of a detectable product. Substrates include, but are not limited to, leuco dyes, enzyme co-factors, and the like, as described more fully below. Preferably, substrates are leuco dyes and the signal amplification moiety of the electrophoretic tag is a photosensitizer.

Figure 2A:
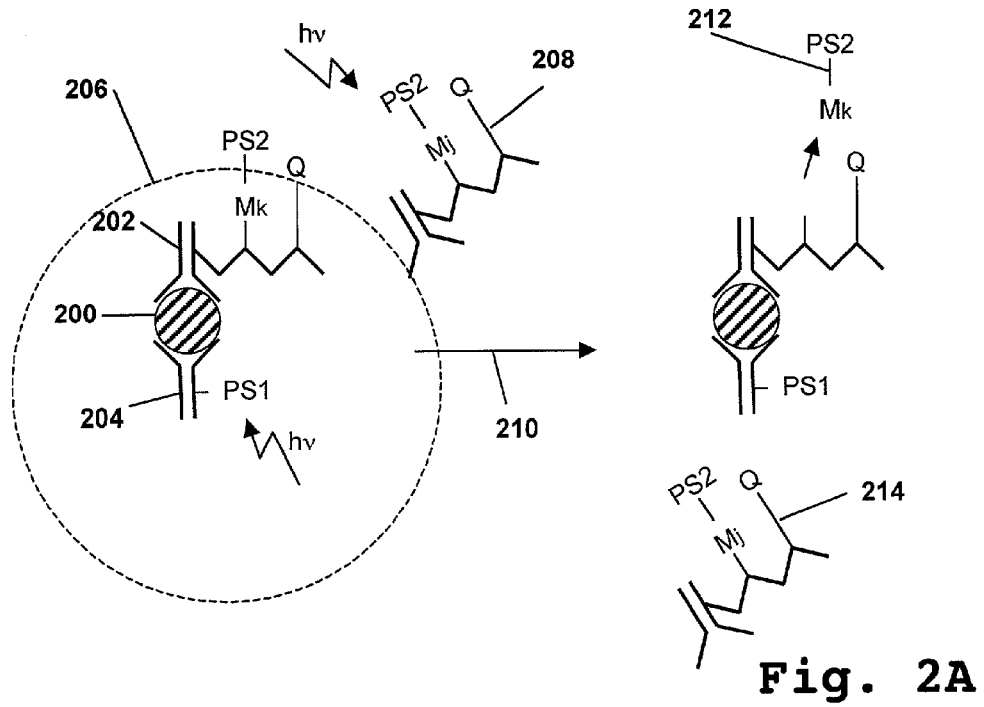
FIGS. 2A-E illustrate various embodiments of the invention for detecting polynucleotide and non-polynucleotide analytes.
Figure 2B:
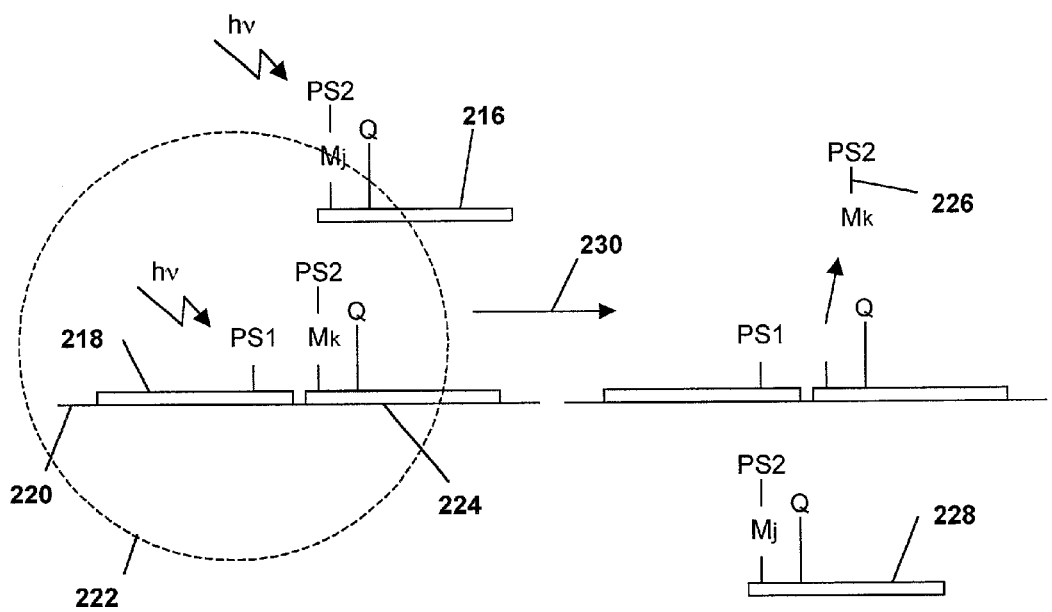

FIG. 2A illustrates another embodiment of the invention which uses antibodies as both the first and second binding agents. Analyte (200) is bound by first binding agent (204) having photosensitizer ($PS_1$) and second binding agent (202) that has an electrophoretic tag consisting of a second photosensitizer ($PS_2$) and mobility modifying moiety ($M_k$). Second binding agent also has quencher (Q) adjacent to and quenching photosensitizer ($PS_2$). Adjacent quencher (Q) prevents $PS_2$ from being photoactivated to produce singlet oxygen, which in the unbound state (208) would result in self-cleavage and lead to spurious assay results. That is, $PS_2$ is in an inactive state when adjacent to the quencher. When within effective proximity (206) of $PS_1$, cTag (212) is cleaved, after which it is separated and activated as shown in FIG. 1B. FIG. 2B illustrates a similar assay configuration wherein the first (218) and second (224) binding agents are oligonucleotides. Another embodiment involving nucleic acid analytes and binding agents is illustrated in FIG. 2D. Spurious activation of unbound photosensitizer (PS) is prevented by quencher (Q) which is held adjacent to photosensitizer (PS) by hairpin (252). When hairpin (252) hybridizes (256) to analyte (254) in a "taqman" type of assay, a polymerase (258) having 5'→3' exonuclease activity cleaves the cTag, which consists of photosensitizer (PS), mobility modifying moiety (M), and a portion of digested hairpin (252). In accordance with such assay, the method provides: (a) contacting a sample comprising single-stranded nucleic acids (254) with an oligonucleotide (252) containing a sequence complementary to a region of the target nucleic acid and a labeled oligonucleotide containing a sequence complementary to a second region of the same target nucleic acid sequence strand, but not including the nucleic acid sequence defined by the first oligonucleotide, to create a mixture of duplexes during hybridization conditions, wherein the duplexes comprise the target nucleic acid annealed to the first oligonucleotide and to the labeled oligonucleotide such that the 3' end of the first oligonucleotide is upstream of the 5' end of the labeled oligonucleotide; (b) maintaining the mixture of step (a) with a template-dependent nucleic acid polymerase having a 5' to 3' nuclease activity under conditions sufficient to permit the 5' to 3' nuclease activity of the polymerase to cleave the annealed, labeled oligonucleotide and release cTags; and (c) detecting and/or measuring the released of cTags.

Figure 2C:
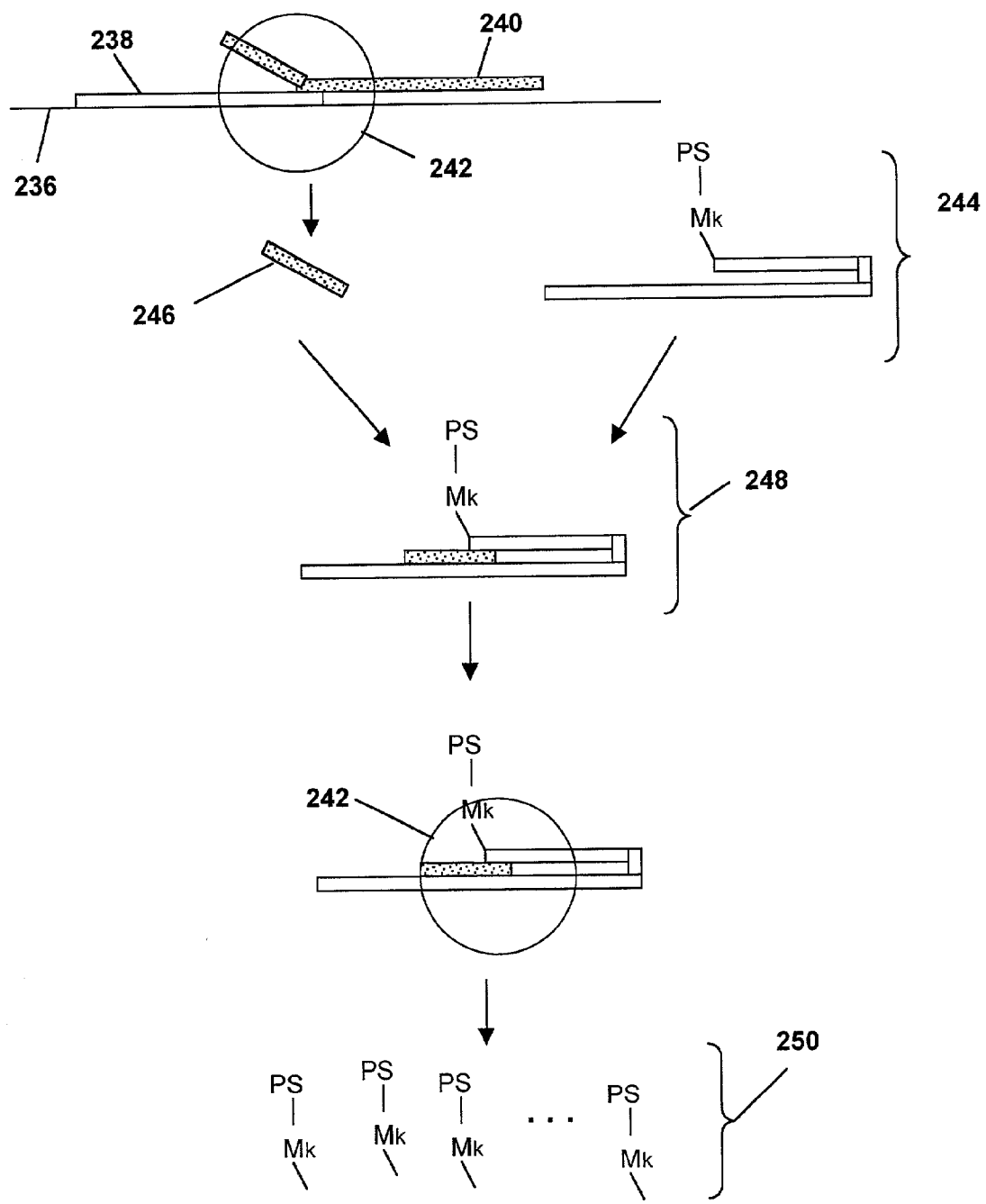
Figure 2D:
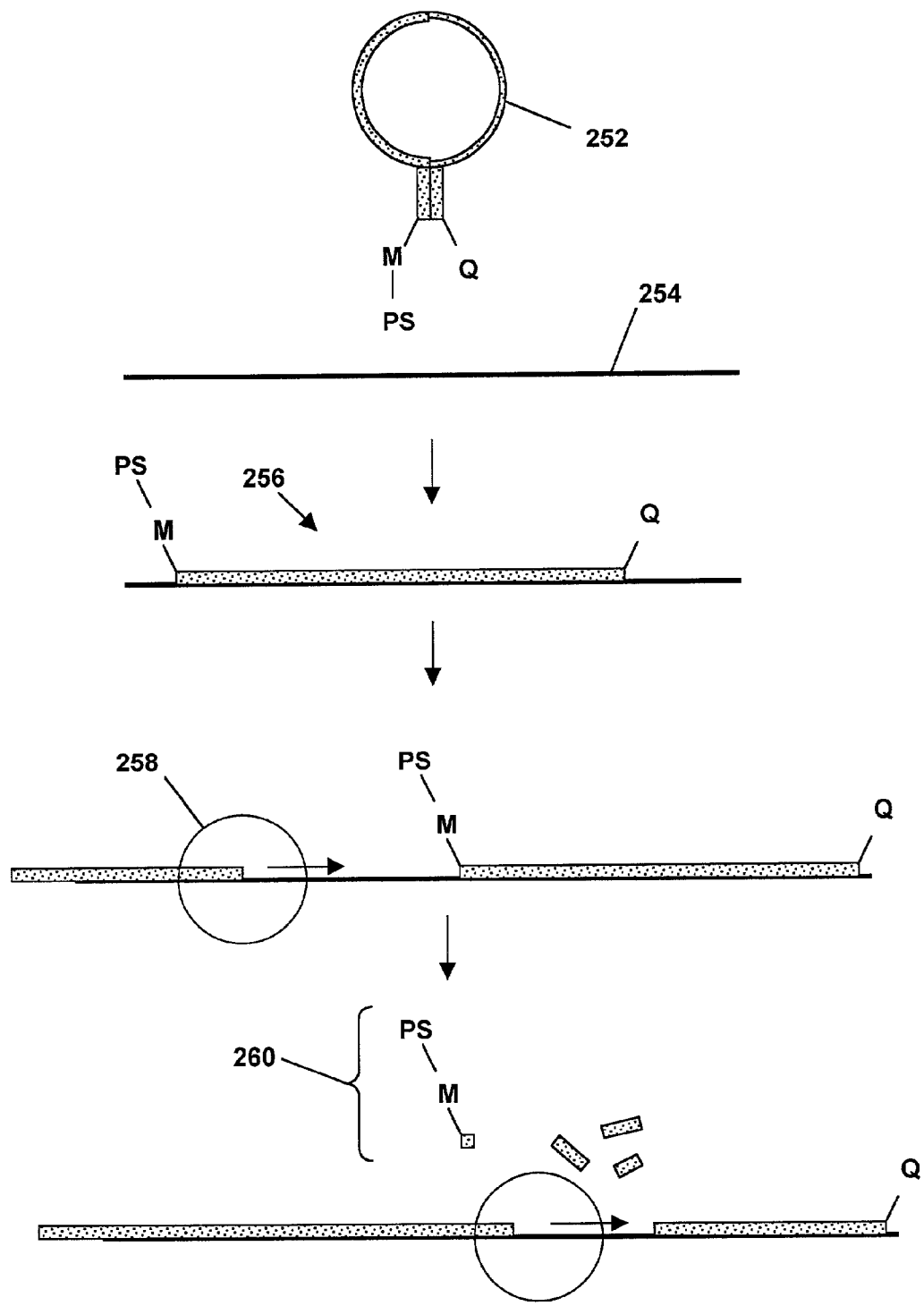

FIG. 2C illustrates the use of cTags in a cleavase-based (Invader) assay. In accordance with such assay, the method provides: i) a cleavage means (242), ii) a source of target nucleic acid, said target nucleic (236) acid having a first region, a second region and a third region, wherein said first region is downstream from said second region and wherein said second region is contiguous to and downstream from said third region; iii) first (240) and second (238) oligonucleotides having 3' and 5' portions, wherein said 3' portion of said first oligonucleotide contains a sequence complementary to said third region of said target nucleic acid and wherein said 5' portion of said first oligonucleotide and said 3' portion of said second oligonucleotide each contain sequence fully complementary to said second region of said target nucleic acid, and wherein said 5' portion of said second oligontcleotide contains sequence complementary to said first region of said target nucleic acid; b) mixing said cleavage means, said target nucleic acid, said first oligonucleotide and said second oligonucleotide to create a reaction mixture under reaction conditions such that at least said 3' portion of said first oligonucleotide is annealed to said target nucleic acid and wherein at least said 5' portion of said second oligonucleotide is annealed to said target nucleic acid so as to create a cleavage structure and wherein the combined melting temperature of said complementary regions within said 5' and 3' portions of said first oligonucleotide when annealed to said target nucleic acid is greater than the melting temperature of said 3' portion of said first oligonucleotide, and wherein cleavage of said cleavage structure occurs to generate non-target cleavage products (246); and c) detecting said non-target cleavage products by repeatedly cleaving electrophoretic tags (Mk)-(PS) from a second cleavage structure (248) using the cleavage means.

Figure 2E:
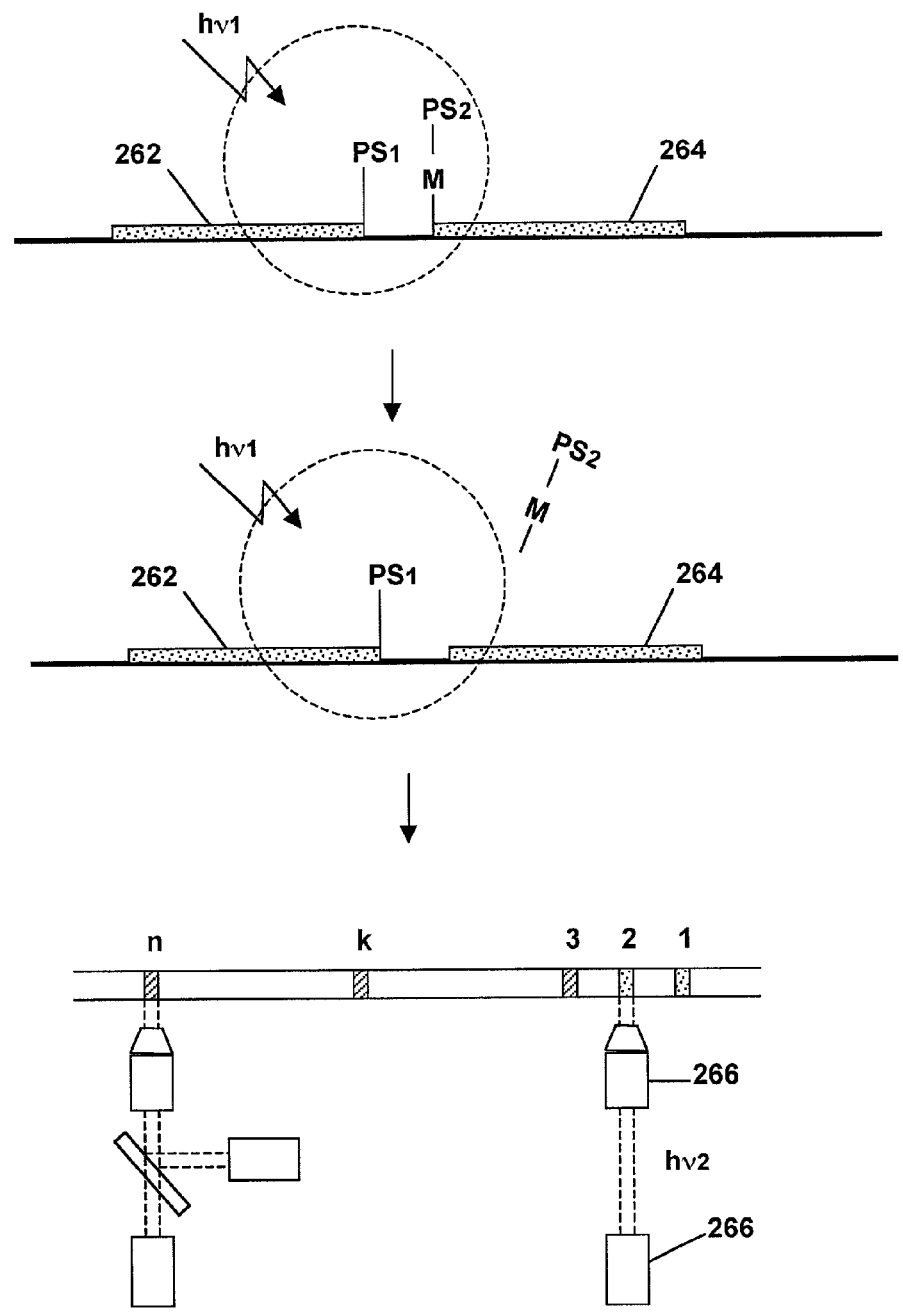

FIG. 2E illustrates a further embodiment in which two photosensitizers are employed, one to cleave the electrophoretic tag during a binding event, and the other (making up part of the tag) to generate a detectable product. In this case, the light absorption frequency of $PS_1$ must be different from that of $PS_2$. After the first cleavage, the released cTags are separated and processed as illustrated in FIG. 1B.

An important feature of the invention is the signal amplification moiety attached to the electrophoretic tags. Signal amplification moiety will also be referred to herein as a "catalytic group" or "catalyst."

A catalytic group for use in practicing the present invention participates as a catalyst, under selected reaction conditions in the presence of one or more reagents, in a reaction generating a detectable product. Besides the nature of the cleavable linking group and/or separation group, the chemical or other characteristics of the catalytic group can be exploited to increase the diversity of the catalytic tag probe sets of the invention.

The catalytic group may include, for example: (i) a sensitizer effective to generate singlet oxygen in the presence of light, and the reacting step includes mixing c-tag reporters with a leucodye that is converted by singlet oxygen to a detectable product, (ii) a cofactor, that with an enzyme can generate a active enzyme, e.g., heme with peroxidase, and the reacting step includes mixing the c-tag reporters with a peroxidase enzyme capable of oxidizing a leucodye to a detectable product in the presence of $H_2O_2$, (iii) a complementing molecule, e.g., a polypeptide required for the assembly of inactive subunits into an active, multi-subunit enzyme, or (iv) a nucleic acid template that serves as a template for any of a number of DNA amplification reactions, such as, e.g., PCR or rolling circle replication.

Leucodyes as Substrates

In one aspect, signal amplification moieties of the invention convert non-fluorescent, so-called "leuco dyes" into fluorescent, detectable products. Preferably, conversion is effected by an oxidization reaction driven by the production of singlet oxygen by a signal amplification moiety. In a preferred embodiment, one or more leuco dyes are substrates (as the term is used herein) for signal amplification moieties. Signal amplification moieties are preferably photosensitizers that oxidize one or more leuco dyes in an electrophoretic separation medium, as illustrated in FIG. 1B, to produce detectable products, i.e. amplified signals. The use of leuco dyes in analytical technology and in industry is well known, e.g. Muthyala, Editor, Chemistry and Applications of Leuco Dyes (Plenum, New York, 1997); McCapra, U.S. Pat. No. 5,516,636.

Fluorescein, rhodamine and various other dyes can be chemically reduced to colorless, nonfluorescent leucodyes. These "dihydro" derivatives are readily oxidized back to the parent dye by certain reactive oxygen species and thus can serve as fluorogenic probes for detecting oxidative activity in cells and tissues (LeBel CP et al., Chem. Res. Toxicol. 5, 227-231, 1992). In one aspect of the invention, a photosensitizer is activated to generate singlet oxygen that will oxidize a leucodye to form a fluorescent dye, e.g., oxidation of dihydrofluorescein to form fluorescein, which may be detected by irradiation at 488 nm. Exemplary fluorescein derivatives that may be used in practicing the methods of the invention include, but are not limited to 5-(pentafluorobenzoylamino)dihydrofluorescein (PFB-$H_2F$); 5-(and-6)-carboxy-2',7'-dichlorodihydrofluorescein (carboxy-$H_2DCF$); 6-carboxy-2',7'-dichlorodihydrofluorescein, 5 (and-6)-carboxy-2',7'-difluorodihydrofluorescein (carboxy-$H_2DFF$); 5-(and-6)-chloromethyl-2', 7'-dichlorodihydrofluorescein (CM-H2DCF); 2',7'-dichlorodihydrofluorescein ($H_2DCF$); 2',4,5,6,7,7'-hexafluorodihydrofluorescein ($H_2HFF$); or 5-(pentafluorobenzoylamino) dihydrofluorescein (PFB-$H_2F$). Exemplary rhodamine derivatives that may be used in practicing the methods of the invention include, but are not limited to dihydrorhodamine 123; dihydrorhodamine 6G.

In a related approach, a thioxene derivative may react with singlet oxygen, generating chemiluminescence at 370 nm. This energy may then be immediately transferred to fluorescent acceptors, shifting the emission wavelength to 520-620 nm.

A preferred leuco dye for use with the invention is leuco fluorescein which is converted by singlet oxygen oxidation to fluorescein. Preferably, methylene blue is employed as a second photosensitizer on a cTag to generate singlet oxygen after electrophoretic separation.

Redox Agents as Enzyme Cofactors

In a further aspect of the invention, the catalytic tag includes a catalytic group that is a cofactor to an oxidation-reduction (redox) enzyme capable of electrochemically converting a substrate into a detectable product. Three major classes of redox enzymes are contemplated, each utilizing a characteristic cofactor. These include 1) cytochromes, requiring an iron-porphyrin prosthetic group such as heme, 2) pyridine-linked dehydrogenases, which catalyze electron transfer between substrates and the loosely-bound coenzymes $NAD^+$/NADH or $NADP^+$/NADPH, and 3) flavin-linked dehydrogenases containing tightly-bound FMN or FAD, and often a metal ion.

An example of the cytochrome class for use in practicing the invention is heme, which is a required cofactor of horseradish peroxidase (HRP). As such, heme may serve as the catalytic group of a c-tag reporter. HRP in the presence of hydrogen peroxide will oxidize a leucodye to produce a fluorescent signal. Another example of an enzyme requiring heme as a cofactor is catalase. The catalase/heme complex generates oxygen radicals from hydrogen peroxide, which in turn will oxidize a leucodye to produce a fluorescent signal. For applications using either HRP or catalase, heme will be modified to produce derivatives with different charges and/or masses in order to generate separable c-tag reporters from a multiplexed reaction. Apoenzyme lacking the cofactor will be present in the separation medium, along with all required substrates for the reaction. Binding of the cofactor catalytic group of the c-tag reporter generates an active holoenzyme.

Examples of pyridine cofactors for use in practicing the reaction include nicotinamide adenine dinucleotide (NAD/H) and nicotinamide adenine dinucleotide phosphate (NADP/H). One or the other of these coenzymes is required for the activity of members of a large class of enzymes called dehydrogenases. Pyridine cofactors are more properly considered as substrates for their corresponding dehydrogenase, as they are loosely bound by the enzyme and are not re-oxidized by the enzyme after being reduced in a reaction cycle. Signal amplification systems utilizing pyridine cofactors as the catalytic group of a c-tag reporter will therefore require a regenerating system for re-oxidation of the cofactor after release from their associated enzyme. This cyclic release, however, is advantageous in practice of the invention because the enzyme's impact on the mobility of the c-tag reporter is minimized, making simultaneous separation and signal generation more practical. As with the cytochromes, the nicotinamide cofactors will be modified to produce derivatives with different charges and/or masses, and a dehydrogenase enzyme and all other required components for the reaction will be included in the separation medium.

A third class of cofactors involved in enzymatic redox reactions is the flavins, including flavin mononucleotide (FMN/$H_2$) and flavin adenine dinucleotide (FAD/$H_2$). The flavin-linked oxidases are readily re-oxidized by artificial electron acceptors, including reducible dyes such as methylene blue, pheazine methosulfate, or 2,6-dichlorophenolindophenol, causing changes in their absorption spectra.

Peptide Complementation

In another aspect of the invention, the catalytic tag comprises a catalytic group, C, that functions as a complementing polypeptide, e.g., a polypeptide required in association with another polypeptide to generate an active enzyme. One exemplary application of the invention makes use of complementing subunit fragments of the multi-subunit enzyme is β-galactosidase. β-galactosidase is a tetrameric enzyme. The gene for this enzyme has been split into two complementing fragments—the short N-terminal fragment, or α-complementation region, and the remaining C-terminal portion called the enzyme acceptor. The α region is required for assembly of inactive subunits of the C-terminal portion into an active, multi-subunit enzyme. When this method is applied to target recognition, the recognition event leads to release of a c-tag reporter from a c-tag probe, wherein the catalytic group of the reporter comprises the α region. This region will be modified to produce derivatives with different charges and/or masses in order to generate separable c-tag reporters from a multiplexed reaction. The C-terminal "acceptor" fragment is provided in the separation medium, along with an appropriate substrate, e.g., chlorophenol-red-β-D-galacto-pyranoside (CPRG), which after cleavage by the enzyme yields chlorophenol red (CPR), which emits light at 570 nm.

Cleavage-Inducing Moiety

In one aspect, particularly when analytes are polynucleotides, a cleavage-inducing moiety may be an enzyme, such as cleavase, or a DNA polymerase with 5'→3' nuclease activity. In another aspect, particularly when analytes are proteins and binding agents are antibodies, a cleavage-inducing moiety is a group that produces an active species that is capable of cleaving a cleavable linkage, preferably by oxidation. Preferably, the active species is a chemical species that exhibits short-lived activity so that its cleavage-inducing effects are only in the proximity of the site of its generation. Either the active species is inherently short lived, so that it will not create significant background because beyond the proximity of its creation, or a scavenger is employed that efficiently scavenges the active species, so that it is not available to react with cleavable linkages beyond a short distance from the site of its generation. Illustrative active species include singlet oxygen, hydrogen peroxide, NADH, and hydroxyl radicals, phenoxy radical, superoxide, and the like. Illustrative quenchers for active species that cause oxidation include polyenes, carotenoids, vitamin E, vitamin C, amino acid-pyrrole N-conjugates of tyrosine, histidine, and glutathione, and the like, e.g. Beutner et al, Meth. Enzymol., 319: 226-241 (2000).

An important consideration for the cleavage-inducing moiety and the cleavable linkage is that they not be so far removed from one another when bound to a target protein that the active species generated by the sensitizer diffuses and loses its activity before it can interact with the cleavable linkage. Accordingly, a cleavable linkage preferably are within 1000 nm, preferably 20-100 nm of a bound cleavage-inducing moiety. This effective range of a cleavage-inducing moiety is referred to herein as its "effective proximity."

Generators of active species include enzymes, such as oxidases, such as glucose oxidase, xanthene oxidase, D-amino acid oxidase, NADH-FMN oxidoreductase, galactose oxidase, glyceryl phosphate oxidase, sarcosine oxidase, choline oxidase and alcohol oxidase, that produce hydrogen peroxide, horse radish peroxidase, that produces hydroxyl radical, various dehydrogenases that produce NADH or NADPH, urease that produces ammonia to create a high local pH. One cleavable linkage can be based on the oxidation of sulfur or selenium, where a thioether, sulfoxide, or selenium analog thereof, is present at the α- or β-position in relation to an activating group, which makes the hydrogen α to the activating group acidic and capable of being removed by base, so as to release the oxidized functionality to which is attached the releasable portion of the e-tag, or to be subject to oxidation with release of the e-tag. Alternatively, one may use metal chelates that are stable at one oxidation state and unstable at another oxidation state. Other compounds include α-substituted methylquinones, which have the releasable portion of a reagent bonded through a leaving group, such as sulfonyl, oxy, amino, etc.

A sensitizer is a molecule, usually a compound, that can be induced to generate a reactive intermediate, or species, usually singlet oxygen. Preferably, a sensitizer used in accordance with the invention is a photosensitizer. However, other sensitizers can be employed in the present invention such as, for example, chemi-activated (e.g., enzymes and metal salts) including, by way of example and not limitation, other substances and compositions that can produce singlet oxygen with or, less preferably, without activation by an external light source. Thus, for example, molybdate ($MoO_4^=$) salts and chloroperoxidase and myeloperoxidase plus bromide or chloride ion have been shown to catalyze the conversion of hydrogen peroxide to singlet oxygen and water. For the above examples of sensitizers, hydrogen peroxide may be included as an ancillary reagent, chloroperoxidase may be bound to a surface and molybdate may be incorporated in the aqueous phase of a liposome, respectively. Other sensitizers included within the scope of the invention are compounds that are not true sensitizers but which on excitation by heat, light, ionizing radiation, or chemical activation will release a molecule of singlet oxygen. The best known members of this class of compounds include the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen. Further sensitizers are disclosed in the following references: Di Mascio et al, FEBS Lett., 355: 287 (1994) (peroxidases and oxygenases); Kanofsky, J.Biol. Chem. 258: 5991-5993 (1983) (lactoperoxidase); Pierlot et al, Meth. Enzymol., 319: 3-20 (2000) (thermal lysis of endoperoxides); and the like.

Attachment of a binding agent to the cleavage-inducing moiety may be direct or indirect, covalent or non-covalent and can be accomplished by well-known techniques, commonly available in the literature. See, for example, "Immobilized Enzymes," Ichiro Chibata, Halsted Press, New York (1978); Cuatrecasas, J. Biol. Chem., 245:3059 (1970). A wide variety of functional groups are available or can be incorporated. Functional groups include carboxylic acids, aldehydes, amino groups, cyano groups, ethylene groups, hydroxyl groups, mercapto groups, and the like. The manner of linking a wide variety of compounds is well known and is amply illustrated in the literature (see above). The length of a linking group to a binding agent may vary widely, depending upon the nature of the compound being linked, the effect of the distance on the specific binding properties and the like.

Lectins may be attached to the cleavage-inducing moiety by known covalent bonding techniques. Such binding is suitably performed by cross-linking the lectin with the cleavage-inducing moiety or a hub molecule through a bifunctional cross-linking agent. Suitable bifunctional compounds are found in Review by Peters, K. and Richards, F. M., (Ann. Rev. Biochim. 46 (1977) 523). Alkyl imidates show a high degree of specificity among the functional groups presented to them by a protein. The reaction is specific for primary amino groups. Specific coupling reagents include amidoesters such as dimethyl malonimidate, azides such as the acryl azide of tartryl diazide which reacts readily with amino groups to produce amidelinkages, aryl dihalides (e.g., 1,5-difluoro-2,4-dinitrobenzene, or 4,4'-difluoro-3,3'-dinitrophenyl sulfone), glutaraldehyde, dimaleimide, mixed anhydride, mixed aromatic or aliphatic dicarboxyl, N-hydroxysuccinimide ester, and other known cross-linking agents. Catalytic reagents such as 1-ethyl-3(3-dimethylamino propyl)carbodiimide hydrochloride may be used to form covalent bonds between amino groups of one molecule to carboxyl groups of another.

The first binding reagent may be preformed or formed in situ. In the former circumstance the first binding reagent has all of its components bound together prior to use in the present methods. In the latter situation at least some of the components of the first binding reagent are added separately to a medium in which the present methods are conducted. In one approach the binding agent comprises a moiety for attachment of the cleavage-inducing moiety. Usually, this involves a second moiety, which is present on the cleavage-inducing moiety, where the second moiety and the moiety of the binding agent interact providing for attachment of the cleavage-inducing moiety to the binding agent and formation of the first binding reagent in situ. Typically, the moieties interact by non-covalent attachment. This situation is exemplified by one of the two moieties comprising a small molecule (about 100 to about 1500 molecular weight) and the other of the moieties comprising a binding partner for the small molecule. For example, the small molecule may be biotin, digoxin, fluorescein, dinitrophenol, and so forth, and the binding partner for the small molecule is, respectively, avidin, antibody for digoxin, antibody for fluorescein, antibody for dinitrophenol, and so forth.

It may be desirable to have multiple cleavage-inducing moieties attached to a binding agent to increase, for example, the number of active species generated. In one approach the binding agent has a plurality of sites for attachment such as, for example, an antibody, a lectin, and so forth. To further enhance the number of cleavage-inducing moieties, a hub molecule or nucleus is employed. The hub nucleus is a polyfunctional material, normally polymeric, having a plurality of functional groups, e.g., hydroxy, amino, mercapto, carboxy, ethylenic, aldehyde, etc., as sites for linking. The functionalities on the hub should be those that are reactive with a functionality on the cleavage-inducing moiety or the binding agent to be attached. A discussion of hub nuclei is set forth below with respect to other reagents and the principles discussed below may be applied in this instance as well.

In certain embodiments the first binding reagent comprises a support with which one of the components of the first binding reagent is associated. The support may be comprised of an organic or inorganic, solid or fluid, water insoluble material, which may be transparent or partially transparent. The support can have any of a number of shapes, such as particle including bead, film, membrane, tube, well, strip, rod, and the like. For supports in which photosensitizer is incorporated, the surface of the support is, preferably, hydrophilic or capable of being rendered hydrophilic and the body of the support is, preferably, hydrophobic. The support may be suspendable in the medium in which it is employed. Examples of suspendable supports, by way of illustration and not limitation, are polymeric materials such as latex, lipid bilayers, oil droplets, cells and hydrogels. Other support compositions include glass, metals, polymers, such as nitrocellulose, cellulose acetate, poly (vinyl chloride), polyacrylamide, polyacrylate, polyethylene, polypropylene, poly(4-methylbutene), polystyrene, polymethacrylate, poly(ethylene terephthalate), nylon, poly (vinyl butyrate), etc.; either used by themselves or in conjunction with other materials. Attachment of binding agents to the support may be direct or indirect, covalent or non-covalent and can be accomplished by well-known techniques, commonly available in the literature as discussed above. See, for example, "Immobilized Enzymes," Ichiro Chibata, supra. The surface of the support will usually be polyfunctional or be capable of being polyfunctionalized or be capable of binding to a target-second binding agent, or the like, through covalent or specific or non-specific non-covalent interactions.

The cleavage-inducing moiety may be associated with the support by being covalently or non-covalently attached to the surface of the support or incorporated into the body of the support. Linking to the surface may be accomplished as discussed above. The cleavage-inducing moiety may be incorporated into the body of the support either during or after the preparation of the support. In general, the cleavage-inducing moiety is associated with the support in an amount necessary to achieve the necessary amount of active species. Generally, the amount of cleavage-inducing moiety is determined empirically.

The catalytic and separation groups may be linked to the target-binding member by a bond that is thermally, photolytically or chemically cleavable. Numerous linkages are available. See, for example, U.S. Pat. No. 5,721,099. There is an interest in cleaving the catalytic group component of the catalytic tag from the target-binding member in situations where cleavage of the target-binding member can occur at more than one position, resulting in satellite cleavage products that interfere with the separation and detection of the catalytic tags. However, rather than requiring an additional step in the identification of the tags by releasing them from the target to which they are attached, one can modify the target-binding member to minimize cleavage at other than the desired bond, for example in the case of nucleic acid targets, the ultimate or penultimate phosphate link in a nucleic acid sequence.

The nature of the cleavable linking group may be varied widely. In one aspect, the methods of the invention include the use of a selected cleaving agent to cleave an enzyme-cleavable linkage, such as, e.g., (a) a nuclease for cleavage of phosphodiester or other nuclease-cleavable intersubunit linkage between two nucleotide subunits; (b) a peptidase for cleavage of a peptide linkage; (c) an esterase for cleavage of an ester linkage; and (d) an oligosaccharide hydrolase for cleavage of oligosaccharide.

In a related aspect, the invention provides an active species that is short-lived and able to act upon a cleavable linkage and release the c-tag reporter. The catalytic tag probe and appropriate reagent(s) are brought into close proximity as a result of the presence of a particular target, enabling the short-lived species to cleave the cleavable linkage. In the absence of target, the two reagents are not in close proximity to any significant amount, and thus the short-lived active species, when generated, will cleave the linking group of the c-tag probe. Preferred cleaving agents include, but are not limited to singlet oxygen, $H_2O_2$, and redox reagents.

In one preferred embodiment of the invention a sensitizer reagent capable of generating singlet oxygen is brought in close proximity to the cleavable linkage of the catalytic tag probe, wherein said linkage is susceptible to cleavage by oxidation. When the sensitizer reagent is activated to generate singlet oxygen, if the target is present, the singlet oxygen is able to release the releasable portion of the catalytic tag probe (designated the catalytic tag reporter), which can be detected and/or quantified. The presence and/or amount of the catalytic tag reporter indicate the presence and/or amount of the target in the sample.

There are a large number of different functional entities that are stable under the conditions used for the binding event with the binding compound and may then be cleaved without affecting adversely the catalytic tag reporter. Functional entities may be cleaved by chemical or physical methods, involving oxidation, reduction, solvolysis, e.g. hydrolysis, photolysis, thermolysis, electrolysis, chemical substitution, etc. Specific functional entities include thio ethers that may be cleaved with singlet oxygen, disulfide that may be cleaved with a thiol, diketones that may be cleaved by permanganate or osmium tetroxide, β-sulfones, tetraalkylammonium, trialkylsulfonium, tetraalkylphosphonium, etc., where the α-carbon is activated with carbonyl, nitro, etc., that may be cleaved with base, quinones where elimination occurs with reduction, substituted benzyl ethers that can be cleaved photolytically, carbonates that can be cleaved thermally, metal chelates, where the ligands can be displaced with a higher affinity ligand, as well as many other functional entities that are known in the literature. Cleavage protocols are described in U.S. Pat. Nos. 5,789,172 and 6,001,579 and references cited therein.

There are a number of genetic analyses that involve cleavage of a phosphate bond of a nucleic acid sequence as a result of hybridization. For the most part, the initial step will be in solution, although one may have one or more reagents bound to a solid support in the first and succeeding stages of the determination. One technique is described in U.S. Pat. Nos. 5,876,930 and 5,723,591, where a primer and a probe are bound to a target sequence and by extending the primer with a DNA polymerase having 5'-3' nuclease activity, the terminal nucleotides are cleaved as the polymerase processes along the target DNA. By having a catalytic tag reporter bonded to the terminal and/or internal nucleotide(s), the catalytic tag reporter will be released when the target nucleic acid is present. Another technique employs an enzyme referred to as a cleavase, which recognizes a three-member complex of the target nucleic acid, a primer and a probe. See U.S. Pat. No. 5,719,028. Attached to the terminus of the probe is a catalytic tag reporter that is released by the cleavase, where a three-membered complex is formed.

Where detachment of the product from all or a portion of the target-binding member is desired, there are numerous functionalities and reactants, which may be used. Conveniently, ethers may be used, where substituted benzyl ether or derivatives thereof, e.g. benzhydryl ether, indanyl ether, etc. may be cleaved by acidic or mild reductive conditions. Alternatively, one may employ beta-elimination, where a mild base may serve to release the product. Acetals, including the thio analogs thereof, may be employed, where mild acid, particularly in the presence of a capturing carbonyl compound, may be employed. By combining formaldehyde, HCl and an alcohol moiety, a α-chloroether is formed. This may then be coupled with a hydroxy functionality to form the acetal. Various photolabile linking groups may be employed, such as o-nitrobenzyl, 7-nitroindanyl, 2-nitrobenzhydryl ethers or esters, etc.

For a list of cleavable linking groups, see, for example, Greene and Wuts, Protective Groups in Organic Synthesis, 2nd ed. Wiley, 1991. The versatility of the various systems that have been developed allows for broad variation in the conditions for attachment of the catalytic tag entities.

Various functionalities for cleavage are illustrated by: silyl groups being cleaved with fluoride, oxidation, acid, bromine or chlorine; o-nitrobenzyl with light; catechols with cerium salts; olefins with ozone, permanganate or osmium tetroxide; sulfides with singlet oxygen or enzyme catalyzed oxidative cleavage with hydrogen peroxide, where the resulting sulfone can undergo elimination; furans with oxygen or bromine in methanol; tertiary alcohols with acid; ketals and acetals with acid; α- and β-substituted ethers and esters with base, where the substituent is an electron withdrawing group, e.g., sulfone, sulfoxide, ketone, etc., and the like.

Capture Agents

In certain embodiments of the invention, the target-binding member T in each of the catalytic tag probes contains a capture moiety that by itself, or by reaction with a capture agent, is effective to impart to the catalytic tag probe a mobility that prevents undegraded probes from migrating within the range of mobilities of the c-tag reporters chosen for the analysis. This is accomplished with moieties that impart a net positive charge and/or mobility outside the range of mobilities of the expected c-tag reporters, or with moieties that can be bound by a capture agent that similarly imparts a net positive charge and/or mobility outside the range of mobilities of the expected c-tag reporters. Exemplary capture moieties include one component of a receptor/ligand pair, a particle, or a mass group.

Some exemplary molecules that can serve as capture moiety/capture agent pairs include biotin and strept/avidin, antigen and antibody, e.g. digoxin or a derivative thereof and antidigoxin, etc. By having a capture moiety conjugated to the target, one can utilize the capture agent to sequester the catalytic tag probe bound to target, remove unbound probe and then release c-tag reporters from the bound probe. Alternatively, one may bind a capture agent that has an opposite charge to that of the probe/target complex, so that the capture agent-capture moiety complex with intact catalytic tag probe migrates in the opposite direction of the corresponding released c-tag reporter.

In one exemplary use of a capture agent, a catalytic tag probe comprising a nucleotide target-binding sequence is modified to improve separation and detection of the released catalytic tag reporters. By virtue of the difference in mobility based on the separation group, the catalytic tag reporter and the unreacted catalytic tag probes will have different mobilities. In general, unreacted catalytic tag probe molecules are present in larger amounts than released catalytic tag reporters, such that they may obscure detection of the released catalytic tag reporters rendering an additional separation step necessary for adequate separation and later detection.

In one embodiment, negatively charged catalytic tag probe molecules are preferred, since they provide for higher enzymatic activity and decrease capillary wall interaction. Therefore, by providing that a catalytic tag probe comprising a nucleotide target-binding ligand, but not the released catalytic tag reporter, be modified with a positively charged moiety, one can change the electrostatic nature of the catalytic tag probe molecules during the separation. By providing a capture ligand on the catalytic tag probe to which a positively charged molecule (capture agent) can bind, one only need add the positively charged molecule to change the electrostatic nature of the catalytic tag probe.

Conveniently, one will usually have a capture ligand of under about 1 kDa. This may be exemplified by the use of biotin as the capture ligand and avidin, which is highly positively charged, as the capture agent. Desirably, the capture agent is positively charged, naturally as in the case of avidin, or is made so, by the addition of a positively charged moiety or moieties, such as ammonium groups, basic amino acids (such as arginine, lysine or histidine), etc. One may employ pairs, where the capture agent or receptor, e.g., an antibody, is naturally positively charged or is made so by conjugation with one or more positively charged entities. The presence of the positively charged moiety has many advantages in substantially removing unbound catalytic tag probe molecules. Further exemplary capture agents include natural or synthetic receptors, such as immunoglobulins, lectins, enzymes, etc. Avidin is positively charged, while the cleaved catalytic tag reporter is negatively charged.

Thus the separation of the catalytic tag reporters from, not only uncleaved catalytic tag probe, but also its degradation products, is easily achieved by using conventional separation methods. Alternatively, the capture agent may be bound to a solid support or high molecular weight macromolecule, such as a vessel wall, particles, e.g. magnetic particles, cellulose, agarose, etc., and separated by physical separation or centrifugation, dialysis, etc. This aspect of the method further enhances the specificity of the assay and allows for a higher degree of multiplexing.

In one example of this aspect of the invention, the catalytic tag probe includes a capture ligand, exemplified by biotin, attached to the target-binding member portion of a catalytic tag probe, so as to be separated from the catalytic tag reporter following cleavage. In carrying out the separation, following cleavage, a receptor for biotin, e.g., strept/avidin, is added to the assay mixture and serves to separate uncleaved catalytic tag probes and degradation products thereof from catalytic tag reporters.

For catalytic tag probes containing nucleic acid target-binding moieties, one preferred embodiment includes a blocking linkage between nucleotides in the nucleic acid sequence of the target-binding member, particularly at least one of the links between the second to fourth nucleotides to inhibit cleavage at this or subsequent sites. Another preferred aspect of the invention includes the use of control sequences for quantitation of target.

In some cases, the capture ligand may be present at a position other than the penultimate position and one may make the ultimate linkage nuclease resistant, such that cleavage is directed to the penultimate linkage.

For a homogeneous assay, the sample is combined with one or more catalytic tag probes and ancillary reagents in a solution-phase reaction mixture supporting the cleavage of the cleavable linking groups. The mixture may then be processed to separate the catalytic tag reporters from the other components of the mixture. The mixture, with or without catalytic tag reporter enrichment is then transferred to a separation device, usually a microfluidic or capillary electrophoresis device and the medium modified as required for the separation. Where one wishes to remove from the separation channel intact catalytic tag probe molecules, a capture ligand for binding to a capture agent is bound to the catalytic tag probe that is not released when the catalytic tag reporter is released. Alternatively, by adding a capture agent that has the opposite charge of the catalytic tag reporter, such that the overall charge will be opposite to the charge of the catalytic tag reporter, the molecules bound to the capture agent will migrate toward the opposite electrode from the released catalytic tag reporter molecules. For example, one could use biotin and streptavidin, where streptavidin carries a positive charge. In a nucleic acid probe wherein cleavage occurs between two nucleotides, the biotin may be bonded to at least the nucleotide adjacent to the site of cleavage and on the opposite side of the catalytic group. When cleavage occurs between the two nucleotides resulting in release of a catalytic tag reporter, the terminal nucleotide of the cleaved probe oligonucleotide is labeled with a biotin, while the catalytic tag reporter is released without the biotinylated nucleotide. In the case of a peptide analyte, one may construct the catalytic tag probe such that the capture ligand will remain with the untagged peptide cleavage product of the probe. For example, one could provide a capture ligand with a substitution for the methyl group of methionine. Using the pyrazolone of the modified methionine, one could bond to an available lysine. The amino group of the pyrazolone would be substituted with biotin. Cleavage would then be achieved with cyanogen bromide, releasing the catalytic tag reporter, but the biotin would remain with the peptide and any catalytic tag probe that was not released from the capture agent. Avidin is then used to change the polarity or sequester the catalytic tag probe conjugated to the capture ligand.

Photosensitizers as Cleavage-Inducing Moieties and Signal Amplification Moieties In the invention, photosensitizers are preferred as both cleavage-inducing moieties and signal amplification moieties. More preferably, a first photosensitizer acts as a cleavage-inducing moiety to release an electrophoretic tag that itself includes a second photosensitizer in inactivated form, either being held adjacent to a quencher or being chemically inactive until an oxidizing reaction converts it into an active form.

As mentioned above, the preferred cleavage-inducing moiety in accordance with the present invention is a photosensitizer that produces singlet oxygen. As used herein, "photosensitizer" refers to a light-adsorbing molecule that when activated by light converts molecular oxygen into singlet oxygen. Photosensitizers may be attached directly or indirectly, via covalent or non-covalent linkages, to the binding agent of a first binding reagent. Guidance for constructiing of such compositions, particularly for antibodies as binding agents, available in the literature, e.g. in the fields of photodynamic therapy, immunodiagnostics, and the like. The following are exemplary references: Ullman, et al, Proc. Natl. Acad. Sci. USA 91, 5426-5430 (1994); Strong et al, Ann. New York Acad. Sci., 745: 297-320 (1994); Yarnush et al, Crit. Rev. Therapeutic Drug Carrier Syst., 10: 197-252 (1993); Pease et al, U.S. Pat. No. 5,709,994; Ullman et al, U.S. Pat. No. 5,340,716; Ullman et al, U.S. Pat. No. 6,251,581; McCapra, U.S. Pat. No. 5,516,636; and the like.

Likewise, there is guidance in the literature regarding the properties and selection of photosensitizers suitable for use in the present invention. The following are exemplary references: Wasserman and R. W. Murray. Singlet Oxygen. (Academic Press, New York, 1979); Baumstark, Singlet Oxygen, Vol. 2 (CRC Press Inc., Boca Raton, Fla. 1983); and Turro, Modem Molecular Photochemistry (University Science Books, 1991).

The photosensitizers are sensitizers for generation of singlet oxygen by excitation with light. The photosensitizers include dyes and aromatic compounds, and are usually compounds comprised of covalently bonded atoms, usually with multiple conjugated double or triple bonds. The compounds typically absorb light in the wavelength range of about 200 to about 1,100 nm, usually, about 300 to about 1,000 nm, preferably, about 450 to about 950 nm, with an extinction coefficient at its absorbance maximum greater than about 500 $M^{-1}$ $cm^{-1}$, preferably, about 5,000 $M^{-1}$ $cm^{-1}$, more preferably, about 50,000 $M^{-1}$ $cm^{-1}$, at the excitation wavelength. The lifetime of an excited state produced following absorption of light in the absence of oxygen will usually be at least about 100 nanoseconds, preferably, at least about 1 millisecond. In general, the lifetime must be sufficiently long to permit cleavage of a linkage in a reagent in accordance with the present invention. Such a reagent is normally present at concentrations as discussed below. The photosensitizer excited state usually has a different spin quantum number (S) than its ground state and is usually a triplet (S=1) when the ground state, as is usually the case, is a singlet (S=0). Preferably, the photosensitizer has a high intersystem crossing yield. That is, photoexcitation of a photosensitizer usually produces a triplet state with an efficiency of at least about 10%, desirably at least about 40%, preferably greater than about 80%.

Photosensitizers chosen are relatively photostable and, preferably, do not react efficiently with singlet oxygen. Several structural features are present in most useful photosensitizers. Most photosensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3-6 of the periodic table, especially iodine or bromine, or they may have extended aromatic structures.

A large variety of light sources are available to photoactivate photosensitizers to generate singlet oxygen. Both polychromatic and monchromatic sources may be used as long as the source is sufficiently intense to produce enough singlet oxygen in a practical time duration. The length of the irradiation is dependent on the nature of the photosensitizer, the nature of the cleavable linkage, the power of the source of irradiation, and its distance from the sample, and so forth. In general, the period for irradiation may be less than about a microsecond to as long as about 10 minutes, usually in the range of about one millisecond to about 60 seconds. The intensity and length of irradiation should be sufficient to excite at least about 0.1% of the photosensitizer molecules, usually at least about 30% of the photosensitizer molecules and preferably, substantially all of the photosensitizer molecules. Exemplary light sources include, by way of illustration and not limitation, lasers such as, e.g., helium-neon lasers, argon lasers, YAG lasers, He/Cd lasers, and ruby lasers; photodiodes; mercury, sodium and xenon vapor lamps; incandescent lamps such as, e.g., tungsten and tungsten/halogen; flashlamps; and the like.

Examples of photosensitizers that may be utilized in the present invention are those that have the above properties and are enumerated in the following references: Turro, Modern Molecular Photochemistry (cited above); Singh and Ullman, U.S. Pat. No. 5,536,834; Li et al, U.S. Pat. No. 5,763,602; Ullman, et al., Proc. Natl. Acad. Sci. USA 91, 5426-5430 (1994); Strong et al, Ann. New York Acad. Sci., 745: 297-320 (1994); Martin et al, Methods Enzymol., 186: 635-645 (1990);Yarmush et al, Crit. Rev. Therapeutic Drug Carrier Syst., 10: 197-252 (1993); Pease et al, U.S. Pat. No. 5,709,994; Ullman et al, U.S. Pat. No. 5,340,716; Ullman et al, U.S. Pat. No. 6,251,581; McCapra, U.S. Pat. No. 5,516, 636; Wohrle, Chimia, 45: 307-310 (1991); Thetford, European patent publ. 0484027; Sessler et al, SPIE, 1426: 318-329 (1991); Madison et al, Brain Research, 522: 90-98 (1990); Polo et al, Inorganica Chimica Acta, 192: 1-3 (1992); Demas et al, J. Macromol. Sci., A25: 1189-1214 (1988); and the like. Exemplary photosensitizers are listed in Table 1b.

TABLE 1b

Exemplary Photosensitizers

| | |
|---|---|
| Hypocrellin A | Tetraphenylporphyrin |
| Hypocrellin B | Halogenated derivatives of |

TABLE 1b-continued

Exemplary Photosensitizers

| | |
|---|---|
| | rhodamine dyes |
| Hypericin | metallo-Porphyrins |
| Halogenated derivatives of fluorescein dyes | Phthalocyanines |
| Rose bengal | Naphthalocyanines |
| Merocyanine 540 | Texaphyrin-type macrocycles |
| Methylene blue | Hematophorphyrin |
| 9-Thioxanthone | 9,10-Dibromoanthracene |
| Chlorophylls | Benzophenone |
| Phenaleone | Chlorin e6 |
| Protoporphyrin | Perylene |
| Benzoporphryin A monacid | Benzoporphryin B monacid |

In certain embodiments the photosensitizer moiety comprises a support, as discussed above with respect to the cleavage-inducing moiety. The photosensitizer may be associated with the support by being covalently or non-covalently attached to the surface of the support or incorporated into the body of the support as discussed above. In general, the photosensitizer is associated with the support in an amount necessary to achieve the necessary amount of singlet oxygen. Generally, the amount of photosensitizer is determined empirically. Photosensitizers used as the photosensitizer are preferably relatively non-polar to assure dissolution into a lipophilic member when the photosensitizer is incorporated in, for example, a latex particle to form photosensitizer beads, e.g. as disclosed by Pease et al, U.S. Pat. No. 5,709,994. For example, the photosensitizer rose bengal is covalently attached to 0.5 micron latex beads by means of chloromethyl groups on the latex to provide an ester linking group, as described in J. Amer. Chem. Soc., 97: 3741 (1975).

In one aspect of the invention, a first binding reagent comprises a first binding agent that is an antibody and a cleavage-inducing moiety that is a photosensitizer, such that the photosensitizer is covalently linked to the antibody, e.g. using well know techniques as disclosed in Strong et al (cited above); Yarmush et al (cited above); or the like. Alternatively, a first binding reagent comprises a solid phase support, e.g. a bead, to which a photosensitizer is covalently or non-covalently attached and an antibody is attached, preferably convalently, either directly or by way of a functionalized polymer, such as amino-dextran, or the like.

Electrophoretic Probe Compositions

According to an important feature of the invention, there is provided a set of electrophoretic probes, each of which has a unique polypeptide-second binding agent and an associated "e-tag moiety" that imparts to the associated e-tag reporter, a unique electrophoretic mobility by virtue of a unique charge to mass ratio and/or optical characteristic. For convenience, the unique charge to mass ratio of an e-tag moiety is due to the chemical structure of the mobility modifier, since the detection group and linking-group residue (if any) will be common to any set of electrophoretic probes. However, it is recognized that unique charge and/or mass contributions to the e-tag reporters can be made by the detection group as well. For example, a set of electrophoretic probes may be made up of a first subset having a group of mobility modifiers which impart unique electrophoretic mobilities to the subset in combination with a detection group having one defined charge and/or mass, and a second subset having the same group of mobility modifiers in combination with a second detection group with a different charge and/or mass, thus to impart electrophoretic mobilities which are unique among both subsets.

In one aspect, the invention includes compositions comprising pluralities of electrophoretic probes. An electrophoretic probe comprises a second binding agent specific for a target polypeptide and one or more electrophoretic tags. The electrophoretic tags may be attached to the second binding agent directly or indirectly by a secondary binding molecule that binds specifically to the second binding agent, such as a secondary antibody specific for the constant region of a primary antibody. Preferably, the second binding agent of an electrophoretic probe is an antibody. Generally, an electrophoretic probe is defined by the following formula:

$$T\text{-}(L\text{-}E)_k$$

wherein T is the second binding agent, or more specifically, a polypeptide-second binding agent; L is a cleavable linkage; and E is an electrophoretic tag, or "e-tag." Preferably, cleavable linkage, L, is an oxidation-labile linkage, and more preferably, it is a linkage that may be cleaved by singlet oxygen. The moiety "–(L–E)$_k$" indicates that a single second binding agent may have one or more electrophoretic tags attached via cleavable linkages. k is an integer greater than or equal to 1; and preferably, k is an integer in the range of from 1 to 500; and more preferably, k is an integer in the range of from 1 to 100 or from 1 to 50; and still more preferably, k is an integer in the range of from 1 to 10. Preferably, the plurality of electrophoretic probes is at least 5, and more preferably, at least 10. Still more preferably, the plurality is in the range of from 5 to 200, and more preferably, from 5 to 100, or from 5 to 50, or from 10 to 30. Preferably, within a plurality, each different second binding agent, T, has a different electrophoretic tag, E. Oxidation-labile linkages and tags, E, are attached to T by way of conventional linking chemistries. Preferably, whenever T is a polypeptide attachment may be through the common reactive functionalities, such as amino, sulfide, carboxyl, and the like.

Preferably, second binding agent, T, is an antibody, or comprises an antibody, specific for a target protein, or polypeptide. In the latter case, T may comprise a plurality of binding components that operate together to hold an electrophoretic tag in the proximity of a target protein. For example, T may be an antibody together with a secondary antibody having e-tags attached, a haptenized antibody together with a secondary anti-hapten antibody having e-tags attached, a biotinylated antibody together with streptavidin having e-tags attached, an antibody derivatized with a functionalized polymer that, in turn, has e-tags attached, or the like. A plurality of electrophoretic probes are preferably used in the method of the invention, wherein each probe has a different second binding agent, T.

Preferably, L is a thioether or its selenium analog; or an olefin, which contains carbon-carbon double bonds, wherein cleavage of a double bond to an oxo group, releases the e-tag, E. Illustrative olefins include vinyl sulfides, vinyl ethers, enamines, imines substituted at the carbon atoms with an α-methine (CH, a carbon atom having at least one hydrogen atom), where the vinyl group may be in a ring, the heteroatom may be in a ring, or substituted on the cyclic olefinic carbon atom, and there will be at least one and up to four heteroatoms bonded to the olefinic carbon atoms. The resulting dioxetane may decompose spontaneously, by heating above ambient temperature, usually below about 75° C., by reaction with acid or base, or by photo-activation in the absence or presence of a photosensitizer. Such reactions are described in the following exemplary references: Adam and Liu, J. Amer. Chem. Soc. 94, 1206-1209, 1972, Ando, et al., J.C.S. Chem. Comm. 1972, 477-8, Ando, et al., Tetrahedron 29, 1507-13, 1973, Ando, et al., J. Amer. Chem. Soc. 96, 6766-8, 1974, Ando and Migita, ibid. 97, 5028-9, 1975, Wasserman and Terao, Tetra. Lett. 21, 1735-38, 1975, Ando and Watanabe, ibid. 47, 4127-30, 1975, Zaklika, et al., Photochemistry and Photobiology 30, 35-44, 1979, and Adam, et al., Tetra. Lett. 36, 78534, 1995. See also, U.S. Pat. No. 5,756,726.

The formation of dioxetanes is obtained by the reaction of singlet oxygen with an activated olefin substituted with an e-tag moiety at one carbon atom and the second binding agent at the other carbon atom of the olefin. See, for example, U.S. Pat. No. 5,807,675. These cleavable linkages may be depicted by the following formula:

$$-W-(X)_n C_\alpha = C_\beta(Y)(Z)-$$

wherein:

W may be a bond, a heteroatom, e.g., O, S, N, P, M (intending a metal that forms a stable covalent bond), or a functionality, such as carbonyl, imino, etc., and may be bonded to X or $C_\alpha$; at least one X will be aliphatic, aromatic, alicyclic or heterocyclic and bonded to $C_\alpha$ through a hetero atom, e.g., N, O, or S and the other X may be the same or different and may in addition be hydrogen, aliphatic, aromatic, alicyclic or heterocyclic, usually being aromatic or aromatic heterocyclic wherein one X may be taken together with Y to form a ring, usually a heterocyclic ring, with the carbon atoms to which they are attached, generally when other than hydrogen being from about 1 to 20, usually 1 to 12, more usually 1 to 8 carbon atoms and one X will have 0 to 6, usually 0 to 4 heteroatoms, while the other X will have at least one heteroatom and up to 6 heteroatoms, usually 1 to 4 heteroatoms;

Y will come within the definition of X, usually being bonded to $C_\beta$ through a heteroatom and as indicated may be taken together with X to form a heterocyclic ring;

Z will usually be aromatic, including heterocyclic aromatic, of from about 4 to 12, usually 4 to 10 carbon atoms and 0 to 4 heteroatoms, as described above, being bonded directly to $C_\beta$ or through a heteroatom, as described above;

n is 1 or 2, depending upon whether the e-tag moiety is bonded to $C_\alpha$ or X;

wherein one of Y and Z will have a functionality for binding to the second binding agent, or be bound to the second binding agent, e.g. by serving as, or including a linkage group, to a second binding agent, T.

Preferably, W, X, Y, and Z are selected so that upon cleavage electrophoretic tag, E, is within the size limits described below.

While not depicted in the formula, one may have a plurality of e-tag moieties in a single molecule, by having one or more e-tag moieties joined to one or both Xs.

Illustrative cleavable linkages include S-3-thiolacrylic acid, -N,N-methyl 4-amino-4-butenoic acid, —O, 3-hydroxyacrolein, N—(4-carboxyphenyl) 2-imidazole, oxazole, and thiazole.

Also of interest are N-alkyl acridinyl derivatives, substituted at the 9 position with a divalent group of the formula:

$$-(CO)X^1(A)-$$

wherein:

$X^1$ is a heteroatom selected from the group consisting of O, S, N, and Se, usually one of the first three; and A is a chain of at least 2 carbon atoms and usually not more than 6 carbon atoms substituted with an e-tag reporter, where preferably the other valences of A are satisfied by hydrogen, although the chain may be substituted with other groups, such as alkyl, aryl, heterocyclic groups, etc., A generally being not more than 10 carbon atoms.

Also of interest are heterocyclic compounds, such as diheterocyclopentadienes, as exemplified by substituted imidazoles, thiazoles, oxazoles, etc., where the rings will usually be substituted with at least one aromatic group and in some instances hydrolysis will be necessary to release the e-tag reporter.

Also of interest are tellurium (Te) derivatives, where the Te is bonded to an ethylene group having a hydrogen atom β to the Te atom, wherein the ethylene group is part of an alicyclic or heterocyclic ring, that may have an oxo group, preferably fused to an aromatic ring and the other valence of the Te is bonded to the e-tag reporter. The rings may be coumarin, benzoxazine, tetralin, etc.

Figure 3A:
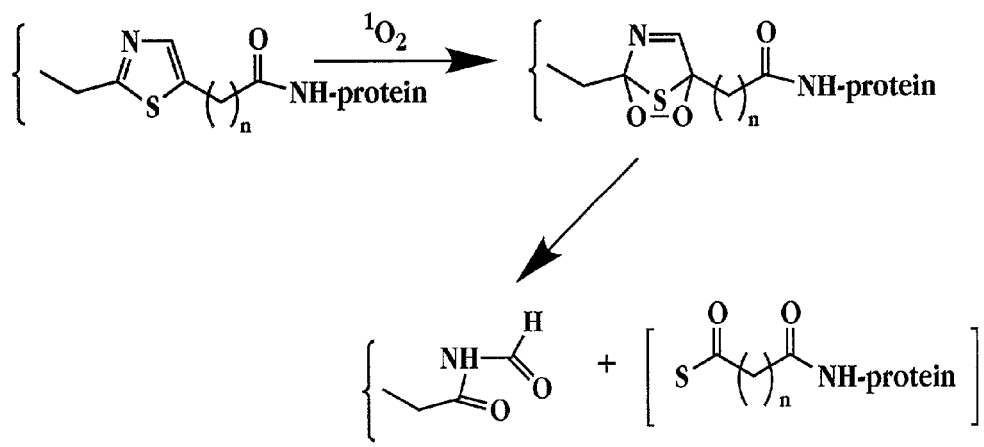
FIGS. 3A-F illustrate oxidation-labile linkages and their respective cleavage reactions mediated by singlet oxygen.
Figure 3B:
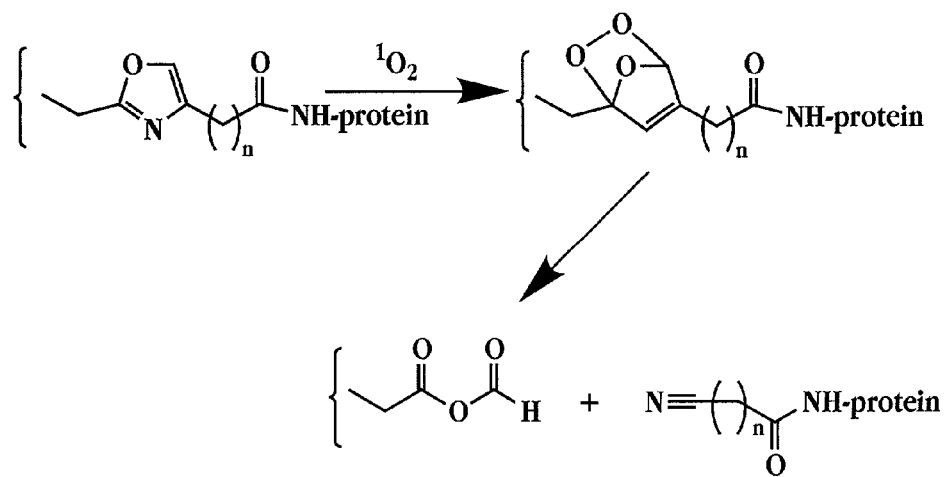
Figure 3C:
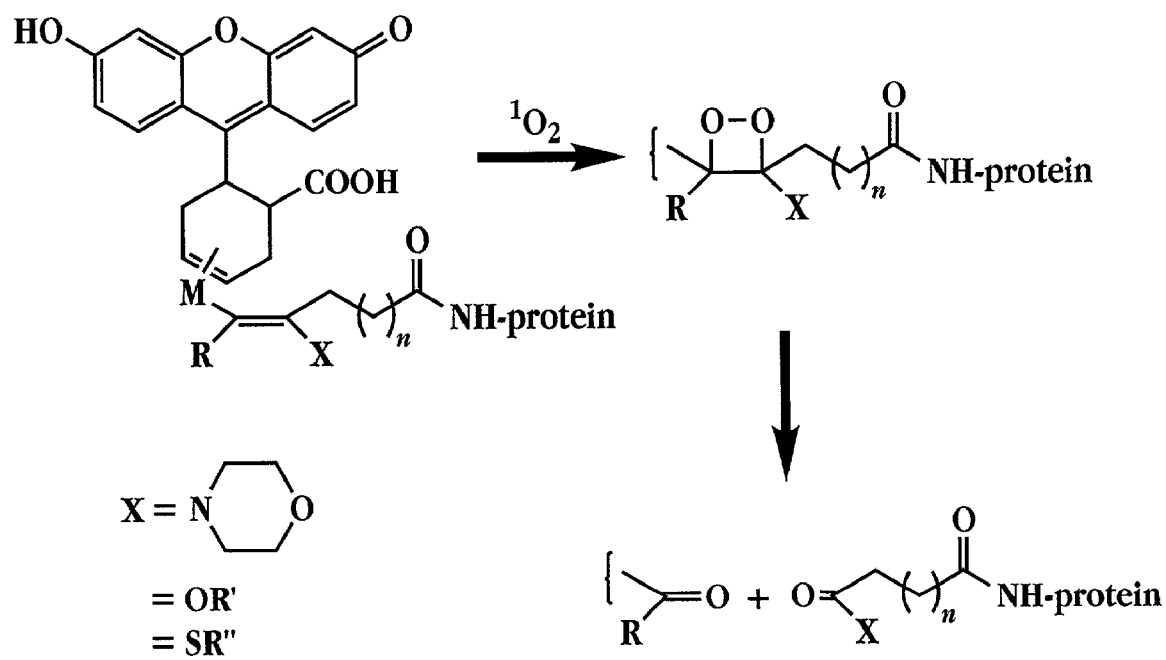
Figure 3D:
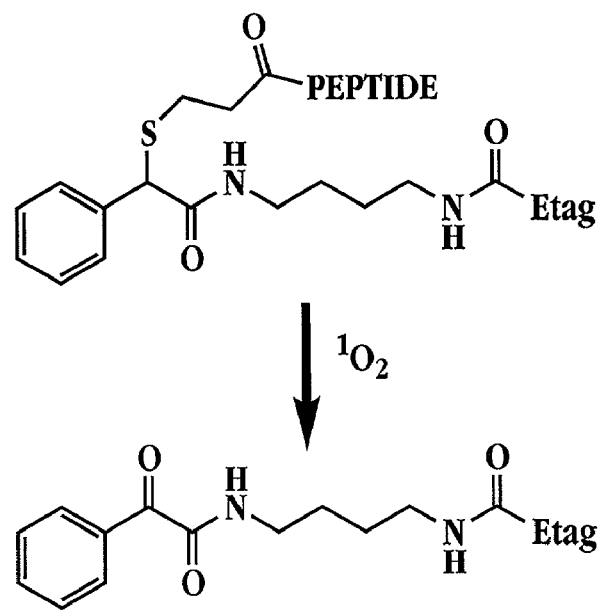
Figure 3E:
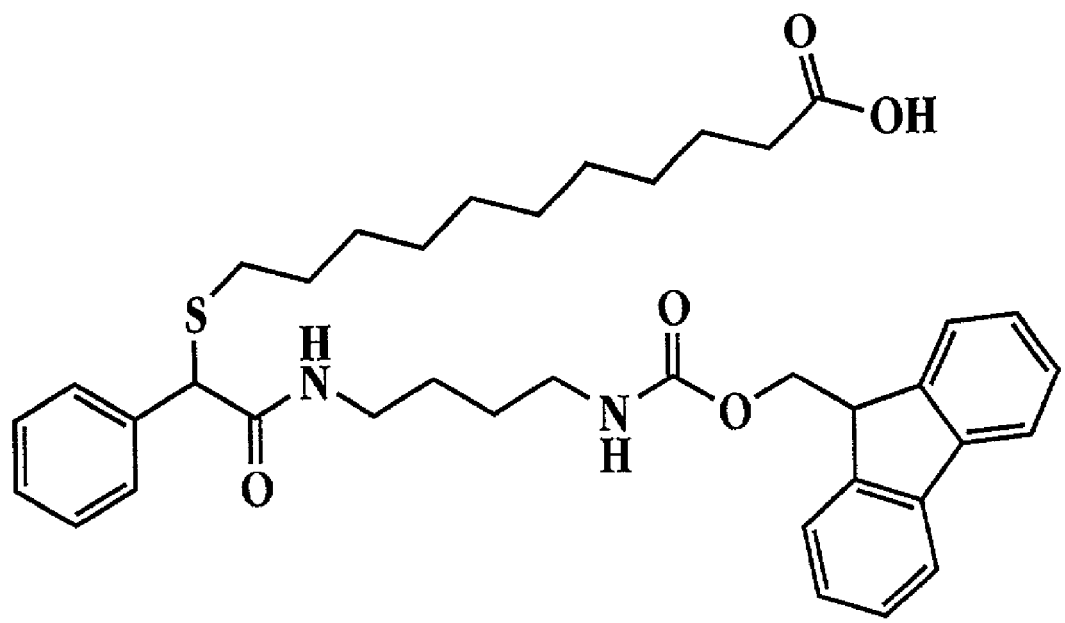
Figure 3F:
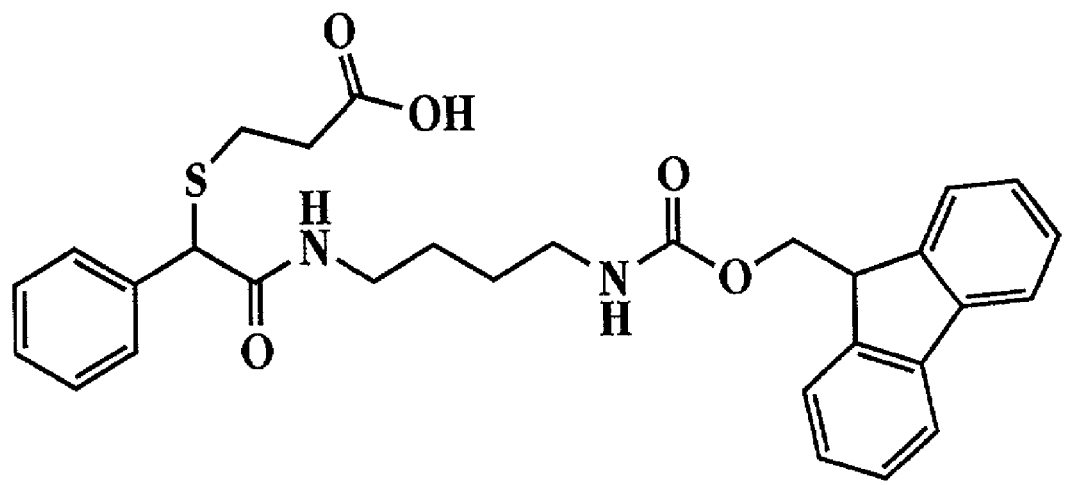

Several preferred cleavable linkages and their cleavage products are illustrated in FIGS. 3A-F. The thiazole cleavable linkage, "—CH2-thiazole-$(CH_2)_n$—C(=O)—NH-protein," shown in FIG. 3A, results in an electrophoretic tag with the moiety "—$CH_2$—C(=O)—NH—CHO." Preferably, n is in the range of from 1 to 12, and more preferably, from 1 to 6. The oxazole cleavable linkage, "—$CH_2$-oxazole-$(CH2)_n$—C(=O)—NH-protein," shown in FIG. 3B, results in an electrophoretic tag with the moiety "—$CH_2$—C(=O)O—CHO." An olefin cleavable linkage (FIG. 3C) is shown in connection with the electrophoretic probe embodiment "T-L-M-D," described above and with D being a fluorescein dye. The olefin cleavable linkage may be employed in other embodiments also. Cleavage of the illustrated olefin linkage results in an electrophoretic tag of the form: "R—(C=O)-M-D," where "R" may be any substituent within the general description of the electrophoretic tags, E, provided above. Preferably, R is an electron-donating group, e.g. Ullman et al, U.S. Pat. No. 6,251,581; Smith and March, March's Advanced Organic Chemistry: Reactions, Mechanisms, and Structure, $5^{th}$ Edition (Wiley-Interscience, New York, 2001); and the like. More preferably, R is an electron-donating group having from 1-8 carbon atoms and from 0 to 4 heteroatoms selected from the group consisting of O, S, and N. In further preference, R is —$N(Q)_2$, —OQ, p-$[C_6H_4N(Q)_2]$, furanyl, n-alkylpyrrolyl, 2-indolyl, or the like, where D is alkyl or aryl. In further reference to the olefin cleavable linkage of FIG. 3C, substituents "X" and "R" are equivalent to substituents "X" and "Y" of the above formula describing cleavable linkage, L. In particular, X in FIG. 3C is preferably morpholino, —OR', or —SR", where R' and R" are aliphatic, aromatic, alicyclic or heterocyclic having from 1 to 8 carbon atoms and 0 to 4 heteroatoms selected from the group consisting of O, S. and N. A preferred thioether cleavable linkage is illustrated in FIG. 3D having the form "—$(CH_2)_2$—S—$CH(C_6H_5)C$(=O)NH—$(CH_2)_n$—NH—," wherein n is in the range of from 2 to 12, and more preferably, in the range of from 2 to 6. Thioether cleavable linkages of the type shown in FIG. 3D may be attache to binding moieties, T, and electrophoretic tags, E, by way of precursor compounds shown in FIGS. 3E and 3F. To attach to an amino group of a second binding agent, T, the terminal hydroxyl is converted to an NHS ester by conventional chemistry. After reaction with the amino group and attachment, the Fmoc protection group is removed to produce a free amine which is then reacted with an NHS ester of the e-tag, such as compounds produced by the schemes of FIGS. 1, 2, and 4, with the exception that thelast reaction step is the addition of an NHS ester, instead of a phosphoramidite group.

Electrophoretic tag, E, is a water soluble organic compound that is stable with respect to the active species, especially singlet oxygen, and that includes a signal amplification moiety, or catalytic group. Otherwise, E may vary widely in size and structure. Preferably, E carries a charge at neutral pH and has a molecular weight in the range of from about 150 to about 10,000 daltons, more preferably, from about 150 to about 5000 daltons, and most preferably, from about 150 to 2500 daltons. Preferred structures of E are described more fully below. Preferably, the signal amplification moiety is an inactivated photosensitizer. Compositions of the invention include pluralities of electrophoretic tags that may be used together to carry out the multiplexed assays of the invention. Preferably, the plurality of electrophoretic tags in a composition is at least 5, and more preferably, at least 10. Still more preferably, the plurality is in the range of from 5 to 200, and more preferably, from 5 to 100, or 5 to 75, or from 5 to 50, or from 10 to 30. Preferably, electrophoretic tags within a plurality of a composition each have either a unique charge-to-mass ratio and/or a unique optical property with respect to the other members of the same plurality.

Preferably, electrophoretic tags in a plurality are detected by detectable products generated by the tags' signal amplification moiety after electrophoretic separation. Preferably, electrophoretic tags have different electrophoretic mobilities so that distinct peaks in an electropherogram are formed under separation conditions. A measure of the distinctness, or lack of overlap, of adjacent peaks is electrophoretic resolution, which is the distance between adjacent peak maximums divided by four times the larger of the two standard deviations of the peaks. Preferably, adjacent peaks have a resolution of at least 1.0, and more preferably, at least 1.5, and most preferably, at least 2.0. In a given separation and detection system, the desired resolution may be obtained by selecting a plurality of electrophoretic tags whose members have electrophoretic mobilities that differ by at least a peak-resolving amount, such quantity depending on several factors well known to those of ordinary skill, including signal detection system, the diffusion coefficients of the tags, the presence or absence of sieving matrices, nature of the electrophoretic apparatus, e.g. presence or absence of channels, length of separation channels, and the like. Preferably, pluralities of electrophoretic tags of the invention are separated by conventional capillary electrophoresis apparatus, either in the presence or absence of a conventional sieving matix. Exemplary capillary electroresis apparatus include Applied Biosystems (Foster City, Calif.) models 310, 3100 and 3700; Beckman (Fullerton, Calif.) model P/ACE MDQ; Amersham Biosciences (Sunnyvale, Calif.) MegaBACE 1000 or 4000; SpectruMedix genetic analysis system; and the like. Preferably, in such conventional apparatus, the electrophoretic mobilities of electrophoretic tags of a plurality differ by at least one percent, and more preferably, by at least a percentage in the range of from 1 to 10 percent.

Electrophoretic mobility is proportional to $q/M^{2/3}$, where q is the charge on the molecule and M is the mass of the molecule. Desirably, the difference in mobility under the conditions of the determination between the closest electrophoretic labels will be at least about 0.001, usually 0.002, more usually at least about 0.01, and may be 0.02 or more.

A preferred structure of electrophoretic tag, E, is (M, I), where M is a mobility-modifying moiety and I is a signal amplification moiety. The notation "(M, I)" is used to indicate that the ordering of the M and I moieties may be such that either moiety can be adjacent to the cleavable linkage, L. That is, "T-L-(M, I)" designates electrophoretic probe of either of two forms: "T-L-M-I" or "T-L-I-M."

M is generally a chemical group or moiety that has or is designed to have a particular charge-to-mass ratio, and thus a particular electrophoretic mobility in a defined electrophoretic system. Exemplary types of mobility-modifying moieties are discussed below. In a set of n electrophoretic probes, each unique mobility modifier is designated $M_j$, where j=1 to n, and n has a value as described above. The mobility-modifying moiety may be considered to include a mass-modifying region and/or a charge-modifying region or a single region that acts as both a mass- and charge-modifying region. In the probe sets utilized in the invention, the mobility-modifying moiety may have one or more of the following characteristics: (i) a unique charge-to-mass ratio due to variations in mass, but not charge; (ii) a unique charge-to-mass ratio due to changes in both mass and charge; and (iii) a unique charge-to-mass ratios of between about −0.0001 and about 0.5, usually, about −0.001 and about 0.1. As noted above, I is typically common among a set or plurality of different electrophoretic probes, but may also differ among probe sets, contributing to the unique electrophoretic mobilities of the released e-tag.

In a preferred embodiment, I is selected from the group consisting of thiazine dyes. Preferably, such thiazine dyes include methylene blue, azure A, azure C, toluidine blue O, and thionine. Most preferably, I is methylene blue. These dyes may be attached to mobility modifying moieties and/or second binding agents using known chemistry. For example, the following references teach the attachment of such dye by way of NHS-ester derivatives: Masuya et al, European patent publication 0510668; Motsenbocker, U.S. Pat. No. 5,532,171; Motsenbocker et al, Photochem. and Photobiol., 58: 648-652 (1993); and the like. Further properties of these dyes are disclosed in Floyd et al, U.S. Pat. No. 6,346,529.

The size and composition of mobility-modifying moiety, M, can vary from a bond to about 100 atoms in a chain, usually not more than about 60 atoms, more usually not more than about 30 atoms, where the atoms are carbon, oxygen, nitrogen, phosphorous, boron and sulfur. Generally, when other than a bond, the mobility-modifying moiety has from about 0 to about 40, more usually from about 0 to about 30 heteroatoms, which in addition to the heteroatoms indicated above may include halogen or other heteroatom. The total number of atoms other than hydrogen is generally fewer than about 200 atoms, usually fewer than about 100 atoms. Where acid groups are present, depending upon the pH of the medium in which the mobility-modifying moiety is present, various cations may be associated with the acid group. The acids may be organic or inorganic, including carboxyl, thionocarboxyl, thiocarboxyl, hydroxamic, phosphate, phosphite, phosphonate, phosphinate, sulfonate, sulfinate, boronic, nitric, nitrous, etc. For positive charges, substituents include amino (includes ammonium), phosphonium, sulfonium, oxonium, etc., where substituents are generally aliphatic of from about 1-6 carbon atoms, the total number of carbon atoms per heteroatom, usually be less than about 12, usually less than about 9. The side chains include amines, ammonium salts, hydroxyl groups, including phenolic groups, carboxyl groups, esters, amides, phosphates, heterocycles. M may be a homo-oligomer or a hetero-oligomer, having different monomers of the same or different chemical characteristics, e.g., nucleotides and amino acids.

The charged mobility-modifying moieties generally have only negative or positive charges, although one may have a combination of charges, particularly where a region to which the mobility-modifying moiety is attached is charged and the mobility-modifying moiety has the opposite charge. The mobility-modifying moieties may have a single monomer that provides the different functionalities for oligomerization and carry a charge or two monomers may be employed, generally two monomers. One may use substituted diols, where the substituents are charged and dibasic acids. Illustrative of such oligomers is the combination of diols or diamino, such as 2,3-dihydroxypropionic acid, 2,3-dihydroxysuccinic acid, 2,3-diaminosuccinic acid, 2,4-dihydroxyglutaric acid, etc. The diols or diamino compounds can be linked by dibasic acids, which dibasic acids include the inorganic dibasic acids indicated above, as well as dibasic acids, such as oxalic acid, malonic acid, succinic acid, maleic acid, fumaric acid, carbonic acid, etc. Instead of using esters, one may use amides, where amino acids or diamines and diacids may be employed. Alternatively, one may link the hydroxyls or amines with alkylene or arylene groups.

By employing monomers that have substituents that provide for charges, or which may be modified to provide charges, one can provide for mobility-modifying moieties having the desired charge-to-mass ratio. For example, by using serine or threonine, one may modify the hydroxyl groups with phosphate to provide negatively charged mobility-modifying moieties. With arginine, lysine and histidine, one provides for positively charged mobility-modifying moieties. Oligomerization may be performed in conventional ways to provide the appropriately sized mobility-modifying moiety. The different mobility-modifying moieties having different orders of oligomers, generally having from 1 to 20 monomeric units, more usually about 1 to 12, where a unit intends a repetitive unit that may have from 1 to 2 different monomers. For the most part, oligomers may be used with other than nucleic acid target-binding regions. The polyfunctionality of the monomeric units provides for functionalities at the termini that may be used for conjugation to other moieties, so that one may use the available functionality for reaction to provide a different functionality. For example, one may react a carboxyl group with an aminoethylthiol, to replace the carboxyl group with a thiol functionality for reaction with an activated olefin.

By using monomers that have about 1 to about 3 charges, one may employ a low number of monomers and provide for mobility variation with changes in molecular weight. Of particular interest are polyolpolycarboxylic acids having from about two to four of each functionality, such as tartaric acid, 2,3-dihydroxyterephthalic acid, 3,4-dihydroxyphthalic acid, $\Delta^5$-tetrahydro-3,4-dihydroxyphthalic acid, etc. To provide for an additional negative charge, these monomers may be oligomerized with a dibasic acid, such as a phosphoric acid derivative to form the phosphate diester. Alternatively, the carboxylic acids could be used with a diamine to form a polyamide, while the hydroxyl groups could be used to form esters, such as phosphate esters, or ethers such as the ether of glycolic acid, etc. To vary the mobility, various aliphatic groups of differing molecular weight may be employed, such as polymethylenes, polyoxyalkylenes, polyhaloaliphatic or aromatic groups, polyols, e.g., sugars, where the mobility will differ by at least about 0.01, more usually at least about 0.02 and more usually at least about 0.5.

In another aspect, (M,I) moieties are constructed from chemical scaffolds used in the generation of combinatorial libraries. For example, the following references describe scaffold compound useful in generating diverse mobility modifying moieties: peptoids (PCT Publication No WO 91/19735, Dec. 26, 1991), encoded peptides (PCT Publication WO 93/20242, Oct. 14 1993), random bio-oligomers (PCT Publication WO 92/00091, Jan. 9, 1992), benzodiazepines (U.S. Pat. No. 5,288,514), diversomeres such as hydantoins, benzodiazepines and dipeptides (Hobbs DeWitt, S. et al., Proc. Nat. Acad. Sci. U.S.A. 90: 6909-6913 (1993), vinylogous polypeptides (Hagihara et al. J.Amer. Chem. Soc. 114: 6568 (1992)), nonpeptidal peptidomimetics with a Beta-D-Glucose scaffolding (Hirschmann, R. et al., J.Amer. Chem. Soc. 114: 9217-9218 (1992)), analogous organic syntheses of small compound libraries (Chen, C. et al. J.Amer. Chem. Soc. 116: 2661(1994)), oligocarbamates (Cho, C. Y. et al. Science 261: 1303(1993)), peptidyl phosphonates (Campbell, D. A. et al, J. Org. Chem. 59:658 (1994)); Cheng et al, U.S. Pat. No. 6,245,937; Heizmann et al, "Xanthines as a scaffold for molecular diversity," Mol. Divers. 2: 171-174 (1997); Pavia et al, Bioorg. Med. Chem., 4: 659-666 (1996); Ostresh et al, U.S. Pat. No. 5,856,107; Gordon, E. M. et al., J. Med. Chem. 37: 1385 (1994); and the like. Preferably, in this aspect, I is a substituent on a scaffold and M is the rest of the scaffold.

In yet another aspect, (M, I) moieties are constructed from common or commercially available linking, cross-linking, and labeling reagents that permit facile assembly, especially using a commercial DNA or peptide synthesizer for all or part of the synthesis. In this aspect, (M, I) moieties are made up of subunits usually connected by phosphodiester and amide bonds. Exemplary, precusors include, but are not limited to, dimethoxytrityl (DMT)-protected hexaethylene glycol phosphoramidite, 6-(4-Monomethoxytritylamino) hexyl-(2-cyanoethyl)-(N,N-diisopropyl)-phosphoramidite, 12-(4-Monomethoxytritylamino)dodecyl-(2-cyanoethyl)-(N,N-diisopropyl)-phosphoramidite, 2-[2-(4-Monomethoxytrityl)aminoethoxy]ethyl-(2-cyanoethyl), N,N-diisopropyl)-phosphoramidite, (S-Trityl-6-mercaptohexyl)-(2-cyanoethyl)-(N,N-diisopropyl)-phosphoramidite, 5'-Fluorescein phosphoramidite, 5'-Hexachloro-Fluorescein Phosphoramidite, 5'-Tetrachloro-Fluorescein Phosphoramidite, 9-O-Dimethoxytrityl-triethylene glycol,1-[(2-cyanoethyl)-(N,N-diisopropyl)]-phosphoramidite, 3(4,4'Dimethoxytrityloxy)propyl-1-[(2-cyanoethyl)-(N,N-diisopropyl)]-phosphoramidite, 5'-O-Dimethoxytrityl-1',2'-Dideoxyribose-3'-[(2-cyanoethyl)-(N,N-diisopropyl)]-phosphoramidite, 18-0 Dimethoxytritylhexaethyleneglycol, 1-[(2-cyanoethyl)-(N,N-diisopropyl)]-phosphoramidite, 12-(4,4'-Dimethoxytrityloxy)dodecyl-1-[(2-cyanoethyl)-(N,N-diisopropyl)]-phosphoramidite, 1,3-bis-[5-(4,4'-dimethoxytrityloxy)pentylamido]propyl-2-[(2-cyanoethyl)-(N,N-diisopropyl)]-phosphoramidite, 1-[5-(4,4'-dimethoxytrityloxy)pentylamido]-3-[5-fluorenomethoxycarbonyloxy pentylamido]-propyl-2-[(2-cyanoethyl)-(N,N-diisopropyl)]-phosphoramidite, Tris-2,2, 2-[3-(4,4'-dimethoxytrityloxy)propyloxymethyl]ethyl-[(2-cyanoethyl)-(N,N-diisopropyl)]-phosphoramidite, succinimidyl trans-4-(maleimidylmethyl) cyclohexane-1-carboxylate (SMCC), succinimidyl 3-(2-pyridyldithio)propionate (SPDP), succinimidyl acetylthioacetate, Texas Red-X-succinimidyl ester, 5- and 6-carboxytetramethylrhodamine succinimidyl ester, bis-(4-carboxypiperidinyl)sulfonerhodamine di(succinimidyl ester), 5- and 6-((N-(5-aminopentyl)aminocarbonyl)tetramethylrhodamine, succinimidyl 4-(p-maleimidophenyl)butyrate (SMPB); N-γ-maleimidobutyryl-oxysuccinimide ester (GMBS); p-nitrophenyl iodoacetate (NPIA); 4-(4-N-maleimidophenyl)butyric acid hydrazide (MPBH); and like reagents. The above reagents are commercially available, e.g. from Glen Research (Sterling, Va.), Molecular Probes (Eugene, Oreg.), Pierce Chemical, and like reagent providers. Use of the above reagents in conventional synthetic schemes is well known in the art, e.g. Hermanson, Bioconjugate Techniques (Academic Press, New York, 1996). In particular, M may be constructed from the following reagents: dimethoxytrityl (DMT)-protected hexaethylene glycol phosphoramidite, 6-(4-Monomethoxytritylamino) hexyl-(2-cyanoethyl)-(N,N-diisopropyl)-phosphoramidite, 12-(4-Monomethoxytritylamino)dodecyl-(2-cyanoethyl)-(N,N-diisopropyl)-phosphoramidite, 2-[2-(4-Monomethoxytrityl)aminoethoxy]ethyl-(2-cyanoethyl), N,N-diisopropyl)-phosphoramidite, (S-Trityl-6-mercaptohexyl)-(2-cyanoethyl)-(N,N-diisopropyl)-phosphoramidite, 9-O-Dimethoxytrityl-triethylene glycol, 1-[(2-cyanoethyl)-(N,N-diisopropyl)]-phosphoramidite, 3(4,4'Dimethoxytrityloxy)propyl-1-[(2-cyanoethyl)-(N,N-diisopropyl)]-phosphoramidite, 5'-O-Dimethoxytrityl-1',2'-Dideoxyribose-3'-[(2-cyanoethyl)-(N,N-diisopropyl)]-phosphoramidite, 18-0 Dimethoxytritylhexaethyleneglycol, 1-[(2-cyanoethyl)-(N,N-diisopropyl)]-phosphoramidite, 12-(4,4'-Dimethoxytrityloxy)dodecyl-1-[(2-cyanoethyl)-(N,N-diisopropyl)]-phosphoramidite, 1,3-bis-[5-(4,4'-dimethoxytrityloxy)pentylamido]propyl-2-[(2-cyanoethyl)-(N,N-diisopropyl)]-phosphoramidite, 1-[5-(4,4'-dimethoxytrityloxy)pentylamido]-3-[5-fluorenomethoxycarbonyloxy pentylamido]-propyl-2-[(2-cyanoethyl)-(N,N-diisopropyl)]-phosphoramidite, Tris-2,2, 2-[3-(4,4'-dimethoxytrityloxy)propyloxymethyl]ethyl-[(2-cyanoethyl)-(N,N-diisopropyl)]-phosphoramidite, succinimidyl trans-4-(maleimidylmethyl) cyclohexane-1-carboxylate (SMCC), succinimidyl 3-(2-pyridyldithio)propionate (SPDP), succinimidyl acetylthioacetate, succinimidyl 4-(p-maleimidophenyl)butyrate (SMPB); N-γ-maleimidobutyryl-oxysuccinimide ester (GMBS); p-nitrophenyl iodoacetate (NPIA); and 4-(4-N-maleimidophenyl)butyric acid hydrazide (MPBH).

M may also comprise polymer chains prepared by known polymer subunit synthesis methods. Methods of forming selected-length polyethylene oxide-containing chains are well known, e.g. Grossman et al, U.S. Pat. No. 5,777,096. It can be appreciated that these methods, which involve coupling of defined-size, multi-subunit polymer units to one another, directly or via linking groups, are applicable to a wide variety of polymers, such as polyethers (e.g., polyethylene oxide and polypropylene oxide), polyesters (e.g., polyglycolic acid, polylactic acid), polypeptides, oligosaccharides, polyurethanes, polyamides, polysulfonamides, polysulfoxides, polyphosphonates, and block copolymers thereof, including polymers composed of units of multiple subunits linked by charged or uncharged linking groups. In addition to homopolymers, the polymer chains used in accordance with the invention include selected-length copolymers, e.g., copolymers of polyethylene oxide units alternating with polypropylene units. As another example, polypeptides of selected lengths and amino acid composition (i.e., containing naturally occurring or man-made amino acid residues), as homopolymers or mixed polymers.

In a preferred aspect, after release, electrophoretic tag, E, is defined by the formula:

A-M-I wherein:

A is —C(=O)R, where R is aliphatic, aromatic, alicyclic or heterocyclic having from 1 to 8 carbon atoms and 0 to 4 heteroatoms selected from the group consisting of O, S. and N; —CH$_2$—C(=O)—NH—CHO; —SO$_2$H; —CH$_2$—C(=O)O—CHO; —C(=O)NH—(CH$_2$)$_n$—NH—C(=O)C(=O)—(C$_6$H$_5$), where n is in the range of from 2 to 12;

I is a signal amplification moiety as described above; and

M is as described above, with the proviso that the total molecular weight of A-M-I be within the range of from about 150 to about 5000 daltons, and more preferably, within the range of from about 150 to about 2500 daltons.

In some embodiments the e-tag moieties need not be charged but merely differ in mass. Thus, one could use the same or similar monomers, where the functionalities would be neutral or made neutral, such as esters and amides of carboxylic acids. Also, one may vary the e-tag moieties by isotopic substitution, such as $^2$H, $^{18}$O, $^{14}$C, etc.

Pluralities of electrophoretic tags may include oligopeptides for providing the charge, particularly oligopeptides of from 2-6, usually 2-4 monomers, either positive charges resulting from lysine, arginine and histidine or negative charges, resulting from aspartic and glutamic acid. Of course, one need not use naturally occurring amino acids, but unnatural or synthetic amino acids, such as taurine, phosphate substituted serine or threonine, S-α-succinylcysteine, co-oligomers of diamines and amino acids, etc.

In one embodiment of the present invention, the charge-imparting moiety is conveniently composed primarily of amino acids but also may include thioacids and other carboxylic acids having from one to five carbon atoms. The charge imparting moiety may have from about 1 to about 30, preferably about 1 to about 20, more preferably, about 1 to about 10 amino acids per moiety and may also comprise about 1 to about 3 thioacids or other carboxylic acids. However, when used with an uncharged sub-region, the charged sub-region will generally have from about 1 to about 4, frequently about 1 to about 3 amino acids. As mentioned above, any amino acid, both naturally occurring and synthetic, may be employed.

In a particular embodiment, T-L-M-I may be represented by the formula:

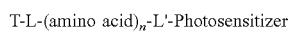

T-L-(amino acid)$_n$-L'-Photosensitizer wherein L' is a bond or a linking group of from 1 to 20 atoms other than hydrogen, n is 1 to 20, and L is a cleavable linkage to the polypeptide-second binding agent. In this embodiment T is linked to the terminal amino acid by a cleavable linkage. An example of this embodiment, by way of illustration and not limitation, is one in which the photosensitizer is methylene blue, L' is a linkage to the terminal amine group of lysine, and T is a polypeptide-second binding agent.

In another embodiment, mobility-modifying moiety, M, is dependent on using an alkylene or aralkylene (comprising a divalent aliphatic group having about 1 to about 2 aliphatic regions and about 1 to about 2 aromatic regions, generally benzene), where the groups may be substituted or unsubstituted, usually unsubstituted, of from about 2 to about 16, more usually about 2 to about 12, carbon atoms, where the mobility-modifying moiety may link the same or different fluorescers to a monomeric unit, e.g., a nucleotide. The mobility-modifying moiety may terminate in a carboxy, hydroxy or amino group, being present as an ester or amide. By varying the substituents on the fluorophore, one can vary the mass in units of at least about 5 or more, usually at least about 9, so as to be able to obtain satisfactory separation in capillary electrophoresis. To provide further variation, a thiosuccinimide group may be employed to join alkylene or aralkylene groups at the nitrogen and sulfur, so that the total number of carbon atoms may be in the range of about 2 to about 30, more usually about 2 to about 20. Instead of or in combination with the above groups and to add hydrophilicity, one may use alkyleneoxy groups.

Besides the nature of the mobility-modifying moiety, as already indicated, diversity can be achieved by the chemical and optical characteristics of the label, the use of energy transfer complexes, variation in the chemical nature of the mobility-modifying moiety, which affects mobility, such as folding, interaction with the solvent and ions in the solvent, and the like. In one embodiment of the invention, the mobility-modifying moiety may be an oligomer, where the mobility-modifying moiety may be synthesized on a support or produced by cloning or expression in an appropriate host. Conveniently, polypeptides can be produced where there is only one cysteine or serine/threonine/tyrosine, aspartic/glutamic acid, or lysine/arginine/histidine, other than an end group, so that there is a unique functionality, which may be differentially functionalized. By using protective groups, one can distinguish a side-chain functionality from a terminal amino acid functionality. Also, by appropriate design, one may provide for preferential reaction between the same functionalities present at different sites on the mobility-modifying moiety. Whether one uses synthesis or cloning for preparation of oligopeptides, is to a substantial degree depend on the length of the mobility-modifying moiety.

Substituted aryl groups can serve as both mass- and charge-modifying regions. Various functionalities may be substituted onto the aromatic group, e.g., phenyl, to provide mass as well as charges to the e-tag reporter. The aryl group may be a terminal group, where only one linking functionality is required, so that a free hydroxyl group may be acylated, may be attached as a side chain to an hydroxyl present on the e-tag reporter chain, or may have two functionalities, e.g., phenolic hydroxyls, that may serve for phosphite ester formation and other substituents, such as halo, haloalkyl, nitro, cyano, alkoxycarbonyl, alkylthio, etc. where the groups may be charged or uncharged.

The label conjugates may be prepared utilizing conjugating techniques that are well known in the art. M may be synthesized from smaller molecules that have functional groups that provide for linking of the molecules to one another, usually in a linear chain. Such functional groups include carboxylic acids, amines, and hydroxy- or thiol-groups. In accordance with the present invention the charge-imparting moiety may have one or more side groups pending from the core chain. The side groups have a functionality to provide for linking to a label or to another molecule of the charge-imparting moiety. Common functionalities resulting from the reaction of the functional groups employed are exemplified by forming a covalent bond between the molecules to be conjugated. Such functionalities are disulfide, amide, thioamide, dithiol, ether, urea, thiourea, guanidine, azo, thioether, carboxylate and esters and amides containing sulfur and phosphorus such as, e.g., sulfonate, phosphate esters, sulfonamides, thioesters, etc., and the like.

The linkages of the components of the e-tag moiety are discussed above. The linkage between the detectable moiety and the mobility-modifying moiety is generally stable to the action of the cleavage-inducing moiety, so that the mobility-modifying moiety and detectable moiety may be released as an intact unit from the e-tag probe during the cleavage of the e-tag reporter from the e-tag probe.

For the most part, the mobility-modifying moiety may be a bond, where the detectable moiety or label is directly bonded to the target-second binding agent, or a link of from about 1 to about 500 or more, usually about 1 to about 300 atoms, more usually about 2 to about 100 atoms in the chain. In this embodiment, the total number of atoms in the chain will depend to a substantial degree on the diversity required to recognize all the targets to be determined. The chain of the mobility-modifying moiety for the most part is comprised of carbon, nitrogen, oxygen, phosphorous, boron, and sulfur. Various substituents may be present on the mobility-modifying moiety, which may be naturally present as part of the naturally occurring monomer or introduced by synthesis. Functionalities which may be present in the chain include amides, phosphate esters, ethers, esters, thioethers, disulfides, borate esters, sulfate esters, etc. The side chains include amines, ammonium salts, hydroxyl groups, including phenolic groups, carboxyl groups, esters, amides, phosphates, heterocycles, particularly nitrogen heterocycles, such as the nucleoside bases and the amino acid side chains, such as imidazole and quinoline, thioethers, thiols, or other groups of interest to change the mobility of the electrophoretic tag.

The mobility-modifying moiety may be a homooligomer or a heterooligomer, having different monomers of the same or different chemical characteristics, e.g., nucleotides and amino acids. In one embodiment, the e-tag moieties will have a linker, which provides the linkage between the mobility-modifying moiety and the detectable label molecule, usually a fluorescer, or a functionality that may be used for linking to a detectable label molecule. By having different functionalities, which may be individually bonded to a detectable label molecule, one enhances the opportunity for diversity of the electrophoretic tags. Using different fluorescers for joining to the different functionalities, the different fluorescers can provide differences in light emission and charge-to-mass ratios for the electrophoretic tags.

Attaching Multiple Electrophoretic Tags to Binding Moieties

In assays involving polypeptides, it is advantageous to have the release of multiple e-tag reporters for a binding event involving an individual target molecule. In a sense, this results in an amplification of signal. Desirably, the number of e-tag reporters released for each such binding event is about $6 \times 10^3$ to about $6 \times 10^{10}$, preferably, about $6 \times 10^4$ to about $6 \times 10^8$. Where the polypeptide-second binding agent has a plurality of sites for attachment such as, for example, an antibody, there is a plurality of binding sites on the antibody for attachment of e-tag moieties. When the polypeptide-second binding agent of the e-tag probe binds to the polypeptide and the first second binding agent of the first binding agent binds to the induced binding site on the polypeptide thus bringing a cleavage-inducing moiety into close proximity to the cleavable linkage, a plurality of e-tag reporters is released for a binding event involving a single polypeptide. For example, attachment of e-tag moieties to an antibody may result in about 2 to about 10 molecules of e-tag moieties per antibody molecule.

To further enhance the number of e-tag reporters released, the e-tag moieties are cleavably attached to a hub, to which a polypeptide-second binding agent of the e-tag probe is also attached in a relatively permanent manner. For a polypeptide-second binding agent that has a plurality of attachment sites, a plurality of hubs may be attached to the polypeptide-second binding agent where each hub has a plurality of e-tag moieties for release. The hub nucleus is, therefore, a polyfunctional material, normally polymeric, having a plurality of functional groups, e.g., hydroxy, amino, mercapto, carboxy, ethylenic, aldehyde, etc., as sites for linking. The functionalities on the hub should be those that are reactive with a functionality on the e-tag moiety or the polypeptide-second binding agent to be attached. Some functionalities are preferred over others because of their ability to resist participation in unwanted side reactions. The hub nucleus may be water soluble or water insoluble. The hub nucleus is usually at least about 35,000 molecular weight and may be about 10 million or more molecular weight, but usually under about 600,000, more usually under about 300,000. Illustrative hub nuclei include polysaccharides, polypeptides, polynucleotides, ion exchange resins, and the like. The hub is in one aspect a branched linker, which has multiple sites for attachment of e-tag moieties. The multiple site linkers have an attachment site for attaching the polypeptide-second binding agent and a plurality of sites for attachment of a plurality of e-tag moieties. Of course, the e-tag moieties must be attached by means of linkages that comprise a functionality that is cleavable by the cleavage-inducing moiety in accordance with the present invention.

In one embodiment the hub nucleus is a hydrophilic polymer, generally, an addition or condensation polymer with multiple functionality to permit the attachment of multiple moieties. One class of polymers that is useful for the reagents of the present invention comprises the polysaccharide polymers. Polysaccharides such as dextrans, sepharose, polyribose, polyxylose, and the like may be used. Another class of polymers are those that result from the addition polymerization of substituted ethylene or butadiene type monomers, including short chain unsaturated monomers such as propylene, wherein these monomers have substituents that are hydrophilic groups or can be derivatized to hydrophilic groups. Suitable hydrophilic groups that may be attached to the ethylene include hydroxy, carboxy and the ester and amides thereof, amines, and the like. If acrylic acid monomers are used, the acid can be derivatized to suitable reactive groups prior to or subsequent to polymerization. Thus, for example, the ester formed from ethylene glycol and acrylic acid provides a hydroxyl group for derivatization to the components of the e-tag probe. Other suitable polymers include polyallyl amines and alcohols such as, for example, polyvinyl alcohol. In addition to utilizing polymers derived from a single monomer, mixed polymers may also be employed. In this case, the hydrophilicity may be provided by a non-reactive component such as polyethylene glycol, which is then further polymerized to monomers that bear the appropriate functional groups for reaction with the components of the e-tag probe. One such polymer is a copolymer of polyethylene glycol with polyvinyl alcohol. One specific example of a hub is dextran to which about 10 to about 300 molecules of e-tag moieties may be attached per one molecule of dextran.

A particle may be employed to enhance the number of e-tag moieties present in the e-tag probe. The particles may be solid (e.g., comprised of organic and inorganic polymers or latex), oil droplets (e.g., hydrocarbon, fluorocarbon, silicon fluid), or vesicles (e.g., synthetic such as phospholipid or natural such as cells and organelles). The solid particles are normally polymers, either addition or condensation polymers, which are readily dispersible in an assay medium. The e-tag moieties are linked to the particle by cleavable linkages consistent with the present invention. In this way about 100 to about $10^5$ e-tag moieties may be linked to a single particle. The particle usually has at least one polypeptide-second binding agent attached to it. It is also within the purview of the present invention to attach multiple dextran molecules to the particle and to link multiple e-tag moieties to the dextran by means of cleavable linkages as discussed above.

In a particular embodiment of an e-tag probe of the invention, the polypeptide-second binding agent is an antibody. A number of different reactions may be used to covalently attach compounds to antibodies. This has been accomplished by reaction of the amino acid residues of the antibody molecule, including the amine groups of lysine, the free carboxylic acid groups of glutamic and aspartic acid, the sulfhydryl groups of cysteine and the various moieties of the aromatic amino acids. The conjugation to an antibody may be random or site-directed. For site-directed conjugation the linker or mobility-modifying moiety may be joined in any convenient manner to a unit of the target-second binding agent, such as the Fc portion of an antibody or disulfides in the hinge region. For random conjugation amine groups (e.g., N-terminal or lysine) of the antibody may be employed. Alternatively, carboxylate groups (e.g., C-terminal, aspartic acid, glutamic acid) may be used. Other examples include thiol groups. A primary consideration in binding to an antibody is retention of antibody recognition properties or specificity and activity.

Specific approaches are known for attachment to an antibody. One such approach is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of the antibody molecule. In another approach a Schiff base reaction is employed to link compounds to antibody molecules. This method involves the periodate oxidation of the compound to be linked that contains glycol or hydroxy groups, thus forming an aldehyde that is then reacted with the antibody molecule. Attachment occurs via formation of a Schiff base with amino groups of the antibody molecule. Furthermore, isocyanates have been used as coupling agents for covalently attaching compound to antibodies. Suitable linkers for reaction with oxidized antibodies or oxidized antibody fragments include those containing an amine selected from the group consisting of primary amine, secondary amine, hydrazine, hydrazide, hydroxylamine, phenylhydrazine, semicarbazide and thiocarbazide groups. Such reactive functional groups may exist as part of the structure of the linker, or may be introduced by suitable chemical modification of linkers not containing such groups.

In a particular approach an antibody containing polysaccharide chains is oxidized to produce reactive aldehyde groups. Such oxidation may be achieved by, for example, periodate as known in the art. Hub molecules such as, for example, amino-dextran molecules, having e-tag moieties attached thereto by cleavable linkages are attached to the aldehyde groups on the antibody by reductive amination forming secondary amine linkages.

Accordingly, in the present invention one or more hub molecules may be attached to an antibody by one of the aforementioned approaches to achieve relatively permanent linkage under the conditions employed in the present methods. Of course, consistent with the present invention the e-tag moieties are attached to the hub by means of a cleavable linkage or attached directly to the antibody by means of such cleavable linkage. Upon the binding of a polypeptide by the first binding agent and by the e-tag probe comprising the antibody, which brings the e-tag probe in close proximity to the cleavage-inducing reagent, multiple e-tag reporters are released for subsequent detection and for relating to the presence and/or amount of a polypeptide present.

As used herein, the term "capture ligand," refers to a group that is typically included within the target-second binding agent portion of an e-tag probe and is capable of binding specifically to a "capture agent" or receptor. The interaction between such a capture ligand and the corresponding capture agent may be used to separate uncleaved e-tag probes from released e-tag reporters. If desired, the receptor may be used to physically sequester the molecules to which it binds, entirely removing intact e-tag probes containing the polypeptide-binding region or modified polypeptide-binding regions retaining the ligand. These modified polypeptide-binding regions may be as a result of degradation of the starting material, contaminants during the preparation, aberrant cleavage, etc., or other nonspecific degradation products of the polypeptide second binding agent. As above, a ligand, exemplified by biotin, is attached to the polypeptide-binding region so as to be separated from the e-tag reporter upon cleavage.

A receptor for the ligand may be used. Such receptors include natural or synthetic receptors, such as immunoglobulins, lectins, enzymes, etc., avidin, and so forth. Desirably, the receptor is positively charged, naturally as in the case of avidin, or is made so, by the addition of a positively charged moiety or moieties, such as ammonium groups, basic amino acids, etc. Avidin binds to the biotin attached to the detection probe and its degradation products. Avidin is positively charged, while the cleaved electrophoretic tag is negatively charged. Thus the separation of the cleaved electrophoretic tag from, not only uncleaved probe, but also its degradation products, is easily achieved by using conventional separation methods. Alternatively, the receptor may be bound to a solid support or high molecular weight macromolecule, such as a vessel wall, particles, e.g., magnetic particles, cellulose, agarose, etc., and separated by physical separation or centrifugation, dialysis, etc. This method further enhances the specificity of the assay and allows for a higher degree of multiplexing.

As a general matter, one may have two ligands, if the nature of the polypeptide-second binding agent permits. As described above, one ligand can be used for sequestering e-tag moieties bound to the polypeptide-binding region, retaining the first ligand from products lacking the first ligand. Isolation and concentration of the e-tag moieties bound to a modified polypeptide-binding region lacking the first ligand would then be performed. In using the two ligands, one would first combine the reaction mixture with a first receptor for the first ligand for removing polypeptide-binding region retaining the first ligand. One could either separate the first receptor from the composition or the first receptor would be retained in the composition, as described. This would be followed by combining the resulting composition, where the polypeptide-binding region containing the first ligand is bound to the first receptor, with the second receptor, which would serve to isolate or enrich for modified polypeptide-binding region lacking the first ligand, but retaining the second ligand. The second ligand could be the detectable label; a small molecule for which a receptor is available, e.g., a hapten, or a portion of the e-tag probe could serve as the second ligand. After the product is isolated or enriched, the e-tag reporter could be released by denaturation of the receptor, displacement of the product, high salt concentrations and/or organic solvents, etc.

Depending upon the reagent to which the e-tag moiety is attached as discussed above, there may be a single e-tag moiety or a plurality of e-tag moieties, generally ranging from about 1 to about $10^5$, more usually ranging from about 1 to about 300, more particularly ranging from about 1 to about 20 depending on whether or not a hub or particle is employed. The number of e-tag moieties bonded to a single target-binding region depends upon the sensitivity required, the solubility of the e-tag moiety, the effect on the assay of a plurality of e-tag moieties, and the like.

Synthesis of e-tag Probes

The chemistry for performing the types of syntheses to form the charge-imparting moiety or mobility modifier as a peptide chain is well known in the art. See, for example, Marglin, et al., Ann. Rev. Biochem. (1970) 39:841-866. In general, such syntheses involve blocking, with an appropriate protecting group, those functional groups that are not to be involved in the reaction. The free functional groups are then reacted to form the desired linkages. The peptide can be produced on a resin as in the Merrifield synthesis (Merrifield, J. Am. Chem. Soc. (1980) 85:2149-2154 and Houghten et al., Int. J. Pep. Prot. Res. (1980) 16:311-320. The peptide is then removed from the resin according to known techniques.

A summary of the many techniques available for the synthesis of peptides may be found in J. M. Stewart, et al., "Solid Phase Peptide Synthesis, W. H. Freeman Co, San Francisco (1969); and J. Meienhofer, "Hormonal Proteins and Peptides", (1973), vol. 2, p. 46, Academic Press (New York), for solid phase peptide synthesis; and E. Schroder, et al., "The Peptides", vol. 1, Academic Press (New York), 1965 for solution synthesis.

In general, these methods comprise the sequential addition of one or more amino acids, or suitably protected amino acids, to a growing peptide chain. Normally, a suitable protecting group protects either the amino or carboxyl group of the first amino acid. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide. The protecting groups are removed, as desired, according to known methods depending on the particular protecting group utilized. For example, the protecting group may be removed by reduction with hydrogen and palladium on charcoal, sodium in liquid ammonia, etc.; hydrolysis with trifluoroacetic acid, hydrofluoric acid, and the like.

For synthesis of e-tag probes employing phosphoramidite, or related, chemistry many guides are available in the literature: Handbook of Molecular Probes and Research Products, 8th edition (Molecular Probes, Inc., Eugene, Oreg., 2002); Beaucage and Iyer, Tetrahedron, 48: 2223-2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. Many of these chemistries allow components of the electrophoretic probe to be conveniently synthesized on an automated DNA synthesizer, e.g. an Applied Biosystems, Inc. (Foster City, Calif.) model 392 or 394 DNA/RNA Synthesizer, or the like.

Synthesis of e-tag reagents comprising nucleotides as part of the mobility-modifying moiety can be easily and effectively achieved via assembly on a solid phase support using standard phosphoramidite chemistries. The resulting mobility modifying moiety may be linked to the label and/or polypeptide-second binding agent as discussed above.

Electrophoretic Separation Media

An important aspect of the invention is the production of detectable products by separated electrophoretic tags by a reaction involving the signal amplification moiety and one or more substrates in the electrophoretic separation medium. Preferably, electrophoretic separation media is provided that include one or more leuco dyes as substrates for the signal amplification moieties of the tags. More preferably, the substrate is leuco fluorescein. Electrophoretic separation media of the invention includes a aqueous buffer that permits the control of pH and salt concentration over conventional ranges for capillary electrophoresis. In one aspect, the electrophoretic separation media includes sieving media, such as polyacrylamide, dimethylacrylamide, poly(vinylpyrrolidone), poly(ethylene oxide), poly(vinyl alcohol), and the like, e.g. Goetzinger et al, Electrophoresis, 19: 242-248 (1998); Madabhushi et al, Electrophoresis, 19: 224-230 (1998); Gao et al, Anal. Chem., 70: 1382-1388 (1998); Liang et al, Electrophoresis, 19: 2447-2453 (1998); and the like. Preferably, concentration of sieving polymers is in the range of about 0.1 percent to about 4.0 percent. Additional additives may be desirable depending on the chemical and physical nature of the electrophoretic tag and the leuco dyes being employed. Such additives include phosphate or borate buffers to reduce protein interaction with capillary walls and to maintain pH, e.g. between about 3 and 9, zwitterions such as O-phosphorylethylethanolamine, surfactants such as sodium dodecyl sulfate, charged polymers such as dextran sulfate, and the like.

An important aspect of the invention is a system for detecting a plurality of analytes that includes the elements of separating released electrophoretic tag in an electrophoretic separation medium disposed in an electrophoresis apparatus that comprises a separation vessel, such as a capillary tube, microfluidics device, or the like. The system also includes the use of electrophoretic probes of the invention, the production of electrophoretic tags therefrom, and the use of the signal amplification moieties to generate detectable products after separation. Preferably, detectable products are oxidized leuco dyes in the electrophoretic separation media that are detected by their fluorescent emissions.

Methods for Use of e-tag Reagents

The following general discussion of methods and examples of specific assays are by way of illustration and not limitation. One skilled in the art will be able to apply the technology herein in assaying for any analytes in most assay formats that will be apparent to the skilled artisan particularly protein assays and the area of chemical genetics.

In carrying out the assays, the components, i.e., the sample, the first reagent and the electrophoretic probes, are combined in an assay medium in any order, usually simultaneously. Alternatively, one or more of the reagents may be combined with one or more of the remaining agents to form a subcombination. The subcombination can then be subjected to incubation. Then, the remaining reagents or subcombination thereof may be combined and the mixture incubated. The amounts of the reagents are usually determined empirically. As a general rule, at least an equal amount of the first reagent and the electrophoretic probe is employed to the highest expected amount of the polypeptides of interest, usually at least about 1.5 fold excess, more usually at least about 2 fold excess and may have about 10 fold excess or more. The components are combined under binding conditions, usually in an aqueous medium, generally at a pH in the range of about 5 to about 10, with buffer at a concentration in the range of about 10 to about 200 mM. These conditions are conventional, where conventional buffers may be used, such as phosphate, carbonate, HEPES, MOPS, Tris, borate, etc., as well as other conventional additives, such as salts, stabilizers, organic solvents, etc. The aqueous medium may be solely water or may include from 0.01 to 80 or more volume percent of a co-solvent.

The combined reagents are incubated for a time and at a temperature that permit a substantial number of binding events to occur. Generally, the time for incubation after combination of all or a portion of the reagents is at least about 5 min, more usually at least about 15 min, before irradiating the mixture or adding the remaining reagents. Moderate temperatures are normally employed for the incubation and usually constant temperature. Incubation temperatures will normally range from about 5° to 99° C., usually from about 15° to 70° C., more usually 20 to 45° C. Temperatures during measurements will generally range from about 10° to 70° C., more usually from about 20° to 45° C., more usually 20° to 25° C.

After the appropriate incubation periods and after all of the reagents have been combined to form a combination comprising the first reagent or cleavage-inducing reagent, the sample and the electrophoretic probe or e-tag probe, the mixture is treated to activate the cleavage-inducing moiety. The nature of the activation is, of course, dependent on the nature of the cleavage-inducing moiety.

The subject invention employs a variety of reagent systems, where a binding event results in release of an e-tag moiety. The effect of the cleavage-inducing moiety is to make or break a bond by physical, chemical or enzymatic means. Each of the products of the different electrophoretic probes or e-tag probes containing polypeptide-binding regions can be accurately detected, so as to determine the occurrence of the binding event involving the induced binding site. Following the binding event, one or more reaction products are produced that exhibit mobilities different from the e-tag probe or probes from which the reaction products derive. The released form of the e-tag, termed the e-tag reporter, exhibits a different mobility and/or mass than the e-tag probe from which it derives. The invention offers a high degree of versatility for screening known and unknown materials. An electrophoretic device may be employed for separation and detection of the e-tag reporter. The electrophoretic device may be connected to a data processor for receiving and processing data from the device, as well as operating the electrophoretic device.

The systems are based on having libraries available comprising a plurality of e-tag reagents that comprise at least a plurality of different mobility-modifying moieties, so as to be separable by electrophoresis with the entities to which the mobility-modifying moieties are attached. The mobility-modifying moieties are retained in the product of the reaction, where the product is modified by the gain and/or loss of a group that changes the mass and may also change the charge of the product, as compared to the starting material. The mobility-modifying moiety is joined to a polypeptide-binding region by a cleavable bond, so that the mobility-modifying moiety is released for analysis subsequent to the binding of the induced binding site to the first binding agent.

The methodologies that may be employed may be heterogeneous or homogeneous. Heterogeneous techniques normally involve a separation step, where unbound label is separated from bound label. On the other hand, homogeneous assays do not require, but may employ, a separation step.

In addition, in many heterogeneous assays it is required that the unbound labeled reagent be separable from the bound labeled reagent. This can be achieved in a variety of ways, each requiring a reagent bound to a solid support that distinguishes between the complex of labeled reagent and polypeptide. The solid support may be a vessel wall, e.g., microtiter well plate well, capillary, plate, slide, beads, including magnetic beads, liposomes, or the like. The primary characteristics of the solid support is that it permits segregation of the bound labeled specific binding member from unbound probe and that the support does not interfere with the formation of the binding complex, nor the other operations of the determination.

The solid support may have the complex directly or indirectly bound to the support. For directly bound, one may have the first reagent or e-tag probe covalently or non-covalently bound to the support. The surface may be activated with various functionalities that will form covalent bonds with the first reagent. These groups may include imino halides, activated carboxyl groups, e.g., mixed anhydrides or acyl halides, amino groups, a-halo or pseudohaloketones, etc. A specific binding member bound to the surface of the support may be used to bind a member of the complex.

Usually, in a heterogeneous mode, the unbound labeled reagent or e-tag probe will be removed by washing the bound material. Where particles or beads are employed, these may be separated from the supernatant before washing, by filtration, centrifugation, magnetic separation, etc. After washing, the support may be combined with a liquid into which the e-tag reporters are to be released and/or the functionality of the e-tag moieties is reacted with the detectable label, followed by or preceded by release. Depending on the nature of the cleavable bond and the method of cleavage, the liquid may include any additional reagents for the cleavage. Where reagents for cleavage are not required, the liquid is conveniently an electrophoretic buffer. For example, where the cleavable linkage is photolabile, the medium may be irradiated with light of appropriate wavelength to release the e-tag reporters. Where detectable labels are not present on the e-tag moieties, the e-tag reporters may be reacted with detectable labels. In some instances the detectable label may be part of the reagent cleaving the cleavable bond, e.g., a disulfide with a thiol. Where there is a plurality of different functionalities on different binding members for reaction with the label, the different labels have functionalities that react with one of the functionalities. The different labels may be added together or individually in a sequential manner. For example, where the functionalities involve thiols, carboxyl groups, aldehydes and olefins, the labels could have activated olefins, alcohols, amines and thiol groups, respectively. By having removable protective groups for one or more of the functionalities, the protective groups may be removed stepwise and the labels added stepwise. In this way cross-reactivity may be avoided. Whether one has the detectable label present initially or one adds the detectable label is not critical to this invention and is frequently governed by whether the polypeptide itself is cleaved by the cleavage-inducing moiety or by the nature of the polypeptides and the first reagent and electrophoretic probes.

In some embodiments, the e-tag reporters may be required to be separated from the reagent solution, where the reagent interferes with the electrophoretic analysis. Depending on the nature of the e-tag reporters and the reagent, one may sequester the e-tag reporters from the reagent by using ion exchange columns, liquid chromatography, an initial electrophoretic separation, and the like. Alternatively, as discussed previously, one may have a capture ligand bound to the e-tag moiety or retained portion of the target-binding region for isolating the e-tag reporter, so as to remove any interfering components in the mixture. Once the solution of e-tag reporters is prepared and free of any interfering components, the solution may be analyzed electrophoretically. The analysis may employ capillary electrophoresis devices, microfluidic devices or other devices that can separate a plurality of compounds electrophoretically, providing resolved bands of the individual e-tag reporters.

Preferably, the assays in accordance with the present invention are carried out in a homogeneous manner. The protocols for the subject homogeneous assays generally follow the procedures for the analogous heterogeneous assays. These protocols employ a signal producing system that includes the label of the e-tag probe, the cleavable bond associated with the e-tag probe or the polypeptide as the case may be, electromagnetic radiation or other reagents involved in the reaction or for diminishing background signal. In assays involving the production of singlet oxygen, it may be desirable to have a molecule in solution that degrades hydrogen peroxide to reduce its lifetime, in order to prevent reaction between hydrogen peroxide produced by a bound and unbound label-containing reagent.

Generally, the concentrations of the various agents involved with the signal producing system will vary with the concentration range of the individual polypeptides in the samples to be analyzed, generally being in the range of about 10 nM to about 10 mM. Buffers will ordinarily be employed at a concentration in the range of about 10 to about 200 mM. The concentration of each polypeptide will generally be in the range of about 1 pM to about 100 µM, more usually in the range of about 100 pM to about 10 µM. In specific situations the concentrations may be higher or lower, depending on the nature of the analyte, the affinity of the reciprocal binding members, the efficiency of release of the e-tag reporters, the sensitivity with which the e-tag reporters are detected, and the number of polypeptides, as well as other considerations.

In accordance with one aspect of the invention, a group of polypeptides may be monitored in a multiplexed reaction. In this case, a plurality of pairs of e-tag probes corresponding to the various polypeptides are combined with a sample in a single reaction vessel under conditions where the e-tag reporter is released from the reagent when a respective polypeptide binds to a binding agent and the medium is treated to generate singlet oxygen. The e-tag reporters are either labeled for detection or the label is added by means of a reactive functionality present on the e-tag moiety. The labeled e-tag reporters of the reaction are resolved from one another on the electrophoretic device, and again are monitored as they move past the detector. The level of multiplexing possible in this system is limited only by the degree of resolution that can be obtained between a designated set of e-tag reporters on the electrophoretic device.

An additional degree of flexibility can be conferred on the assay by the stage at which the e-tag moieties are labeled. As described above, each e-tag moiety may already contain a detectable label when introduced into the reaction. Alternatively, an e-tag moiety may contain a functionality allowing it to bind to a label after reaction with the sample is complete. In this embodiment, an e-tag probe comprising a functionality for binding to a detectable label is combined with a sample. After a reaction to modify the mobility of the e-tag probe if its target polypeptide is present in the sample, additional reagents are combined in a sample vessel with the products of the first reaction, which reacts with the modified e-tag reporter(s) to add a detectable label.

The sample to be analyzed may take a variety of forms, including but not limited to, water; biological samples such as blood, serum, plasma, urine, tissue samples, food, feed products or plant material; or non-biological samples such as soil, water, industrial samples.

In general, some degree of purification may be required prior to carrying out an assay of the invention. Methods for purifying nucleic acid or protein targets are generally known in the art and may easily be adapted to fit the particular sample subjected to analysis.

The samples may be processed using lysis, nucleic acid separation from proteins and lipids and vice versa and/or enrichment of different fractions. For nucleic acid related determinations, the source of the DNA may be any organism, prokaryotic or eukaryotic cells, tissue, environmental samples, etc. The DNA or RNA may be isolated by conventional means, RNA may be reverse transcribed, DNA may be amplified, as with PCR, primers may be used with capture ligands for use in subsequent processing, the DNA may be fragmented using restriction enzymes, specific sequences may be concentrated or removed using homologous sequences bound to a support, or the like. Proteins may be isolated using precipitation, extraction, and chromatography. The proteins may be present as individual proteins or combined in various aggregations, such as organelles, cells, viruses, etc. Once the target components have been preliminarily treated, the sample may then be combined with the cTag reporter targeted binding proteins.

The cleavage of the nucleic acid bound to the template results in a change in the melting temperature of the cTag residue with release of the cTag. By appropriate choice of the primer and/or protocol, one can retain the primer bound to the template and the cTag containing sequence can be cleaved and released from the template to be replaced by a cTag containing probe.

The tables below summarize various assay formats in which electrophoretic tags of the invention may be employed.

| Binding and Multiplexed Assays. | | |
| --- | --- | --- |
| Formats | Recognition Event | Amplification Mode | cTag Release |
| Multiplexed assays Sequence recognition for example for multiplexed gene expression, SNP's scoring etc . . . | Solution hybridization followed by enzyme recognition Solution hybridization followed by channeling | PCR, Invader  Amplification due to turnover of cTag binding moiety; OR amplification due to release of multiple cTags | 5' nuclease 3' nuclease Restriction enzyme Ribonuclease H Singlet Oxygen ($^1O_2$) Hydrogen Peroxide ($H_2O_2$) Light, energy transfer |

-continued

Binding and Multiplexed Assays.

| Formats | Recognition Event | Amplification Mode | cTag Release |
|---|---|---|---|
| Patches in microfluidic channels-integrated assay and separation device | Target captured on solid surface; cTag probe mixture hybridized to target; unbound probes removed; cTag reporter is released, separated and treated to produce detectable product. | (10 to 100,000) per binding event Amplification from release of multiple cTag reporters (10 to 100,000) per probe | Light, enzyme, $'O_2$, $H_2O_2$, Fluoride, reducing agent, MS, others |

Immunoassays

| Format | Recognition Event | Amplification Mode | cTag Release |
|---|---|---|---|
| Proteomics Multiplexed Immunoassays | Sandwich assays Antibody-1 decorated with Sensitizer while antibody-2 is decorated with singlet oxygen cleavable cTags Competition assays Antibody-1 decorated with Sensitizer while antibody-2 is decorated with singlet oxygen cleavable cTags | A few (2-10) cTags released per binding event OR Amplification from release of multiple cTags (10 to 100,000) per binding event | Singlet Oxygen ($'O_2$) |
| | Sandwich assays Antibody-1 decorated with Glucose oxidase while antibody-2 is decorated with hydrogen peroxide cleavable cTags Competition assays Antibody-1 decorated with Glucose oxidase while antibody-2 is decorated with hydrogen peroxide cleavable cTags | | Hydrogen Peroxide ($H_2O_2$) |
| Patches in microfluidic channels; integrated assay and separation device | Sandwich assays Antibody-1 is attached to a solid surface while antibody-2 is decorated with cleavable cTags Competition assays Antibody-1 is attached to a solid surface while antibody-2 is decorated with cleavable cTags | | Light; Enzymes, singlet oxygen, hydrogen peroxide fluoride, reducing agents, mass spectra, others |

The assays may be performed in a competitive mode or sandwich mode, as illustrated in the tables, above. In the competitive mode, a capture ligand competes with a cTag probe comprising a ligand for binding to a capture agent, where the capture agent is bound to a support. In one exemplary assay an antibody is the capture ligand and an anti-immunoglobulin antibody is the capture agent that is bound to the support. In this mode, the binding sites of the capture agent become at least partially filled by the ligand, reducing the number of available binding sites for the cTag probe. Thus, the number of cTag probes that bind to the capture agent will be in proportion to the number of free ligand molecules present, assuming similar binding affinities.

In the sandwich mode, the target is able to bind at the same time to different cature agents; a first support bound capture agent and a second capture agent that binds at a site on the target molecule different from the site at which the support bound capture agent binds. The second capture agent is decorated with cTags, e.g., singlet oxygen or hydrogen peroxide cleavable cTags. The resulting complex has three components, where the target serves to link the cTag probe to the support.

In carrying out the assays, the components are combined, usually with the ligand added first, then the cTag probe in the competitive mode and in any order in the sandwich mode. The particular ratio of ligand molecules to labeled molecules will depend on the binding affinities, the length of time the mixture is incubated, the off rates for the target molecule with respect to the capture agent, the size of the sample and the like. The components are combined under binding conditions, usually in an aqueous medium, generally at a pH in the range of 5-10, with buffer at a concentration in the range of about 10 to 200 mM. These conditions are conventional and standard buffers are used, such as phosphate, carbonate, HEPES, MOPS, Tris, borate, etc., together with additional conventional additives, such as salts, stabilizers, organic solvents, etc.

Usually, the unbound cTag probe will be removed by washing the solid support to which the cTag probe is bound. Where particles or beads are employed, these may be separated from the supernatant before washing, by filtration, centrifugation, magnetic separation, etc. After washing, the support may be combined with a liquid into which the cTag reporters are to be released.

Depending on the nature of the cleavable bond and the method of cleavage, the liquid may include reagents for the cleavage and/or reagents for generation of a detectable signal, e.g., a leucodye. Where reagents for cleavage are not required, the liquid is conveniently an electrophoretic buffer. For example, where the cleavable linkage is photo labile, the support may be irradiated with light of appropriate wavelength which serves to release the cTag reporters and to convert a pre-dye, such as leucofluorescein into a detectable form, e.g. fluroescein.

Where a reagent is necessary for cleavage, the cTag reporters may be required to be separated from the reagent solution, where the reagent interferes with the electrophoretic analysis. Depending on the nature of the cTag reporters, the catalytic group and the reagent(s), one may sequester the cTag reporters from the reagent(s) using ion exchange columns, liquid chromatography, an initial electrophoretic separation, etc. Alternatively, one may have a capture ligand bound to the cTag probe or the retained portion of the linking group for isolating the cTag probe that does not bind the target, so as to remove any interfering components in the mixture.

Whether the reagent(s) necessary for generation of a detectable signal are present initially, e.g., in the electrophoretic medium or added later, e.g. following separation is not critical to the invention and will frequently be governed by the nature of the catalytic chemical group, the nature of the target, and the nature of the detectable signal. For the most part, it will be a matter of convenience as to the particular method one chooses for providing the reagents for reaction with the catalytic chemical group in order to generate a detectable signal.

Once the solution of cTag reporters is prepared and free of any interfering components, the solution may be analyzed electrophoretically. The analysis may employ capillary electrophoresis devices, microfluidic devices or other devices that can separate a plurality of compounds electrophoretically, providing resolved bands of the individual cTag reporters.

Generally, the concentrations of the various agents involved in production of the detectable signal will vary with the concentration range of the individual target antiligands in the samples to be analyzed, generally being in the range of about 10 nM to 10 mM. Buffers will ordinarily be employed at a concentration in the range of about 10 to 200 mM. The concentration of each target antiligand will vary, but will generally be in the range of about 1 pM to about 100 μM, more usually in the range of about 100 pM to 10 μM. In specific situations the concentrations may be higher or lower, depending on the nature of the target antiligand, the affinity of the ligand for the target antiligand, the efficiency of release of the cTag reporters, the sensitivity with which the signal generated following the cTag-mediated catalytic reaction is detected, and the number of target antiligands, as well as other considerations.

In one preferred embodiment, a reactive species produced in the assay is activated resulting in cleavage of a bond, so that one may obtain release of the cTag reporter. Assays that find applicability to this aspect of the invention are described in U.S. Pat. Nos. 4,233,402, 5,616,719, 5,807,675, and 6,002,000. In practicing the method, one combines the sample with one or more reagents, with the particular order of addition varying dependent upon the nature of the reagents. In one approach, the binding reagents and the sample are combined and allowed to incubate, generally at least about 5 min, more usually at least about 15 min, before irradiating the mixture or adding the remaining reagents.

Nucleic Acid Analyses

In general, the cTag methods for assays involving numerous types of nucleic acid targets will be substantially the same, however they may differ dependent upon the nature of the analysis. For example, SNP detection is, for the most part, the most stringent in its requirements, due to the necessity of high fidelity.

For a nucleic acid sample, after processing, a mixture of cTag probes is combined with the sample suspected of containing the target under hybridization conditions, in conjunction with other reagents, as necessary. Where the reaction is heterogeneous, the cTag probe will include a capture ligand, capable of binding specifically to a capture agent for sequestering hybrids to which the cTag probe is bound. In this case, all of the DNA sample carrying the capture ligand will be sequestered, both with and without cTag probe. After sequestering the sample, and removing non-specifically bound cTag probe under a predetermined stringency based on the sequence of the nucleic acid ligand component of the cTag probe, using washing at an elevated temperature, salt concentration, organic solvent, etc., the cTag reporter is released into an electrophoretic buffer solution for analysis. More specific examples applicable to nucleic acid analyses using the cTag methodology include, but are no limited to the following.

(i) Primer Extension Reaction in Nucleic Acid Analyses

The extension reaction is performed by bringing together the necessary combination of reagents, and subjecting the mixture to conditions for carrying out the desired primer extension. Such conditions depend on the nature of the extension, e.g., PCR, single primer amplification, LCR, NASBA, 3 SR and so forth, where the enzyme which is used for the extension has 5'-3' nuclease activity. The extension reaction may be carried out as to both strands or as to only a single strand. Where pairs of primers and cTag probes comprising a nucleic acid ligand are used for both strands, conveniently, the nucleic acid ligand will be the same but the bases will be different. In this situation, one may wish to have a cleavable linkage positioned such that for the same nucleic acid target, one would obtain the same cTag reporter. Alternatively, if the number of nucleic acid targets to be determined is not too high, one could use different cTag probes for each of the strands. Usually, the reaction will be carried out by using amplifying conditions, so as to provide an amplified signal for each nucleic acid target. Amplification conditions normally employ thermal cycling, where after primer extension and release of cTag reporters associated with targets that are present, the mixture is heated to denature the double-stranded DNA, cooled, where the primer and cTag probe can rehybridize and the extension can be repeated.

Reagents for conducting the primer extension are substantially the same reaction materials for carrying out an amplification, such as an amplification indicated above. The nature and amounts of these reagents are dependent on the type of amplification conducted. In addition to oligonucleotide primers, the reagents also comprise nucleoside triphosphates and a nucleotide polymerase having 5'-3' nuclease activity.

The nucleoside triphosphates employed as reagents in an amplification reaction include deoxyribonucleoside triphosphates such as the four common deoxyribonucleoside triphosphates dATP, dCTP, dGTP and dTTP. The term "nucleoside triphosphates" also includes derivatives and analogs thereof, which are exemplified by those derivatives that are recognized and polymerized in a similar manner to the underivatized nucleoside triphosphates.

The nucleotide polymerase employed is a catalyst, usually an enzyme, for forming an extension of an oligonucleotide primer along a polynucleotide such as a DNA template, where the extension is complementary thereto. The nucleotide polymerase is a template dependent polynucleotide polymerase and utilizes nucleoside triphosphates as building blocks for extending the 3'-end of a polynucleotide to provide a sequence complementary with the polynucleotide template. Usually, the catalysts are enzymes, such as DNA polymerases, for example, prokaryotic DNA polymerase (I, II, or III), T4 DNA polymerase, T7 DNA polymerase, Vent DNA polymerase, Pfu DNA polymerase, Taq DNA polymerase, and the like. Polymerase enzymes may be derived from any source, such as eukaryotic or prokaryotic cells, bacteria such as E. coli, plants, animals, virus, thermophilic bacteria, genetically modified enzymes, and so forth.

Thermal cycling conditions are employed for conducting an amplification involving temperature or thermal cycling and primer extension such as in PCR or single primer amplification, and the like. The pH and the temperature are selected so as to cause, either simultaneously or sequentially, dissociation of any internally hybridized sequences, hybridization or annealing of the oligonucleotide primer and cTag probe with the target sequence, extension of the primer, release of the cTag reporter from cTag probe bound to the target nucleic acid sequence, and dissociation of the extended primer. This usually involves cycling the reaction medium between two or more temperatures. In conducting such a method, the medium is cycled between two to three temperatures. The temperatures for thermal cycling generally range from about 50° C. to 100° C., more usually from about 60° C. to 95° C. Relatively low temperatures of from about 30° C. to about 65° C. can be employed for the extension steps, while denaturation and hybridization can be carried out at a temperature of from about 50° C. to about 105° C. The reaction medium is initially at about 20° C. to about 45° C., preferably, about 25° C. to about 35° C. Relatively low temperatures of from about 50° C. to about 80° C., preferably, 50° C. to about 60° C., are employed for the hybridization or annealing steps, while denaturation is carried out at a temperature of from about 80° C. to about 100° C., preferably, 90° C. to about 95° C., and extension is carried out at a temperature of from about 70° C. to about 80° C., usually about 72° C. to about 74° C. The duration of each cycle may vary and is usually about 1 to 120 seconds, preferably, about 5 to 60 seconds for the denaturation steps, and usually about 1 to 15 seconds, preferably, about 1 to 5 seconds, for the extension steps. It is to be understood that the actual temperature and duration of the cycles employed are dependent on the particular amplification conducted and are well within the knowledge of those skilled in the art.

Generally, an aqueous medium is employed. Other polar co-solvents may also be employed, usually oxygenated organic solvents of from 1-6, more usually from 1-4, carbon atoms, including alcohols, ethers, formamide and the like. Usually, these co-solvents, if used, are present in less than about 70 weight percent, more usually in less than about 30 weight percent.

The pH for the medium is usually in the range of about 4.5 to 9.5, more usually in the range of about 5.5 to 8.5, and preferably in the range of about 6 to 8. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another. The medium may also contain materials required for enzyme activity such as a divalent metal ion (usually magnesium).

Various ancillary materials will frequently be employed in accordance with the methods of the present invention. For example, in addition to buffers and salts, the medium may also comprise stabilizers for the medium and the reaction components. Frequently, the medium may also include proteins such as albumins, quaternary ammonium salts, polycations such as spermine, surfactants, particularly non-ionic surfactants, binding enharicers, e.g., polyalkylene glycols, or the like.

The reaction is conducted for a time sufficient to produce the desired number of copies of each of the nucleic acid targets suspected of being present. Generally, the time period for conducting the entire method will be from about 10 to 200 minutes. It is usually desirable to minimize the time period for amplification.

The concentration of the nucleotide polymerase is usually determined empirically. Preferably, a concentration is used that is sufficient for the amplification to be robust. Exemplary enzymes include Pfu DNA polymerase (native and recombinant) from Stratagene, La Jolla, Calif., UlTma DNA polymerase from Perkin Elmer, Foster City, Calif., rBst DNA polymerase from Epicentre Technologies, Madison, Wis., Vent DNA polymerase from New England Biolabs, Beverly, Mass., Tli DNA polymerase from Promega Corp., Madison, Wis., and Pwo DNA polymerase from Boehringer Mannheim, Indianapolis, Ind., and the like.

The initial concentration of each of the cTag probes containing the nucleic acid ligand for binding to the nucleic acid target can be as low as about 50 pg/μL in a sample. After amplification the concentration of each polynucleotide should be at least about 10 pM, generally in the range of about 10 pM to about 10 nM, usually from about 10 to $10^{10}$, more usually from about $10^3$ to $10^8$ molecules in a sample, preferably at least $10^{-21}$ M in the sample and may be $10^{-10}$ to $10^{-19}$ M, more usually $10^{-14}$ to $10^{-19}$ M. In general, the reagents for the reaction are provided in amounts to achieve extension of the oligonucleotide primers.

The concentration of the oligonucleotide primer(s) will be about 1 to about 20 μM and is usually about 1 to about 10 μM, preferably, about 1 to about 4 μM, for a sample size that is about 10 fM. Preferably, the concentration of the oligonucleotide primer(s) is substantially in excess over, preferably at least about $10^7$ to about $10^{10}$ times greater than, more preferably, at least about $10^9$ times greater than, the concentration of the corresponding target polynucleotides.

The amount of the cTag probes will be 10 to about 500 nM and is usually about 50 to about 200 nM for a sample size that is about 10 fM. Preferably, the concentration of the cTag probes is substantially in excess over, preferably at least about $10^7$ times greater than, more preferably, at least about $10^8$ times greater than, the concentration of each of the nucleic acid target molecules.

The concentration of the nucleoside triphosphates in the medium can vary widely; preferably, these reagents are present in an excess amount. The nucleoside triphosphates are usually present in about 10 μM to about 1 mM, preferably, about 20 to about 400 μM.

The order of combining of the various reagents to form the combination may vary. Usually, a sample containing the nucleic acid target is combined with a pre-prepared combination of nucleoside triphosphates and nucleotide polymerase. The oligonucleotide primers and the cTag probes may be included in the prepared combination or may be added subsequently. However, simultaneous addition of all of the above, as well as other step-wise or sequential orders of addition, may be employed provided that all of the reagents described above are combined prior to the start of the reactions. The oligonucleotide pairs may be added to the combination of the reagents at or prior to initiation of the primer extension reaction and may be replenished from time-to-time during the primer extension reaction.

For quantitation, one may choose to use controls, which provide a signal in relation to the amount of the target that is present or is introduced. Where one is dealing with a mixture of nucleic acid targets, as in the case of mRNA in a lysate, one may use known amounts of one or more different mRNAs in the particular cell types as the standards. Desirably, one would have at least one controls, preferably at least 2 controls, where the variation in number between any two controls is at least about $10^2$, and the total range is at least about $10^3$, usually at least about $10^4$. In a preferred approach, one relies on synthetic targets as the control(s).

In some cases a control system is added for quantitation. In this aspect, the control system will comprise at least two control sequences, usually at least 3 control sequences and generally not more than about 6 control sequences, where the upper limit is primarily one of convenience and economy, since additional control sequences will usually not add significant additional precision. The control sequences will usually be at least about 50 nucleotides, more usually at least about 100 nucleotides different in length, e.g., shorter. The control sequences have a common primer sequence and different target sequences, which are intended to parallel the primer sequence and the nucleic acid ligand sequence of the cTag probes in size, spacing and response to the primer extension conditions. In carrying out the primer extension reaction for a nucleic acid-containing sample, different numbers of molecules of the different control sequences are added such that one can graph the result to give a signal/number relationship. This graph is used to relate the signal detected per target molecule to the number of molecules present.

As exemplary of the subject invention, four target polynucleotides T1, T2, T3 and T4 are employed. Oligonucleotide primers PR1, PR2, PR3 and PR4 are employed, each respectively capable of hybridizing to a sequence in the respective target polynucleotides. Also employed are four nucleic acid ligand containing cTag probes, PB 1, PB2, PB3 and PB4. Each of the cTag probes comprises a catalytic chemical group I1, I2, I3 or I4, respectively. In this example, there is a mismatch between PB2 and T2, which comprises a single nucleotide polymorphism (SNP). The reaction medium comprising the above reagents and nucleoside triphosphates and a template dependent polynucleotide polymerase having 5' to 3' exonuclease activity is treated under amplification conditions. Primers PR1, PR2, PR3 and PR4 hybridize to their respective target polynucleotides and are extended to yield extended primers EPR1, EPR2, EPR3 and EPR4. Nucleic acid ligand containing cTag probes, PB 1, PB3 and PB4, which hybridize with their respective target polynucleotides, are acted upon by the exonuclease to cleave a single nucleotide yielding the corresponding cTag reporters. PB2, which does not bind to the target polynucleotide, is not cleaved. The cTag reporters F1, F3 and F4 are injected into a separation channel in a chip for conducting electroseparation. Following separation and excitation and/or exposure to the appropriate reagents, the cTag reporters are converted into detectable products identified by their specific mobility and detectable signal, e.g. fluorescence. In one preferred embodiment, the separation medium includes the reagents necessary for interaction with the catalytic chemical group and generation of a detectable signal. In another preferred embodiment, following separation, one or more reagents necessary for interaction with the catalytic chemical group are added resulting in generation of a detectable signal. In a further embodiment, the full electrophoretic channel or a portion thereof is irradiated at the appropriate wavelength for activation of the catalytic chemical group resulting in generation of a detectable signal. The separated and reacted cTag reporters are related to the presence and amount of the respective nucleic acid target(s).

The selection of the nucleic acid ligand or other target binding sequence for inclusion in the cTag probe will affect the stringency employed during the primer extension, particularly at the stage of hybridization. In a substantial number of samples, the DNA will be heterozygous for target nucleic acid sequence rather than homozygous. In such cases, it is important to avoid false positives which may be detected when the cTag probe binds to the sequence comprising the prevalent nucleotide, as well as the sequence comprising the nucleic acid target, e.g., a SNP. Where the target nucleic acid is homozygous for the prevalent sequence, it is also important that the target binding nucleic acid ligand sequence does not bind to give a false positive. Therefore, the difference in $T_m$ between the target containing sequence and other sequences, e.g., the wild-type sequence in the case of a SNP, will usually be at least about 3° C., more usually at least about 5° C., under the conditions of the primer extension.

In one exemplary protocol, the nucleic acid ligand sequence of the cTag probe is chosen to bind to a particular nucleic acid target sequence. The length of the nucleic acid ligand component of the cTag probe is in part related to the length and binding affinity of the primer. The two sequences act together to ensure that the pair of reagents bind to the proper target sequence. The greater the fidelity of binding of one member of the pair, the less fidelity that is required for the other member of the pair. Since the observed signal will be dependent upon both members of the pair being present, each member serves as a check on the other member for production of the signal. However, since except for the cost, it is relatively easy to make reasonably long oligonucleotides, usually both members of the pair will uniquely hybridize to their respective target sequences. Therefore, the length of the nucleic acid ligand component of the cTag probe will come within the parameters indicated for the primer, but the total number of bases for the two pair members will usually be at least 36, more usually at least about 40.

Depending on the protocol, the cTag reporter is separated from a portion or substantially all of the linking group sequence, usually retaining not more than about 3 nucleotides, more usually not more than about 2 nucleotides and preferably from 0 to 1 nucleotide. By having a cleavable linkage between the charged mobility group, catalytic chemical group and linking group components of the cTag probe and the nucleic acid ligand sequence, the cTag reporter may be freed of all the nucleotides. By having a nuclease-resistant penultimate link in the liking group, a single nucleotide may be included in the cTag reporter.

Each cTag probe has at least one component bound to a catalytic chemical group which facilitates generation of a detectable signal that can be detected electrochemically or by other convenient detection methodologies.

In the case of nucleic acid ligand containing cTag probes, the modified nucleotide is usually at the 5'-end of the nucleic acid sequence, but the modified nucleotide may be anywhere in the sequence, particularly when there is a single nuclease susceptible linkage found in the cTag probe. Since the determination is based on at least partial degradation of the cTag probe, having the modified nucleotide at the 5' end ensures that if degradation occurs, the cTag reporter will be released. Since nucleases may clip at other than the terminal phosphate link, it is desirable to prevent cleavage at other than the terminal phosphate link. In this way one avoids the confusion of having cTag reporters joined to different numbers of nucleotides after cleavage, based on interaction with the same target. Cleavage at the terminal phosphate can be relatively assured by using a linking group that is not cleaved by the nuclease, more particularly having only the ultimate linkage susceptible to hydrolysis by a nuclease. For example, one may use a thiophosphate, phosphinate, phosphoramidate, or a linking group other than a phosphorous acid derivative, such as an amide, boronate, or the like. The particular hydrolase resistant linkage will be primarily one of synthetic convenience, so long as degradation of the binding affinity is not sacrificed. If desired, all of the linking groups other than the ultimate linking group may be resistant to nuclease hydrolysis.

One, usually a plurality, of nucleic acid targets is simultaneously determined by combining a sample containing target DNA with one or a plurality, respectively, of reagent pairs under conditions of primer extension. Each pair of reagents includes a primer which binds to target DNA and a nucleic acid ligand containing cTag probe, which binds to the site of the SNP and has a catalytic chemical-group (I), a charged mobility group ($M_j$), a linking group (L) and a nucleic acid ligand wherein the base complementary to the SNP is typically at other than a terminus of the nucleic acid ligand component of the cTag probe. The conditions of primer extension employ a polymerase having 5'-3' exonuclease activity, dNTP's and auxiliary reagents to permit efficient primer extension. The primer extension is performed, whereby detector sequences bound to the target DNA are degraded with release of a cTag reporter. By having each SNP associated with its own cTag probe and corresponding cTag reporter, one can determine the SNP's, which are present in the target DNA for which pairs of reagents have been provided.

The pairs of reagents are DNA sequences which are related to a SNP site. The primer binds to the target DNA upstream from the SNP site in the direction of extension. The nucleic acid ligand component of the cTag probe binds downstream from the primer in the direction of extension and binds to a sequence which includes the SNP. The primer sequence will usually be at least about 12 bases long, more usually at least 18 bases long and usually fewer than 100 bases, and more usually fewer than 60 bases. The primer will be chosen to bind substantially uniquely to a target sequence under the conditions of primer extension, so that the sequence will normally be one that is conserved or the primer is long enough to bind in the presence of a few mismatches, usually fewer than about 10 number % mismatches. By knowing the sequence, which is upstream from the SNP of interest, one may select a sequence, which has a high G-C ratio, so as to have a high binding affinity for the target sequence. In addition, the primer should bind reasonably close to the SNP, usually not more than about 200 bases away, more usually not more than about 100 bases away, and preferably within about 50 bases. Since the farther away the primer is from the SNP, the greater amount of dNTPs that will be expended, there will usually be no advantage in having a significant distance between the primer and the SNP detection sequence. Generally, the primer will be at least about 5 bases away from the SNP.

The complementary base to the SNP may be anywhere in the nucleic acid ligand component of the cTag probe, desirably at other than the terminal nucleoside to enhance the fidelity of binding. The nucleic acid ligand sequence will be designed to include adjacent nucleotides, which provide the desired affinity for the hybridization conditions. The nucleic acid ligand component of the cTag probe may be synthesized by any convenient means, such as described in Matthews, et al., Anal. Biochem. (1988) 169:1-25; Keller, et al., "DNA Probes," $2^{nd}$ edition (1993) Stockton Press, New York, N.Y.; and Wetmur, CRITICAL REVIEWS IN BIOCHEMISTRY AND MOLECULAR BIOLOGY (1991) 26:227-259.

The number of reagent pairs may be varied widely, from a single pair to two or more pairs, usually at least about 5 pairs, more usually at least about 9 pairs and may be 20 pairs or more. By virtue of the use of different cTag probes and the corresponding cTag reporters which have different mobilities and are readily resolvable under conventional capillary electrophoretic conditions, the subject pairs may be used to perform multiplexed operations in a single vessel, where a family of SNPs may be identified. Usually, the total number of different reagent pairs or different target sequences in a single determination will be under 200, more usually under 100 and in many cases will not exceed 50.

The Invader™ Reaction in Nucleic Acid Analyses

In one application of the cTag methodology, the primer includes the complementary base of the SNP. This protocol takes advantage of existing techniques referred to as the Invader™ technology. (See, e.g., U.S. Pat. No. 6,001,567). The protocol involves providing: (a)(i) a cleavage means, which is normally an enzyme, referred to as a cleavase, that recognizes a triplex consisting of the target sequence, a primer which binds to the target sequence and terminates at the SNP position and a cTag probe that binds immediately adjacent to the primer and is displaced from the target at the SNP position, when a SNP is present. The cleavase clips the cTag probe at the site of displacement, releasing a cTag reporter, (ii) a source of target nucleic acid, the target nucleic acid having a first region, a second region and a third region, wherein the first region is downstream from the second region and the second region is contiguous to and downstream from the third region, and (iii) first and second oligonucleotides having 3' and 5' portions, wherein the 3' portion of the first oligonucleotide contains a sequence complementary to the third region of the target nucleic acid and the 5' portion of the first oligonucleotide and the 3' portion of the second oligonucleotide each contain sequences usually fully complementary to the second region of the target nucleic acid, and the 5' portion of the second oligonucleotide contains sequence complementary to the first region of said target nucleic acid; (b) mixing, in any order, the cleavage means, the target nucleic acid, and the first and second oligonucleotides under hybridization conditions that at least the 3' portion of the first oligonucleotide is annealed to the target nucleic acid and at least the 5' portion of the second oligonucleotide is annealed to any target nucleic acid to from a cleavage structure, where the combined melting temperature of the complementary regions within the 5' and 3' portions of the first oligonucleotide when annealed to the target nucleic acid is greater than the melting temperature of the 3' portion of the first oligonucleotide and cleavage of the cleavage structure occurs to cTag reporters; (c) reacting the released reporters in manner effective to generate detectable products; and (d) detecting the products.

Thus, in an Invader assay, the binding of a cTag probe to the 5' end of nucleic acid target sequences results in the formation of cTag reporters when the target sequence is present. In general, the cTag reporters are separated and reacted in a manner effective to generate a detectable product that is detected. By employing a different cTag probe for each nucleic acid target sequence of interest, each corresponding to a cTag reporter having a different electrophoretic mobility, one can readily determine the presence of SNPs or measure multiple sequences in a sample.

Analysis of Reaction Products

Methods for electrophoresis of are well known and are described, for example, in Krylov et al, Anal. Chem., 72: 111R-128R (2000); P. D. Grossman and J. C. Colbum, Capillary Electrophoresis: Theory and Practice, Academic Press, Inc., NY (1992); U.S. Pat. Nos. 5,374,527; 5,624,800; 5,552,028; ABI PRISM 377 DNA Sequencer User's Manual, Rev. A, January 1995, Chapter 2 (Applied Biosystems, Foster City, Calif.); and the like. A variety of suitable electrophoresis media are commercially available from Applied Biosystems and other vendors, including non-crosslinked media, for use with automated instruments such as the Applied Biosysterns "3700" and "3100" Instruments, for example. Optimal electrophoresis conditions, e.g., polymer concentration, pH, temperature, voltage, concentration of denaturing agent, employed in a particular separation depends on many factors, including the size range of the compounds to be separated, their compositions, and the like. Accordingly application of the invention may require standard preliminary testing to optimize conditions for particular separations.

During or after electrophoretic separation, the electrophoretic tags are detected or identified by recording fluorescence signals and migration times (or migration distances) of the separated compounds, or by constructing a chart of relative fluorescent and order of migration of the electrophoretic tags (e.g., as an electropherogram). To perform such detection, the electrophoretic tags can be illuminated by standard means, e.g. a high intensity mercury vapor lamp, a laser, or the like. Typically, the electrophoretic tags are illuminated by laser light generated by a He—Ne gas laser or a solid-state diode laser. The fluorescence signals can then be detected by a light-sensitive detector, e.g., a photomultiplier tube, a charged-coupled device, or the like. Exemplary electrophoresis detection systems are described elsewhere, e.g., U.S. Pat. Nos. 5,543,026; 5,274,240; 4,879,012; 5,091,652; 6,142,162; or the like.

After completion of the reaction, which may be monitored, for example, by monitoring the change in signal such as, e.g., fluorescence as described above, or taking aliquots and assaying for total free e-tag reporters, the mixture may now be analyzed. Depending on the instrument, from one to four different fluorescers activated by the same light source and emitting at different detectable labels may be used. With improvements, five or more different fluorescers may be available, where an additional light source may be required. Electrochemical detection is described in U.S. Pat. No. 6,045,676.

In one embodiment of the presence of each of the cleaved e-tag reporters is determined by the fluorescent label contained in the e-tag moiety. The separation of the mixture of labeled e-tag reporters' is typically carried out by electroseparation, which involves the separation of components in a liquid by application of an electric field, preferably, by electrokinesis (electrokinetic flow) or electrophoretic flow, or a combination of electrophoretic flow within electroosmotic flow, with the separation of the e-tag reporter mixture into individual fractions or bands. Electroseparation involves the migration and separation of molecules in an electric field based on differences in mobility. Various forms of electroseparation include, by way of example and not limitation, free zone electrophoresis, gel electrophoresis, isoelectric focusing, isotachophoresis, capillary electrochromatography, and micellar electrokinetic chromatography. Capillary electrophoresis involves electroseparation, preferably by electrokinetic flow, including electrophoretic, dielectrophoretic and/or electroosmotic flow, conducted in a tube or channel of about 1 to about 200 micrometer, usually, about 10 to about 100 micrometers cross-sectional dimensions. The capillary may be a long independent capillary tube or a channel in a wafer or film comprised of silicon, quartz, glass or plastic.

In capillary electroseparation, an aliquot of the reaction mixture containing the e-tag reporters is subjected to electroseparation by introducing the aliquot into an electroseparation channel that may be part of, or linked to, a capillary device in which the amplification and other reactions are performed. An electric potential is then applied to the electrically conductive medium contained within the channel to effectuate migration of the components within the combination. Generally, the electric potential applied is sufficient to achieve electroseparation of the desired components according to practices well known in the art. One skilled in the art will be capable of determining the suitable electric potentials for a given set of reagents used in the present invention and/or the nature of the cleaved labels, the nature of the reaction medium and so forth. The parameters for the electroseparation including those for the medium and the electric potential are usually optimized to achieve maximum separation of the desired components. This may be achieved empirically and is well within the purview of the skilled artisan.

For a homogeneous assay, the sample, the first and electrophoretic probes, and ancillary reagents are combined in a reaction mixture supporting the cleavage of the linking region. The mixture may be processed to separate the e-tag reporters from the other components of the mixture. The mixture, with or without e-tag reporter enrichment, may then be transferred to an electrophoresis device, usually a microfluidic or capillary electrophoresis device and the medium modified as required for the electrophoretic separation. Where one wishes to remove from the separation channel intact e-tag reporter molecules, a ligand is bound to the e-tag reporter that is not released when the e-tag reporter is released. Alternatively, by adding a reciprocal binding member that has the opposite charge of the e-tag reporter, so that the overall charge is opposite to the charge of the e-tag reporter, these molecules will migrate toward the opposite electrode from the released e-tag reporter molecules. For example, one could use biotin and streptavidin, where streptavidin carries a positive charge. In the case of a peptide analyte, one embodiment would have cleavage at a site where the ligand remains with the peptide analyte. For example, one could have the e-tag moiety substituted for the methyl group of methionine. Using the pyrazolone of the modified methionine, one could bond to an available lysine. The amino group of the pyrazolone would be substituted with biotin. Cleavage would then be achieved with cyanogen bromide, releasing the e-tag reporter, but the biotin would remain with the peptide and any e-tag moiety that was not released from the binding member. Avidin is then used to change the polarity or sequester the e-tag moiety conjugated to the target-second binding agent for the analyte or target-second binding agent.

For capillary electrophoresis one may employ one or more detection zones to detect the separated cleaved labels.

It is, of course, within the purview of the present invention to utilize several detection zones depending on the nature of the reactions, mobility-modifying moieties, and so forth. There may be any number of detection zones associated with a single channel or with multiple channels. Suitable detectors for use in the detection zones include, by way of example, photomultiplier tubes, photodiodes, photodiode arrays, avalanche photodiodes, linear and array charge coupled device (CCD) chips, CCD camera modules, spectrofluorometers, and the like. Excitation sources include, for example, filtered lamps, LEDs, laser diodes, gas, liquid and solid-state lasers, and so forth. The detection may be laser scanned excitation, CCD camera detection, coaxial fiber optics, confocal back or forward fluorescence detection in single or array configurations, and the like.

Detection may be by any of the known methods associated with the analysis of capillary electrophoresis columns including the methods shown in U.S. Pat. No. 5,560,811 (column 11, lines 19-30), U.S. Pat. Nos. 4,675,300, 4,274,240 and 5,324,401, the relevant disclosures of which are incorporated herein by reference. Those skilled in the electrophoresis arts will recognize a wide range of electric potentials or field strengths may be used, for example, fields of 10 to 1000 V/cm are used with about 200 to about 600 V/cm being more typical. The upper voltage limit for commercial systems is about 30 kV, with a capillary length of about 40 to about 60 cm, giving a maximum field of about 600 V/cm. For DNA, typically the capillary is coated to reduce electroosmotic flow, and the injection end of the capillary is maintained at a negative potential.

For ease of detection, the entire apparatus may be fabricated from a plastic material that is optically transparent, which generally allows light of wavelengths ranging from about 180 to about 1500 nm, usually about 220 to about 800 nm, more usually about 450 to about 700 nm, to have low transmission losses. Suitable materials include fused silica, plastics, quartz, glass, and so forth.

Kits for Use of the e-tag Reagents

As a matter of convenience, predetermined amounts of reagents employed in the present invention can be provided in a kit in packaged combination. One exemplary kit for polypeptide analysis can comprise in packaged combination a first reagent comprising a cleavage-inducing moiety and a binding agent for binding to a binding site on the polypeptide that has undergone a post-translational modification. The kit can further comprise one or more electrophoretic probes comprising a specific binding agent for a particular polypeptide cleavably linked to an e-tag reporter. For example, each of the e-tag probes may comprise a polypeptide-second binding agent such as an antibody cleavably linked to an e-tag moiety. The mobility-modifying moiety of each of the e-tag probes has a mobility that allows differentiation of one e-tag reporter from another and is unique to a particular protein of interest. The kits will include at least about 1, usually at least about 10, more usually at least about 20 and frequently at least about 50 or more different probes that can generate e-tag reporters that can be separated by their mobility. On the other hand, where the polypeptide itself is specifically cleaved to provide an e-tag moiety, the kit may include reagents wherein each reagent comprises a detection moiety linked to a moiety for binding to a specific cleaved e-tag moiety.

The kit may further comprise a device for conducting capillary electrophoresis as well as reagents that may be necessary to activate the cleavage-inducing moiety of the cleavage-inducing reagent. The kit can further include various buffered media, some of which may contain one or more of the above reagents.

The relative amounts of the various reagents in the kits can be varied widely to provide for concentrations of the reagents necessary to achieve the objects of the present invention. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit. The kits may also include a written description of a method in accordance with the present invention as described above.

Tag Separation Using Microfluidic Chips

Figure 4A:
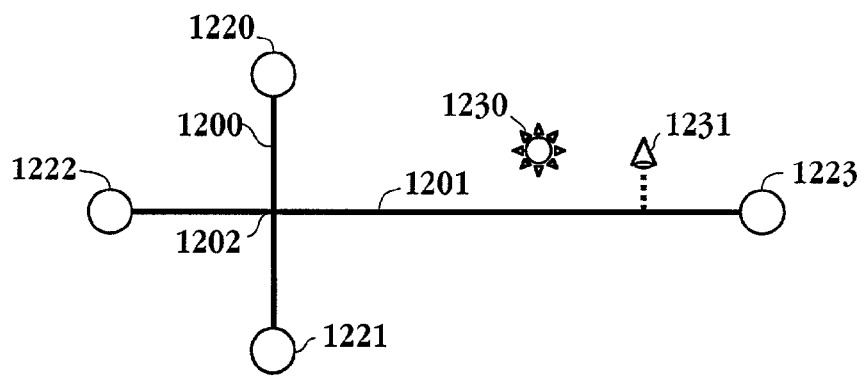
FIGS. 4A-C illustrate the separation of electrophoretic tags of the invention in an electrophoretic separation medium of the invention.

A microfluidic chip is shown in FIG. 4A, consisting of two channels—the sample delivery channel, 1200, and the separation channel, 1201, that intersect at a cross, 1202. The four ends of the two channels terminate with reservoirs, including the sample reservoir, 1220, injection waste reservoir, 1221, running buffer reservoir, 1222, and separation waste reservoir, 1223.

In one exemplary application of the use of catalytic tags, the chip is first primed with separation media containing a leucodye (LF) that can be converted into a fluorescent dye (F) by a reaction catalyzed by a c-tag reporter. The products of a target recognition reaction to be analyzed are placed into the sample reservoir. Sample containing catalytic tag reporters are electrokinetically or pneumatically moved from the sample reservoir toward the injection waste reservoir via the sample delivery channel, then electrokinetically injected into the separation channel toward the separation waste reservoir in order to effect an electrophoretic separation of the c-tag reporters contained in the sample. C-tag reporters separate into bands based on mobility as they are driven toward the detection region 1231. Once the reporters are resolved, a catalytic tag reaction is carried out. Just before the detection region, illumination from a light source, 1230, initiates the catalytic tag reporter reaction, resulting in generation of a fluorescent band coinciding with each catalytic tag reporter band. The fluorescent bands are then detected at the detection region.

In a second exemplary microfluidic chip application of the use of catalytic tags, the same structure and reactions set forth above are applied, using reaction initiation and detection schemes that differ in the following ways. Referring again to FIG. 4A, once catalytic tags are sufficiently resolved in the separation channel, the electrokinetic motion is halted by removing all potential differences between the reservoirs. Instead of employing a stationary illumination point, 1230, the full length of the separation channel is illuminated by either flooding or scanning along its length, the method chosen depending on the flux and/or intensity of light required for efficient catalysis by the c-tag reporter. The resulting fluorescent bands can then be detected by imaging the length of the separation channel via a fixed or scanning CCD. Alternatively, an electric potential can be reapplied to the separation channel, and the fluorescent bands containing the newly generated fluorescent species are electrokinetically transported toward a stationary detector.

Figure 4B:
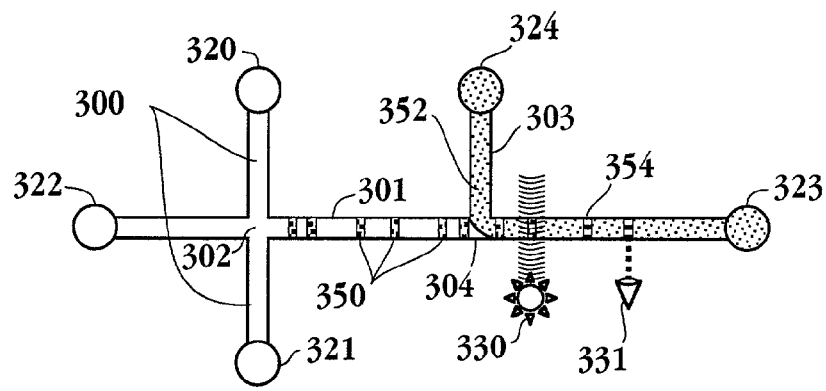

In a second exemplary microfluidic chip configuration for use of catalytic tag methods is shown in FIG. 4B. A microfluidic chip consisting of a sample delivery channel, 300, and a separation channel, 301, intersect at a cross, 302, with reservoirs at each end of the channels, including a sample reservoir, 320, injection waste reservoir, 321, running buffer reservoir, 322, and separation waste reservoir, 323. An additional arm, 303, has a reactant reservoir, 324, at its end, and forms a "T" intersection, 304, with the separation channel between the cross, 302, and the separation waste reservoir. In practicing the method, the chip is first primed with separation media. The products of a target recognition reaction to be analyzed are placed into the sample reservoir. Sample containing catalytic tag reporters are electrokinetically or pneumatically moved from the sample reservoir toward the injection waste reservoir via the sample delivery channel, then electrokinetically injected into the separation channel toward the separation waste reservoir in order to effect an electrophoretic separation of the c-tag reporters contained in the sample. A catalytic reagent for the reaction of the c-tag reporter (illustrated by gray shading) is placed in the reaction reservoir. C-tag reporters separate into bands, 350, in the separation channel based on mobility as they are driven toward the detection region 331. At the "T" intersection, a stream of catalytic reagent, 352, is electrokinetically or pneumatically merged with the separated catalytic tags. The mixed stream continues toward an illumination position, 330, where the catalytic tag reporter reaction is initiated, resulting in generation of a fluorescent band coinciding with each catalytic tag reporter band. The width of the separation channel is small enough and the distance from the "T" intersection to the illumination position is long enough to provide for efficient mixing of the merged streams via lateral diffusion before reaching the illumination position. The resulting fluorescent bands coinciding with each catalytic tag band are then detected at the detection region. Depending on the mechanism employed for the catalytic moiety, the material provided in the reactant reservoir may be a substrate for the catalytic reaction, a cofactor for catalysis, a polypeptide subunit of the catalytic entity, or any other reaction-limiting component of catalysis.

Figure 4C:
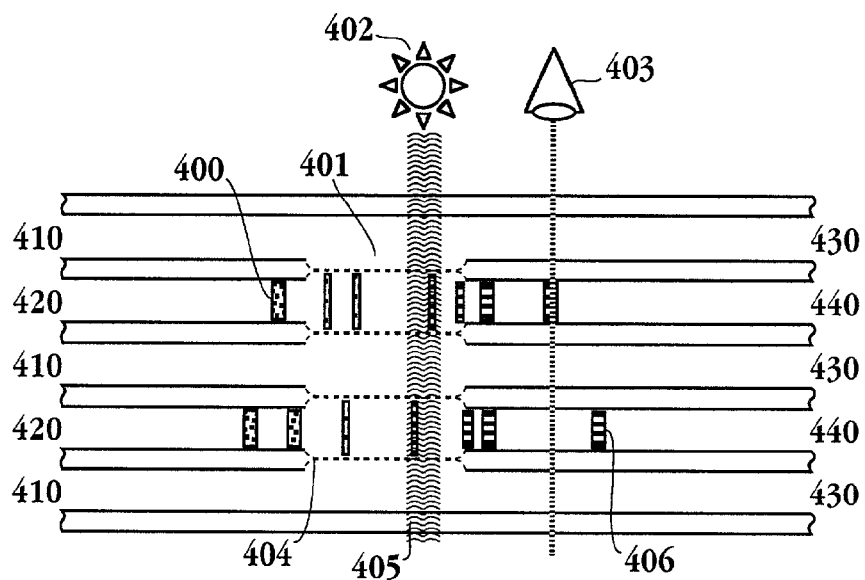

In another exemplary microfluidic chip application useful for analysis of catalytic tag reactions, electromerging is employed as the means for contacting catalytic tags with a required reactant, such as a leucodye (LF), during electrophoretic separation of the c-tag reporters. As shown in FIG. 4C, streams of reactant, 410, and streams of separated catalytic tags, 420, merge at points, 404, in a central region, 401. Incoming catalytic tag reporter bands, 400, and streams of reactant both expand into the central region, where LF from the streams of reactant diffuses into the streams of separated catalytic tag reporters. Within, or immediately downstream of, the central region, an illumination source, 402, initiates the reporter reaction catalyzing conversion of the leucodye into a fluorescent dye in an illumination zone, 405, creating fluorescent bands, 406, coinciding with each c-tag reporter band passing through the illumination zone. The converged reactant and c-tag reporter streams separate into reactant exit channels, 430, and c-tag reporter exit channels, 440, respectively. A detector, 403, either in a scanning or side-launch mode, senses the resulting fluorescent bands. Note that, like the illumination region 405, the detector can interrogate within the central region 401, or downstream in the c-tag reporter exit channels 440, as long as a sufficient contact time is provided between the reactant and c-tag reporter streams prior to initiating the catalytic reaction in the illumination zone. As with the embodiment described in FIG. 4B, the material provided in the streams of reactant, 410, may be a substrate for the catalytic reaction, a cofactor for catalysis, a polypeptide subunit of the catalytic entity, or any other reaction-limiting component of catalysis, depending on the mechanism employed for the catalytic moiety.

What is claimed is:

1. A method of determining the presence or absence of each of a plurality of analytes in a sample, the method comprising the steps of:
   contacting with the sample a plurality of a first binding reagents and a plurality of electrophoretic probes; each of the first binding reagent comprising a cleavage-inducing moiety attached to a first binding agent specific for at least one analyte, and each of the electrophoretic probe comprising a second binding agent specific for one of said analyte and an electrophoretic tag containing a signal amplification moiety, wherein each of said electrophotecic tag has a unique electrophoretic mobility and is attached to the second binding agent by a cleavable linkage; such that when the first binding reagent and an electrophoretic probe bind to the analyte, the cleavable linkage of the electrophoretic probes is within an effective proximity to a cleavage-inducing moiety such that the elcetrophoretic tag is released form its second binding agent;
   electrophoretically separating the released electrophoretic tags in an electrophoretic separation medium that contains or to which is added a substrate capable of reacting with each tag's signal amplification moiety to produce a signal; and
   determining the presence or absence of one or more analytes based on the presence or absence, for each analyte, of a signal corresponding to the electrophoretic mobility of a tag associated with that analyte, by reactions between said substrate and the signal amplification moiety of each released electrophoretic tags.

2. The method of claim 1 wherein said determining includes determining the presence of at least two different analytes, based on different analyte-specific electrophoretic mobilities of the at least two different electrophoretic tags.

3. The method of claim 2 wherein said cleavage-inducing moiety is a sensitizer capable of producing an active species.

4. The method of claim 3 wherein said sensitizer is a photosensitizer, said cleavable linkage is an oxidation-labile linkage, and said active species is selected from the group consisting of hydrogen peroxide, hydroxyl radical, superoxide anion, phenoxy radical, and singlet oxygen.

5. The method of claim 4 wherein said active species is singlet oxygen.

6. The method of claim 5 wherein said first binding agent of said first binding reagent is selected from the group consisting of antibodies, protein receptors, ligands of protein receptors, lectins, biotin-containing moieties, boronic acid-containing moieties, aptamers, enzyme substrates, enzyme cofactors, and enzyme subunits, and wherein said second binding agent of said electrophoretic probe is an antibody or an antibody binding composition.

7. The method of claim 5 wherein said signal amplification moiety is a photosensitizer.

8. The method of claim 7 wherein said signal amplification moiety that is a photosensitizer is in inactivated form prior to cleavage of said cleavable linkage.

9. The method of claim 5 wherein said substrate is a leuco dye.

10. The method of claim 5 wherein said photosensitizer is selected from the group consisting of porphyrins, phthalocyanines, halogenated derivatives of a fluorescein dye, halogenated derivatives of a rhodamine dye, and naphthalocyanines.

11. The method of claim 5 wherein said cleavable linkage comprises an olefin, a thioether, a selenoether, a thiazole, an oxazole, or an imidazole.

12. The method of claim 5 wherein said electrophoretic probe is defined by the following formula: $T\text{-}(L\text{-}E)_k$ wherein: T is a second binding agent specific for a target polypeptide, L is an oxidation-labile linkage, L is an electrophoretic tag, and k is an integer greater than 1.

13. The method of claim 12 wherein L is selected from the group consisting of olefins, thioethers, selenoethers, thiazoles, oxazoles, and imidazoles.

14. The method of claim 13 wherein L, when released from its second binding agent, has a molecular weight in the range of from about 150 to 2500 daltons.

15. The method of claim 13 wherein L has the form (M,I), wherein I is said signal amplification moiety and wherein M is a mobility modifying moiety that is a bond or an organic molecule having up to 100 atoms other than hydrogen selected from the group consisting of carbon, oxygen, nitrogen, phosphorus, boron, and sulfur.

16. A kit for detecting the presence or absence of each of a plurality of analytes in a sample, the kit comprising:
a plurality of a first binding reagents, each comprising a cleavage-inducing moiety attached to a first binding agent specific for at least one analyte; and
a plurality of electrophoretic probes, each comprising a second binding agent specific for one of said analyte and an electrophoretic tag containing a signal amplification moiety, wherein each of said electrophotecic tag has a unique electrophoretic mobility and is attached to the second binding agent by a cleavable linkage; such that when the first binding reagent and an electrophoretic probe bind to the analyte, the cleavable linkage of the electrophoretic probes is within an effective proximity to a cleavage-inducing moiety such that the elcetrophoretic tag is released form its second binding agent.

17. The kit of claim 16 wherein said cleavage-inducing moiety is a first photosensitizer and said cleavable linkage is an oxidation-labile linkage.

18. The kit of claim 17 wherein said first binding agent is selected from the group consisting of antibody binding compositions, protein receptors, ligands of protein receptors, lectins, biotin-containing moieties, boronic acid-containing moieties, aptamers, enzyme substrates, enzyme cofactors, and enzyme subunits.

19. The kit of claim 17 wherein said second binding agents in said one or more electrophoretic probes is an antibody.

20. The kit of claim 19 which includes between 2 to 50 electrophoretic probes.

21. The kit of claim 20 wherein each different electrophoretic probe is specific for a different analyte.

22. The kit of claim 20 wherein each of said one or more electrophoretic probes is defined by the formula:

$$T\text{-}(L\text{-}E)_k$$

wherein T is said second binding agent specific for an analyte, L is said oxidation-labile linkage, E is an electrophoretic tag, and k is an integer greater than 1.

23. The kit of claim 22 wherein L is selected from the group consisting of olefins, thioethers, selenoethers, thiazoles, oxazoles, and imidazoles.

24. The kit of claim 23 wherein E, when released from its second binding agent, has a molecular weight in the range of from about 150 to 2500 daltons.

25. The kit of claim 23 wherein L has the form (M,I), wherein I is said signal amplification moiety and wherein M is a mobility modifying moiety that is a bond or an organic molecule having up to 100 atoms other than hydrogen selected from the group consisting of carbon, oxygen, nitrogen, phosphorus, boron, and sulfur.

* * * * *

UNITED STATES PATENT AND TRADEMARK OFFICE
CERTIFICATE OF CORRECTION

PATENT NO. : 7,358,052 B2  Page 1 of 1
APPLICATION NO. : 10/154641
DATED : April 15, 2008
INVENTOR(S) : Sharat Singh It is certified that error appears in the above-identified patent and that said Letters Patent is hereby corrected as shown below:

Column 56, line 24, please delete "elcetrophoretic" and insert --electrophoretic--.

Column 56, line 25, please delete "form" and insert --from--.

Column 57, line 10, please delete "L is an electrophoretic tag," and insert --E is an electrophoretic tag,--.

Column 57, line 15, please delete "wherein L," and insert --wherein E,--.

Column 57, line 18, please delete "wherein L" and insert --wherein E--.

Column 57, line 39, please delete "elcetrophoretic" and insert --electrophoretic--.

Column 57, line 39, please delete "form" and insert --from--.

Column 58, line 33, please delete "wherein L" and insert --wherein E--.

Signed and Sealed this

Fifteenth Day of July, 2008

JON W. DUDAS
*Director of the United States Patent and Trademark Office*